United States Patent
Morriss et al.

(10) Patent No.: US 9,763,780 B2
(45) Date of Patent: Sep. 19, 2017

(54) DEVICES, SYSTEMS AND METHODS FOR HEART VALVE REPLACEMENT

(71) Applicant: Twelve, Inc., Menlo Park, CA (US)

(72) Inventors: John Morriss, San Francisco, CA (US); Hanson Gifford, III, Woodside, CA (US); James I. Fann, Portola Valley, CA (US); Jean-Pierre Dueri, Los Gatos, CA (US); Darin Gittings, Sunnyvale, CA (US); Michael Luna, San Jose, CA (US); Mark Deem, Mountain View, CA (US); Douglas Sutton, Pacifica, CA (US)

(73) Assignee: Twelve, Inc., Menlo Park, CA (US)

( * ) Notice: Subject to any disclaimer, the term of this patent is extended or adjusted under 35 U.S.C. 154(b) by 261 days.

(21) Appl. No.: 14/352,964

(22) PCT Filed: Oct. 19, 2012

(86) PCT No.: PCT/US2012/061215
§ 371 (c)(1),
(2) Date: Jun. 27, 2014

(87) PCT Pub. No.: WO2013/059743
PCT Pub. Date: Apr. 25, 2013

(65) Prior Publication Data
US 2015/0351903 A1 Dec. 10, 2015

Related U.S. Application Data

(60) Provisional application No. 61/549,037, filed on Oct. 19, 2011.

(51) Int. Cl.
*A61F 2/24* (2006.01)

(52) U.S. Cl.
CPC .......... *A61F 2/2418* (2013.01); *A61F 2/2412* (2013.01); *A61F 2/2436* (2013.01);
(Continued)

(58) Field of Classification Search
CPC .............. A61F 2/2418; A61F 2250/006; A61F 2220/0016; A61F 2230/0054;
(Continued)

(56) References Cited

U.S. PATENT DOCUMENTS

| 3,526,219 A | 9/1970 | Balamuth |
| 3,565,062 A | 2/1971 | Kuris |

(Continued)

FOREIGN PATENT DOCUMENTS

| CN | 1440261 | 9/2003 |
| CN | 101076290 | 11/2007 |

(Continued)

OTHER PUBLICATIONS

US 9,265,606, 02/2016, Buchbinder et al. (withdrawn)
(Continued)

*Primary Examiner* — Katherine M Shi

(57) ABSTRACT

A prosthetic heart valve device (100) for percutaneous replacement of a native heart valve includes an expandable retainer (110) at least partially surrounding and coupled to an inner valve support (120). The device can further include a prosthetic valve (130) coupled to the valve support. The retainer forms a donut-shaped flange (190) having an arcuate outer surface (142) for engaging tissue and an inner lumen defining a passage for blood to flow through the valve support. The retainer can include a plurality of circumferentially positioned, resiliency deformable and flexible ribs (114) which are coupled at their downstream ends 116 to the valve support 120. The flexible ribs, in one embodiment, can have a general C-shape configuration with the tips (117) of (Continued)

the flexible ribs and an opening (119) of the C-shape configuration oriented toward a longitudinal axis (101) of the device.

42 Claims, 36 Drawing Sheets

(52) U.S. Cl.
CPC .............. A61F 2220/0016 (2013.01); A61F 2220/0025 (2013.01); A61F 2250/006 (2013.01)

(58) Field of Classification Search
CPC ............ A61F 2230/0078; A61F 2/2409; A61F 2220/0008; A61F 2/2412; A61F 2220/0075; A61F 2/2427; A61F 2230/0065; A61F 2220/0025; A61F 2/2442; A61F 2/2445; A61F 2/2463; A61F 2/848; A61F 2230/008; A61F 2/2403
USPC ............ 623/1.24, 1.26, 2.1, 2.11, 2.17, 2.18, 623/2.23, 2.37, 2.38
See application file for complete search history.

(56) References Cited

U.S. PATENT DOCUMENTS

| | | |
|---|---|---|
| 3,589,363 A | 6/1971 | Banko et al. |
| 3,667,474 A | 6/1972 | Lapkin et al. |
| 3,823,717 A | 7/1974 | Pohlman et al. |
| 3,861,391 A | 1/1975 | Antonevich et al. |
| 3,896,811 A | 7/1975 | Storz |
| 4,042,979 A | 8/1977 | Angell |
| 4,188,952 A | 2/1980 | Loschilov et al. |
| 4,431,006 A | 2/1984 | Trimmer et al. |
| 4,445,509 A | 5/1984 | Auth |
| 4,484,579 A | 11/1984 | Meno et al. |
| 4,490,859 A | 1/1985 | Black et al. |
| 4,587,958 A | 5/1986 | Noguchi et al. |
| 4,589,419 A | 5/1986 | Laughlin et al. |
| 4,602,911 A | 7/1986 | Ahmadi et al. |
| 4,646,736 A | 3/1987 | Auth |
| 4,692,139 A | 9/1987 | Stiles |
| 4,747,821 A | 5/1988 | Kensey et al. |
| 4,750,902 A | 6/1988 | Wuchinich et al. |
| 4,777,951 A | 10/1988 | Cribier et al. |
| 4,787,388 A | 11/1988 | Hofmann |
| 4,796,629 A | 1/1989 | Grayzel |
| 4,808,153 A | 2/1989 | Parisi |
| 4,819,751 A | 4/1989 | Shimada et al. |
| 4,841,977 A | 6/1989 | Griffith et al. |
| 4,870,953 A | 10/1989 | DonMicheal et al. |
| 4,878,495 A | 11/1989 | Grayzel |
| 4,898,575 A | 2/1990 | Fischell et al. |
| 4,909,252 A | 3/1990 | Goldberger |
| 4,919,133 A | 4/1990 | Chiang |
| 4,920,954 A | 5/1990 | Alliger et al. |
| 4,936,281 A | 6/1990 | Stasz |
| 4,960,411 A | 10/1990 | Buchbinder |
| 4,986,830 A | 1/1991 | Owens et al. |
| 4,990,134 A | 2/1991 | Auth |
| 5,058,570 A | 10/1991 | Idemoto et al. |
| 5,069,664 A | 12/1991 | Guess et al. |
| 5,076,276 A | 12/1991 | Sakurai et al. |
| 5,106,302 A | 4/1992 | Farzin-Nia et al. |
| 5,248,296 A | 9/1993 | Alliger |
| 5,267,954 A | 12/1993 | Nita |
| 5,269,291 A | 12/1993 | Carter |
| 5,295,958 A | 3/1994 | Shturman |
| 5,304,115 A | 4/1994 | Pflueger et al. |
| 5,314,407 A | 5/1994 | Auth et al. |
| 5,318,014 A | 6/1994 | Carter |
| 5,332,402 A | 7/1994 | Teitelbaum |
| 5,344,426 A | 9/1994 | Lau et al. |
| 5,352,199 A | 10/1994 | Tower |
| 5,356,418 A | 10/1994 | Shturman |
| 5,397,293 A | 3/1995 | Alliger et al. |
| 5,411,552 A | 5/1995 | Andersen et al. |
| 5,443,446 A | 8/1995 | Shturman |
| 5,449,373 A | 9/1995 | Pinchasik et al. |
| 5,489,297 A | 2/1996 | Duran |
| 5,584,879 A | 12/1996 | Reimold et al. |
| 5,609,151 A | 3/1997 | Mulier et al. |
| 5,626,603 A | 5/1997 | Venturelli et al. |
| 5,656,036 A | 8/1997 | Palmaz |
| 5,662,671 A | 9/1997 | Barbut et al. |
| 5,681,336 A | 10/1997 | Clement et al. |
| 5,695,507 A | 12/1997 | Auth et al. |
| 5,725,494 A | 3/1998 | Brisken |
| 5,782,931 A | 7/1998 | Yang et al. |
| 5,817,101 A | 10/1998 | Fiedler |
| 5,827,229 A | 10/1998 | Auth et al. |
| 5,827,321 A | 10/1998 | Roubin et al. |
| 5,840,081 A | 11/1998 | Andersen et al. |
| 5,853,422 A | 12/1998 | Huebsch et al. |
| 5,855,601 A | 1/1999 | Bessler et al. |
| 5,868,781 A | 2/1999 | Killion |
| 5,873,811 A | 2/1999 | Wang et al. |
| 5,904,679 A | 5/1999 | Clayman |
| 5,957,882 A | 9/1999 | Nita et al. |
| 5,972,004 A | 10/1999 | Williamson, IV et al. |
| 5,989,208 A | 11/1999 | Nita |
| 5,989,280 A | 11/1999 | Euteneuer et al. |
| 6,047,700 A | 4/2000 | Eggers et al. |
| 6,056,759 A | 5/2000 | Fiedler |
| 6,085,754 A | 7/2000 | Alferness et al. |
| 6,113,608 A | 9/2000 | Monroe et al. |
| RE36,939 E | 10/2000 | Tachibana et al. |
| 6,129,734 A | 10/2000 | Shturman et al. |
| 6,132,444 A | 10/2000 | Shturman et al. |
| 6,168,579 B1 | 1/2001 | Tsugita |
| 6,217,595 B1 | 4/2001 | Shturman et al. |
| 6,254,635 B1 | 7/2001 | Schroeder et al. |
| 6,295,712 B1 | 10/2001 | Shturman et al. |
| 6,306,414 B1 | 10/2001 | Koike |
| 6,321,109 B2 | 11/2001 | Ben-Haim et al. |
| 6,402,679 B1 | 6/2002 | Mortier et al. |
| 6,423,032 B2 | 7/2002 | Parodi |
| 6,425,916 B1 | 7/2002 | Garrison et al. |
| 6,440,164 B1 | 8/2002 | DiMatteo et al. |
| 6,454,737 B1 | 9/2002 | Nita et al. |
| 6,454,757 B1 | 9/2002 | Nita et al. |
| 6,454,799 B1 | 9/2002 | Schreck |
| 6,458,153 B1 | 10/2002 | Bailey et al. |
| 6,461,382 B1 | 10/2002 | Cao |
| 6,494,890 B1 | 12/2002 | Shturman et al. |
| 6,494,891 B1 | 12/2002 | Cornish et al. |
| 6,505,080 B1 | 1/2003 | Sutton |
| 6,530,952 B2 | 3/2003 | Vesely |
| 6,540,782 B1 | 4/2003 | Snyders |
| 6,562,067 B2 | 5/2003 | Mathis |
| 6,565,588 B1 | 5/2003 | Clement et al. |
| 6,569,196 B1 | 5/2003 | Vesely |
| 6,579,308 B1 | 6/2003 | Jansen et al. |
| 6,582,462 B1 | 6/2003 | Andersen et al. |
| 6,595,912 B2 | 7/2003 | Lau et al. |
| 6,605,109 B2 | 8/2003 | Fiedler |
| 6,616,689 B1 | 9/2003 | Ainsworth et al. |
| 6,623,452 B2 | 9/2003 | Chien et al. |
| 6,638,288 B1 | 10/2003 | Shturman et al. |
| 6,648,854 B1 | 11/2003 | Patterson et al. |
| 6,689,086 B1 | 2/2004 | Nita et al. |
| 6,702,748 B1 | 3/2004 | Nita et al. |
| 6,730,121 B2 | 5/2004 | Ortiz et al. |
| 6,746,463 B1 | 6/2004 | Schwartz |
| 6,811,801 B2 | 11/2004 | Nguyen et al. |
| 6,818,001 B2 | 11/2004 | Wulfman et al. |
| 6,843,797 B2 | 1/2005 | Nash et al. |
| 6,852,118 B2 | 2/2005 | Shturman et al. |
| 6,855,123 B2 | 2/2005 | Nita |
| 6,869,439 B2 | 3/2005 | White et al. |
| 6,951,571 B1 | 10/2005 | Srivastava |

(56) References Cited

U.S. PATENT DOCUMENTS

| | | |
|---|---|---|
| 6,986,775 B2 | 1/2006 | Morales et al. |
| 7,018,404 B2 | 3/2006 | Holmberg et al. |
| 7,052,487 B2 | 5/2006 | Cohn et al. |
| 7,077,861 B2 | 7/2006 | Spence |
| 7,125,420 B2 | 10/2006 | Rourke et al. |
| 7,186,264 B2 | 3/2007 | Liddicoat et al. |
| 7,261,732 B2 | 8/2007 | Justino |
| 7,296,577 B2 | 11/2007 | Lashinski et al. |
| 7,381,218 B2 | 6/2008 | Schreck |
| 7,404,824 B1 | 7/2008 | Webler et al. |
| 7,442,204 B2 | 10/2008 | Schwammenthal et al. |
| 7,473,275 B2 | 1/2009 | Marquez |
| 7,510,575 B2 | 3/2009 | Spenser et al. |
| 7,585,321 B2 | 9/2009 | Cribier |
| 7,588,582 B2 | 9/2009 | Starksen et al. |
| 7,621,948 B2 | 11/2009 | Herrmann et al. |
| 7,708,775 B2 | 5/2010 | Rowe et al. |
| 7,748,389 B2 | 7/2010 | Salahieh et al. |
| 7,753,922 B2 | 7/2010 | Starksen |
| 7,753,949 B2 | 7/2010 | Lamphere et al. |
| 7,803,168 B2 | 9/2010 | Gifford et al. |
| 7,857,845 B2 | 12/2010 | Stacchino et al. |
| 7,896,915 B2 | 3/2011 | Guyenot et al. |
| 7,942,928 B2 | 5/2011 | Webler et al. |
| 8,002,826 B2 | 8/2011 | Seguin |
| 8,052,750 B2 | 11/2011 | Tuval et al. |
| 8,062,355 B2 | 11/2011 | Figulla et al. |
| 8,109,996 B2 | 2/2012 | Stacchino et al. |
| 8,114,154 B2 | 2/2012 | Righini et al. |
| 8,252,051 B2 | 8/2012 | Chau et al. |
| 8,398,704 B2 | 3/2013 | Straubinger et al. |
| 8,403,981 B2 | 3/2013 | Forster et al. |
| 8,414,643 B2 | 4/2013 | Tuval et al. |
| 8,449,599 B2 | 5/2013 | Chau et al. |
| 8,496,671 B1 | 7/2013 | Hausen |
| 8,512,252 B2 | 8/2013 | Ludomirsky et al. |
| 8,518,107 B2 | 8/2013 | Tsukashima et al. |
| 8,523,883 B2 | 9/2013 | Saadat |
| 8,532,352 B2 | 9/2013 | Ionasec et al. |
| 8,540,767 B2 | 9/2013 | Zhang |
| 8,545,551 B2 | 10/2013 | Loulmet |
| 8,551,161 B2 | 10/2013 | Dolan |
| 8,579,788 B2 | 11/2013 | Orejola |
| 8,579,964 B2 | 11/2013 | Lane et al. |
| 8,585,755 B2 | 11/2013 | Chau et al. |
| 8,597,347 B2 | 12/2013 | Maurer et al. |
| 8,597,348 B2 | 12/2013 | Rowe et al. |
| 8,608,796 B2 | 12/2013 | Matheny |
| 8,608,797 B2 | 12/2013 | Gross et al. |
| 8,623,077 B2 | 1/2014 | Cohn |
| 8,628,566 B2 | 1/2014 | Eberhardt et al. |
| 8,632,585 B2 | 1/2014 | Seguin et al. |
| 8,632,586 B2 | 1/2014 | Spenser et al. |
| 8,634,935 B2 | 1/2014 | Gaudiani |
| 8,647,254 B2 | 2/2014 | Callas et al. |
| 8,652,203 B2 | 2/2014 | Quadri et al. |
| 8,652,204 B2 | 2/2014 | Quill et al. |
| 8,657,872 B2 | 2/2014 | Seguin |
| 8,672,998 B2 | 3/2014 | Lichtenstein et al. |
| 8,673,001 B2 | 3/2014 | Cartledge et al. |
| 8,679,176 B2 | 3/2014 | Matheny |
| 8,685,086 B2 | 4/2014 | Navia et al. |
| 8,688,234 B2 | 4/2014 | Zhu et al. |
| 8,690,858 B2 | 4/2014 | Machold et al. |
| 8,709,074 B2 | 4/2014 | Solem et al. |
| 8,712,133 B2 | 4/2014 | Guhring et al. |
| 8,715,160 B2 | 5/2014 | Raman et al. |
| 8,721,665 B2 | 5/2014 | Oz et al. |
| 8,721,718 B2 | 5/2014 | Kassab |
| 8,740,918 B2 | 6/2014 | Seguin |
| 8,747,460 B2 | 6/2014 | Tuval et al. |
| 8,758,431 B2 | 6/2014 | Orlov et al. |
| 8,758,432 B2 | 6/2014 | Solem |
| 8,771,292 B2 | 7/2014 | Allen et al. |
| 8,771,345 B2 | 7/2014 | Tuval et al. |
| 8,771,346 B2 | 7/2014 | Tuval et al. |
| 8,777,991 B2 | 7/2014 | Zarbatany et al. |
| 8,778,016 B2 | 7/2014 | Janovsky et al. |
| 8,781,580 B2 | 7/2014 | Hedberg et al. |
| 8,784,482 B2 | 7/2014 | Rahdert et al. |
| 8,792,699 B2 | 7/2014 | Guetter et al. |
| 8,795,356 B2 | 8/2014 | Quadri et al. |
| 8,801,779 B2 | 8/2014 | Seguin et al. |
| 8,808,356 B2 | 8/2014 | Braido et al. |
| 8,808,366 B2 | 8/2014 | Braido et al. |
| 8,812,431 B2 | 8/2014 | Voigt et al. |
| 8,828,043 B2 | 9/2014 | Chambers |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,852,272 B2 | 10/2014 | Gross et al. |
| 8,858,622 B2 | 10/2014 | Machold et al. |
| 8,859,514 B2 | 10/2014 | Crooke et al. |
| 8,859,724 B2 | 10/2014 | Meier et al. |
| 8,864,822 B2 | 10/2014 | Spence et al. |
| 8,870,936 B2 | 10/2014 | Rowe |
| 8,870,948 B1 | 10/2014 | Erzberger et al. |
| 8,870,949 B2 | 10/2014 | Rowe |
| 8,894,702 B2 | 11/2014 | Quadri et al. |
| 8,900,295 B2 | 12/2014 | Migliazza et al. |
| 8,926,694 B2 | 1/2015 | Costello |
| 8,932,348 B2 | 1/2015 | Solem et al. |
| 8,951,285 B2 | 2/2015 | Sugimoto et al. |
| 8,961,597 B2 | 2/2015 | Subramanian et al. |
| 8,968,393 B2 | 3/2015 | Rothstein |
| 8,968,395 B2 | 3/2015 | Hauser et al. |
| 8,974,445 B2 | 3/2015 | Warnking et al. |
| 8,979,922 B2 | 3/2015 | Jayasinghe et al. |
| 8,979,923 B2 | 3/2015 | Spence et al. |
| 8,986,370 B2 | 3/2015 | Annest |
| 8,986,376 B2 | 3/2015 | Solem |
| 8,992,604 B2 | 3/2015 | Gross et al. |
| 9,011,522 B2 | 4/2015 | Annest |
| 9,011,523 B2 | 4/2015 | Seguin |
| 9,017,399 B2 | 4/2015 | Gross et al. |
| 9,023,098 B2 | 5/2015 | Kuehn |
| 9,023,100 B2 | 5/2015 | Quadri et al. |
| 9,050,188 B2 | 6/2015 | Schweich, Jr. et al. |
| 9,066,800 B2 | 6/2015 | Clague et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,132,009 B2 | 9/2015 | Hacohen et al. |
| 9,138,312 B2 | 9/2015 | Tuval et al. |
| 9,138,313 B2 | 9/2015 | McGuckin, Jr. et al. |
| 9,180,005 B1 | 11/2015 | Lashinski et al. |
| 9,192,466 B2 | 11/2015 | Kovalsky et al. |
| 9,192,471 B2 | 11/2015 | Bolling |
| 9,232,942 B2 | 1/2016 | Seguin et al. |
| 9,232,999 B2 | 1/2016 | Maurer et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,271,833 B2 | 3/2016 | Kim et al. |
| 9,289,291 B2 | 3/2016 | Gorman, III et al. |
| 9,289,297 B2 | 3/2016 | Wilson et al. |
| 9,295,547 B2 | 3/2016 | Costello et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,358,108 B2 | 6/2016 | Bortlein et al. |
| 9,387,075 B2 | 7/2016 | Bortlein et al. |
| 9,387,078 B2 | 7/2016 | Gross et al. |
| 9,393,111 B2 | 7/2016 | Ma et al. |
| 2001/0021872 A1 | 9/2001 | Bailey et al. |
| 2001/0049492 A1 | 12/2001 | Frazier et al. |
| 2002/0007219 A1 | 1/2002 | Merrill et al. |
| 2002/0013571 A1 | 1/2002 | Goldfarb et al. |
| 2002/0072792 A1 | 6/2002 | Burgermeister et al. |
| 2002/0082637 A1 | 6/2002 | Lumauig |

(56) References Cited

U.S. PATENT DOCUMENTS

| | | |
|---|---|---|
| 2002/0099439 A1 | 7/2002 | Schwartz et al. |
| 2002/0138138 A1 | 9/2002 | Yang |
| 2002/0151970 A1 | 10/2002 | Garrison et al. |
| 2002/0173841 A1 | 11/2002 | Ortiz et al. |
| 2003/0120340 A1 | 6/2003 | Liska et al. |
| 2003/0139689 A1 | 7/2003 | Shturman et al. |
| 2004/0006358 A1 | 1/2004 | Wulfman et al. |
| 2004/0039412 A1 | 2/2004 | Isshiki et al. |
| 2004/0044350 A1 | 3/2004 | Martin et al. |
| 2004/0057955 A1 | 3/2004 | O'Brien et al. |
| 2004/0082910 A1 | 4/2004 | Constantz et al. |
| 2004/0092858 A1 | 5/2004 | Wilson et al. |
| 2004/0092962 A1 | 5/2004 | Thornton et al. |
| 2004/0092989 A1 | 5/2004 | Wilson et al. |
| 2004/0117009 A1 | 6/2004 | Cali et al. |
| 2004/0122510 A1 | 6/2004 | Sarac |
| 2004/0127979 A1 | 7/2004 | Wilson et al. |
| 2004/0127982 A1 | 7/2004 | Machold et al. |
| 2004/0186558 A1 | 9/2004 | Pavcnik et al. |
| 2004/0199191 A1 | 10/2004 | Schwartz |
| 2004/0230117 A1 | 11/2004 | Tosaya et al. |
| 2004/0230212 A1 | 11/2004 | Wulfman |
| 2004/0230213 A1 | 11/2004 | Wulfman et al. |
| 2004/0243162 A1 | 12/2004 | Wulfman et al. |
| 2005/0007219 A1 | 1/2005 | Ma et al. |
| 2005/0075662 A1 | 4/2005 | Pedersen et al. |
| 2005/0075720 A1 | 4/2005 | Nguyen et al. |
| 2005/0137682 A1 | 6/2005 | Justino |
| 2005/0137690 A1 | 6/2005 | Salahieh et al. |
| 2005/0137691 A1 | 6/2005 | Salahieh et al. |
| 2005/0137695 A1 | 6/2005 | Salahieh et al. |
| 2005/0137697 A1 | 6/2005 | Salahieh et al. |
| 2005/0137698 A1 | 6/2005 | Salahieh et al. |
| 2005/0137700 A1 | 6/2005 | Spence et al. |
| 2005/0137701 A1 | 6/2005 | Salahieh et al. |
| 2005/0137702 A1 | 6/2005 | Haug et al. |
| 2005/0267523 A1 | 12/2005 | Devellian et al. |
| 2006/0058872 A1 | 3/2006 | Salahieh et al. |
| 2006/0106456 A9 | 5/2006 | Machold et al. |
| 2006/0149360 A1* | 7/2006 | Schwammenthal .. A61F 2/2418 623/1.24 |
| 2006/0167543 A1 | 7/2006 | Bailey et al. |
| 2006/0195183 A1 | 8/2006 | Navia et al. |
| 2006/0253191 A1 | 11/2006 | Salahieh et al. |
| 2006/0287719 A1 | 12/2006 | Rowe et al. |
| 2007/0061010 A1 | 3/2007 | Hauser et al. |
| 2007/0073391 A1* | 3/2007 | Bourang ............... A61F 2/2451 623/2.11 |
| 2007/0088431 A1 | 4/2007 | Bourang et al. |
| 2007/0142906 A1* | 6/2007 | Figulla ................. A61F 2/2418 623/2.11 |
| 2007/0173932 A1 | 7/2007 | Cali et al. |
| 2007/0213813 A1* | 9/2007 | Von Segesser ....... A61F 2/2418 623/2.18 |
| 2008/0071369 A1 | 3/2008 | Tuval et al. |
| 2008/0082166 A1 | 4/2008 | Styrc et al. |
| 2008/0103586 A1 | 5/2008 | Styrc et al. |
| 2008/0140189 A1 | 6/2008 | Nguyen et al. |
| 2008/0208332 A1* | 8/2008 | Lamphere ............. A61F 2/2412 623/2.38 |
| 2008/0221672 A1 | 9/2008 | Lamphere et al. |
| 2008/0234728 A1 | 9/2008 | Starksen et al. |
| 2008/0243245 A1 | 10/2008 | Thambar et al. |
| 2008/0243246 A1 | 10/2008 | Ryan et al. |
| 2009/0054969 A1 | 2/2009 | Salahieh et al. |
| 2009/0076586 A1 | 3/2009 | Hauser et al. |
| 2009/0076598 A1 | 3/2009 | Salahieh et al. |
| 2009/0093670 A1 | 4/2009 | Annest et al. |
| 2009/0157174 A1 | 6/2009 | Yoganathan et al. |
| 2009/0164006 A1 | 6/2009 | Seguin et al. |
| 2009/0198315 A1 | 8/2009 | Boudjemline |
| 2009/0216312 A1 | 8/2009 | Straubinger et al. |
| 2009/0240320 A1 | 9/2009 | Tuval et al. |
| 2009/0259292 A1 | 10/2009 | Bonhoeffer |
| 2009/0259306 A1 | 10/2009 | Rowe |
| 2009/0264997 A1 | 10/2009 | Salahieh et al. |
| 2009/0276040 A1 | 11/2009 | Rowe et al. |
| 2009/0281609 A1 | 11/2009 | Benichou et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2009/0319037 A1 | 12/2009 | Rowe et al. |
| 2009/0319038 A1 | 12/2009 | Gurskis et al. |
| 2010/0016958 A1 | 1/2010 | St. Goar et al. |
| 2010/0023117 A1 | 1/2010 | Yoganathan et al. |
| 2010/0030330 A1 | 2/2010 | Bobo et al. |
| 2010/0049313 A1 | 2/2010 | Alon et al. |
| 2010/0076548 A1 | 3/2010 | Konno |
| 2010/0082094 A1 | 4/2010 | Quadri et al. |
| 2010/0094411 A1 | 4/2010 | Tuval et al. |
| 2010/0121436 A1 | 5/2010 | Tuval et al. |
| 2010/0185275 A1 | 7/2010 | Richter et al. |
| 2010/0217382 A1 | 8/2010 | Chau et al. |
| 2010/0249915 A1 | 9/2010 | Zhang |
| 2010/0249923 A1 | 9/2010 | Alkhatib et al. |
| 2010/0298929 A1 | 11/2010 | Thornton et al. |
| 2010/0298931 A1 | 11/2010 | Quadri et al. |
| 2010/0312333 A1 | 12/2010 | Navia et al. |
| 2010/0324554 A1 | 12/2010 | Gifford et al. |
| 2011/0004296 A1 | 1/2011 | Lutter et al. |
| 2011/0015722 A1 | 1/2011 | Hauser et al. |
| 2011/0022166 A1 | 1/2011 | Dahlgren et al. |
| 2011/0029072 A1 | 2/2011 | Gabbay |
| 2011/0040374 A1 | 2/2011 | Goetz et al. |
| 2011/0040375 A1 | 2/2011 | Letac et al. |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0153008 A1 | 6/2011 | Marchand et al. |
| 2011/0172784 A1 | 7/2011 | Richter et al. |
| 2011/0184512 A1 | 7/2011 | Webler et al. |
| 2011/0208293 A1 | 8/2011 | Tabor |
| 2011/0224785 A1 | 9/2011 | Hacohen |
| 2011/0319988 A1 | 12/2011 | Schankereli et al. |
| 2012/0022639 A1 | 1/2012 | Hacohen et al. |
| 2012/0035703 A1 | 2/2012 | Lutter et al. |
| 2012/0035713 A1 | 2/2012 | Lutter et al. |
| 2012/0053680 A1* | 3/2012 | Bolling ................ A61F 2/2445 623/2.11 |
| 2012/0053682 A1 | 3/2012 | Kovalsky et al. |
| 2012/0078347 A1 | 3/2012 | Braido et al. |
| 2012/0078360 A1 | 3/2012 | Rafiee |
| 2012/0101571 A1 | 4/2012 | Thambar et al. |
| 2012/0165930 A1 | 6/2012 | Gifford, III et al. |
| 2012/0179239 A1 | 7/2012 | Quadri |
| 2012/0179244 A1 | 7/2012 | Schankereli et al. |
| 2012/0203336 A1 | 8/2012 | Annest |
| 2012/0283824 A1 | 11/2012 | Lutter et al. |
| 2013/0172978 A1 | 7/2013 | Vidlund et al. |
| 2013/0197354 A1 | 8/2013 | Maschke et al. |
| 2013/0197630 A1 | 8/2013 | Azarnoush |
| 2013/0204356 A1 | 8/2013 | Dwork et al. |
| 2013/0204358 A1 | 8/2013 | Matheny |
| 2013/0226289 A1 | 8/2013 | Shaolian et al. |
| 2013/0226290 A1 | 8/2013 | Yellin et al. |
| 2013/0231735 A1 | 9/2013 | Deem et al. |
| 2013/0238089 A1 | 9/2013 | Lichtenstein et al. |
| 2013/0244927 A1 | 9/2013 | Lal et al. |
| 2013/0253641 A1 | 9/2013 | Lattouf |
| 2013/0253642 A1 | 9/2013 | Brecker |
| 2013/0253643 A1 | 9/2013 | Rolando et al. |
| 2013/0259337 A1 | 10/2013 | Guhring et al. |
| 2013/0261737 A1 | 10/2013 | Costello |
| 2013/0261738 A1 | 10/2013 | Clague et al. |
| 2013/0261739 A1 | 10/2013 | Kuehn |
| 2013/0261741 A1 | 10/2013 | Accola |
| 2013/0268066 A1 | 10/2013 | Rowe |
| 2013/0282060 A1 | 10/2013 | Tuval |
| 2013/0282110 A1 | 10/2013 | Schweich, Jr. et al. |
| 2013/0289642 A1 | 10/2013 | Hedberg et al. |

(56) References Cited

U.S. PATENT DOCUMENTS

| | | |
|---|---|---|
| 2013/0289717 A1 | 10/2013 | Solem |
| 2013/0289718 A1 | 10/2013 | Tsukashima et al. |
| 2013/0296851 A1 | 11/2013 | Boronyak et al. |
| 2013/0296999 A1 | 11/2013 | Burriesci et al. |
| 2013/0304197 A1 | 11/2013 | Buchbinder et al. |
| 2013/0304198 A1 | 11/2013 | Solem |
| 2013/0304200 A1 | 11/2013 | McLean et al. |
| 2013/0309292 A1 | 11/2013 | Andersen |
| 2013/0310436 A1 | 11/2013 | Lowes et al. |
| 2013/0310925 A1 | 11/2013 | Eliasen et al. |
| 2013/0310928 A1 | 11/2013 | Morriss et al. |
| 2013/0317603 A1 | 11/2013 | McLean et al. |
| 2013/0325110 A1 | 12/2013 | Khalil et al. |
| 2013/0325114 A1 | 12/2013 | McLean et al. |
| 2013/0331864 A1 | 12/2013 | Jelich et al. |
| 2013/0338684 A1 | 12/2013 | Hausen |
| 2013/0338763 A1 | 12/2013 | Rowe et al. |
| 2013/0345797 A1 | 12/2013 | Dahlgren et al. |
| 2013/0345803 A1 | 12/2013 | Bergheim, III |
| 2014/0005778 A1 | 1/2014 | Buchbinder et al. |
| 2014/0018906 A1 | 1/2014 | Rafiee |
| 2014/0018913 A1 | 1/2014 | Cartledge et al. |
| 2014/0023261 A1 | 1/2014 | Watanabe et al. |
| 2014/0025164 A1 | 1/2014 | Montorfano et al. |
| 2014/0031928 A1 | 1/2014 | Murphy et al. |
| 2014/0046219 A1 | 2/2014 | Sauter et al. |
| 2014/0046436 A1 | 2/2014 | Kheradvar |
| 2014/0052237 A1 | 2/2014 | Lane et al. |
| 2014/0052240 A1 | 2/2014 | Zhang |
| 2014/0056906 A1 | 2/2014 | Yue et al. |
| 2014/0066895 A1 | 3/2014 | Kipperman |
| 2014/0067048 A1 | 3/2014 | Chau et al. |
| 2014/0067052 A1 | 3/2014 | Chau et al. |
| 2014/0067054 A1 | 3/2014 | Chau et al. |
| 2014/0088071 A1 | 3/2014 | Nakai et al. |
| 2014/0088680 A1 | 3/2014 | Costello et al. |
| 2014/0088693 A1 | 3/2014 | Seguin et al. |
| 2014/0088695 A1 | 3/2014 | Figulla et al. |
| 2014/0094906 A1 | 4/2014 | Spence et al. |
| 2014/0107775 A1 | 4/2014 | Hjelle et al. |
| 2014/0114404 A1 | 4/2014 | Gammie et al. |
| 2014/0114407 A1 | 4/2014 | Rajamannan |
| 2014/0121763 A1 | 5/2014 | Duffy et al. |
| 2014/0128965 A1 | 5/2014 | Rafiee |
| 2014/0135913 A1 | 5/2014 | Lichtenstein et al. |
| 2014/0163652 A1 | 6/2014 | Witzel et al. |
| 2014/0163668 A1 | 6/2014 | Rafiee |
| 2014/0172076 A1 | 6/2014 | Jonsson et al. |
| 2014/0172084 A1 | 6/2014 | Callas et al. |
| 2014/0172085 A1 | 6/2014 | Quadri et al. |
| 2014/0172086 A1 | 6/2014 | Quadri et al. |
| 2014/0179993 A1 | 6/2014 | Alexander et al. |
| 2014/0180401 A1 | 6/2014 | Quill et al. |
| 2014/0188108 A1 | 7/2014 | Goodine et al. |
| 2014/0188215 A1 | 7/2014 | Hlavka et al. |
| 2014/0194920 A1 | 7/2014 | Krahbichler |
| 2014/0194976 A1 | 7/2014 | Starksen et al. |
| 2014/0200397 A1 | 7/2014 | Raman et al. |
| 2014/0200649 A1 | 7/2014 | Essinger et al. |
| 2014/0200657 A1 | 7/2014 | Maurer et al. |
| 2014/0200662 A1 | 7/2014 | Eftel et al. |
| 2014/0214159 A1 | 7/2014 | Vidlund et al. |
| 2014/0219524 A1 | 8/2014 | Takeguchi et al. |
| 2014/0222040 A1 | 8/2014 | Park et al. |
| 2014/0222138 A1 | 8/2014 | Machold et al. |
| 2014/0228942 A1 | 8/2014 | Krahbichler |
| 2014/0228946 A1 | 8/2014 | Chau et al. |
| 2014/0242086 A1 | 8/2014 | Lal et al. |
| 2014/0243860 A1 | 8/2014 | Morris et al. |
| 2014/0243954 A1 | 8/2014 | Shannon |
| 2014/0243964 A1 | 8/2014 | Venkatasubramanian |
| 2014/0249621 A1 | 9/2014 | Eidenschink |
| 2014/0257101 A1 | 9/2014 | Gaudiani |
| 2014/0257466 A1 | 9/2014 | Board et al. |
| 2014/0257467 A1 | 9/2014 | Lane et al. |
| 2014/0257473 A1 | 9/2014 | Rajamannan |
| 2014/0257475 A1 | 9/2014 | Gross et al. |
| 2014/0275757 A1 | 9/2014 | Goodwin et al. |
| 2014/0276395 A1 | 9/2014 | Wilson et al. |
| 2014/0276609 A1 | 9/2014 | Magee et al. |
| 2014/0276782 A1 | 9/2014 | Paskar |
| 2014/0276971 A1 | 9/2014 | Kovach |
| 2014/0277119 A1 | 9/2014 | Akpinar |
| 2014/0277390 A1 | 9/2014 | Ratz et al. |
| 2014/0277404 A1 | 9/2014 | Wilson et al. |
| 2014/0277405 A1 | 9/2014 | Wilson et al. |
| 2014/0277406 A1 | 9/2014 | Arcidi |
| 2014/0277407 A1 | 9/2014 | Dale et al. |
| 2014/0277408 A1 | 9/2014 | Folan |
| 2014/0277409 A1 | 9/2014 | Bortlein et al. |
| 2014/0277410 A1 | 9/2014 | Bortlein et al. |
| 2014/0277411 A1 | 9/2014 | Bortlein et al. |
| 2014/0277412 A1 | 9/2014 | Bortlein et al. |
| 2014/0277420 A1 | 9/2014 | Migliazza et al. |
| 2014/0277422 A1 | 9/2014 | Ratz et al. |
| 2014/0288480 A1 | 9/2014 | Zimmerman et al. |
| 2014/0296878 A1 | 10/2014 | Oz et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296975 A1 | 10/2014 | Tegels et al. |
| 2014/0303719 A1 | 10/2014 | Cox et al. |
| 2014/0303721 A1 | 10/2014 | Fung et al. |
| 2014/0309727 A1 | 10/2014 | Lamelas et al. |
| 2014/0309730 A1 | 10/2014 | Alon et al. |
| 2014/0309731 A1 | 10/2014 | Quadri et al. |
| 2014/0309732 A1 | 10/2014 | Solem |
| 2014/0316516 A1 | 10/2014 | Vidlund et al. |
| 2014/0323448 A1 | 10/2014 | Kim et al. |
| 2014/0324164 A1 | 10/2014 | Gross et al. |
| 2014/0358222 A1 | 12/2014 | Gorman, III et al. |
| 2014/0358224 A1 | 12/2014 | Tegels et al. |
| 2014/0364944 A1 | 12/2014 | Lutter et al. |
| 2014/0371843 A1 | 12/2014 | Wilson et al. |
| 2014/0371844 A1 | 12/2014 | Dale et al. |
| 2014/0371846 A1 | 12/2014 | Wilson et al. |
| 2014/0379074 A1 | 12/2014 | Spence et al. |
| 2014/0379076 A1 | 12/2014 | Vidlund et al. |
| 2015/0005874 A1 | 1/2015 | Vidlund et al. |
| 2015/0005875 A1 | 1/2015 | Tuval et al. |
| 2015/0025623 A1 | 1/2015 | Granada et al. |
| 2015/0032127 A1 | 1/2015 | Gammie et al. |
| 2015/0045878 A1 | 2/2015 | Rowe |
| 2015/0066140 A1 | 3/2015 | Quadri et al. |
| 2015/0094802 A1 | 4/2015 | Buchbinder et al. |
| 2015/0100116 A1 | 4/2015 | Mohl et al. |
| 2015/0112427 A1 | 4/2015 | Schweich, Jr. et al. |
| 2015/0112429 A1 | 4/2015 | Khairkhahan et al. |
| 2015/0112433 A1 | 4/2015 | Schweich, Jr. et al. |
| 2015/0119978 A1 | 4/2015 | Tegels et al. |
| 2015/0119981 A1 | 4/2015 | Khairkhahan et al. |
| 2015/0119982 A1 | 4/2015 | Quill et al. |
| 2015/0127091 A1 | 5/2015 | Cecere et al. |
| 2015/0127096 A1 | 5/2015 | Rowe et al. |
| 2015/0142101 A1 | 5/2015 | Coleman et al. |
| 2015/0142103 A1 | 5/2015 | Vidlund |
| 2015/0142105 A1 | 5/2015 | Bolling et al. |
| 2015/0150678 A1 | 6/2015 | Brecker |
| 2015/0157458 A1 | 6/2015 | Thambar et al. |
| 2015/0157459 A1 | 6/2015 | MacOviak et al. |
| 2015/0164637 A1 | 6/2015 | Khairkhahan et al. |
| 2015/0164641 A1 | 6/2015 | Annest |
| 2015/0173897 A1 | 6/2015 | Raanani et al. |
| 2015/0173898 A1 | 6/2015 | Drasler et al. |
| 2015/0173900 A1 | 6/2015 | Hauser et al. |
| 2015/0190229 A1 | 7/2015 | Seguin |
| 2015/0196390 A1 | 7/2015 | Ma et al. |
| 2015/0196393 A1 | 7/2015 | Vidlund et al. |
| 2015/0202043 A1 | 7/2015 | Zakai et al. |
| 2015/0209137 A1 | 7/2015 | Quadri et al. |
| 2015/0209139 A1 | 7/2015 | Granada et al. |
| 2015/0216655 A1 | 8/2015 | Lane et al. |
| 2015/0216661 A1 | 8/2015 | Hacohen et al. |
| 2015/0223802 A1 | 8/2015 | Tegzes |

(56) References Cited

U.S. PATENT DOCUMENTS

| | | |
|---|---|---|
| 2015/0223934 A1 | 8/2015 | Vidlund et al. |
| 2015/0223935 A1 | 8/2015 | Subramanian et al. |
| 2015/0230920 A1 | 8/2015 | Alfieri et al. |
| 2015/0230921 A1 | 8/2015 | Chau et al. |
| 2015/0238312 A1 | 8/2015 | Lashinski |
| 2015/0238313 A1 | 8/2015 | Spence et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0305861 A1 | 10/2015 | Annest |
| 2015/0305864 A1 | 10/2015 | Quadri et al. |
| 2015/0320553 A1 | 11/2015 | Chau et al. |
| 2015/0327999 A1 | 11/2015 | Board et al. |
| 2015/0328000 A1 | 11/2015 | Ratz et al. |
| 2015/0342733 A1 | 12/2015 | Alkhatib et al. |
| 2015/0351908 A1 | 12/2015 | Keranen et al. |
| 2015/0359628 A1 | 12/2015 | Keranen |
| 2015/0359629 A1 | 12/2015 | Ganesan et al. |
| 2015/0359631 A1 | 12/2015 | Sheahan et al. |
| 2015/0366666 A1 | 12/2015 | Khairkhahan et al. |
| 2015/0374495 A1 | 12/2015 | Ruyra Baliarda et al. |
| 2016/0000983 A1 | 1/2016 | Mohl et al. |
| 2016/0015513 A1 | 1/2016 | Lashinski et al. |
| 2016/0015514 A1 | 1/2016 | Lashinski et al. |
| 2016/0015515 A1 | 1/2016 | Lashinski et al. |
| 2016/0030171 A1 | 2/2016 | Quijano et al. |
| 2016/0038246 A1 | 2/2016 | Wang et al. |
| 2016/0038280 A1 | 2/2016 | Morriss et al. |
| 2016/0038283 A1 | 2/2016 | Divekar et al. |
| 2016/0038286 A1 | 2/2016 | Yellin et al. |
| 2016/0074160 A1 | 3/2016 | Christianson et al. |
| 2016/0106539 A1 | 4/2016 | Buchbinder et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0151156 A1 | 6/2016 | Seguin et al. |
| 2016/0151552 A1 | 6/2016 | Solem |
| 2016/0157999 A1 | 6/2016 | Lane et al. |
| 2016/0158000 A1 | 6/2016 | Granada et al. |
| 2016/0158001 A1 | 6/2016 | Wallace et al. |
| 2016/0158002 A1 | 6/2016 | Wallace et al. |
| 2016/0158003 A1 | 6/2016 | Wallace et al. |
| 2016/0184095 A1 | 6/2016 | Spence et al. |
| 2016/0206424 A1 | 7/2016 | Al-Jilaihawi et al. |

FOREIGN PATENT DOCUMENTS

| | | |
|---|---|---|
| CN | 101291637 | 10/2008 |
| CN | 103491900 | 1/2014 |
| DE | 19605042 | 1/1998 |
| DE | 102006052564 | 12/2007 |
| EP | 186104 | 7/1986 |
| EP | 1512383 | 3/2005 |
| EP | 1545371 | 6/2005 |
| EP | 1551274 | 7/2005 |
| EP | 1629794 | 3/2006 |
| EP | 1646332 | 4/2006 |
| EP | 1702247 | 9/2006 |
| EP | 1734903 | 12/2006 |
| EP | 2026280 | 2/2009 |
| EP | 2037829 | 3/2009 |
| EP | 2081519 | 7/2009 |
| EP | 2111190 | 10/2009 |
| EP | 2142143 | 1/2010 |
| EP | 2167742 | 3/2010 |
| EP | 2203124 | 7/2010 |
| EP | 2278944 | 2/2011 |
| EP | 2306821 | 4/2011 |
| EP | 2327429 | 6/2011 |
| EP | 2400926 | 1/2012 |
| EP | 2410947 | 2/2012 |
| EP | 2444031 | 4/2012 |
| EP | 2488126 | 8/2012 |
| EP | 2509538 | 10/2012 |
| EP | 2549955 | 1/2013 |
| EP | 2549956 | 1/2013 |
| EP | 2566416 | 3/2013 |
| EP | 2586492 | 5/2013 |
| EP | 2618784 | 7/2013 |
| EP | 2623068 | 8/2013 |
| EP | 2626012 | 8/2013 |
| EP | 2626013 | 8/2013 |
| EP | 2629699 | 8/2013 |
| EP | 2633457 | 9/2013 |
| EP | 2637659 | 9/2013 |
| EP | 2641569 | 9/2013 |
| EP | 2654624 | 10/2013 |
| EP | 2656794 | 10/2013 |
| EP | 2656795 | 10/2013 |
| EP | 2656796 | 10/2013 |
| EP | 2667823 | 12/2013 |
| EP | 2670358 | 12/2013 |
| EP | 2676640 | 12/2013 |
| EP | 2688041 | 1/2014 |
| EP | 2693984 | 2/2014 |
| EP | 2697721 | 2/2014 |
| EP | 2713953 | 4/2014 |
| EP | 2714068 | 4/2014 |
| EP | 2723272 | 4/2014 |
| EP | 2723273 | 4/2014 |
| EP | 2723277 | 4/2014 |
| EP | 2739214 | 6/2014 |
| EP | 2741711 | 6/2014 |
| EP | 2750630 | 7/2014 |
| EP | 2750631 | 7/2014 |
| EP | 2755562 | 7/2014 |
| EP | 2755602 | 7/2014 |
| EP | 2757962 | 7/2014 |
| EP | 2777616 | 9/2014 |
| EP | 2777617 | 9/2014 |
| EP | 2782523 | 10/2014 |
| EP | 2785282 | 10/2014 |
| EP | 2790609 | 10/2014 |
| EP | 2793751 | 10/2014 |
| EP | 2809263 | 12/2014 |
| EP | 2810620 | 12/2014 |
| EP | 2814428 | 12/2014 |
| EP | 2814429 | 12/2014 |
| EP | 2819617 | 1/2015 |
| EP | 2819618 | 1/2015 |
| EP | 2819619 | 1/2015 |
| EP | 2416739 | 2/2015 |
| EP | 2833836 | 2/2015 |
| EP | 2838475 | 2/2015 |
| EP | 2849680 | 3/2015 |
| EP | 2849681 | 3/2015 |
| EP | 2852354 | 4/2015 |
| EP | 2873011 | 5/2015 |
| EP | 2875797 | 5/2015 |
| EP | 2882374 | 6/2015 |
| EP | 2886083 | 6/2015 |
| EP | 2886084 | 6/2015 |
| EP | 2895111 | 7/2015 |
| EP | 2901966 | 8/2015 |
| EP | 2907479 | 8/2015 |
| EP | 2945572 | 11/2015 |
| EP | 2948094 | 12/2015 |
| EP | 2948102 | 12/2015 |
| EP | 2964152 | 1/2016 |
| EP | 2967859 | 1/2016 |
| EP | 2967860 | 1/2016 |
| EP | 2967866 | 1/2016 |
| EP | 2968847 | 1/2016 |
| EP | 2981208 | 2/2016 |
| EP | 2982336 | 2/2016 |
| EP | 2999433 | 3/2016 |
| EP | 3003187 | 4/2016 |
| EP | 3003219 | 4/2016 |

(56) References Cited

FOREIGN PATENT DOCUMENTS

| | | |
|---|---|---|
| EP | 3003220 | 4/2016 |
| EP | 3010447 | 4/2016 |
| EP | 3013281 | 5/2016 |
| EP | 3017792 | 5/2016 |
| EP | 3021792 | 5/2016 |
| EP | 3023117 | 5/2016 |
| EP | 3027143 | 6/2016 |
| EP | 3033048 | 6/2016 |
| EP | 3037064 | 6/2016 |
| JP | 6504516 | 5/1994 |
| JP | H10258124 | 9/1998 |
| JP | 2002509756 | 4/2002 |
| JP | 2005280917 | 10/2005 |
| JP | 2008528117 | 7/2008 |
| JP | 2009195712 | 9/2009 |
| JP | 2012500665 | 1/2012 |
| JP | 5219518 | 6/2013 |
| WO | WO-9217118 | 10/1992 |
| WO | WO-9516407 | 6/1995 |
| WO | WO-9904730 | 2/1999 |
| WO | WO-9939648 | 8/1999 |
| WO | WO-9949799 | 10/1999 |
| WO | WO-0110343 | 2/2001 |
| WO | WO-0203892 | 1/2002 |
| WO | WO-0228421 | 4/2002 |
| WO | WO-0239908 | 5/2002 |
| WO | WO-03043685 | 5/2003 |
| WO | WO-2014110169 | 5/2003 |
| WO | WO-2004084746 | 10/2004 |
| WO | WO-2004093728 | 11/2004 |
| WO | WO-2004096097 | 11/2004 |
| WO | WO-2004112657 | 12/2004 |
| WO | WO-2005002466 | 1/2005 |
| WO | WO-2005007219 | 1/2005 |
| WO | WO-2005009285 | 2/2005 |
| WO | WO-2005009506 | 2/2005 |
| WO | WO-2005087140 | 9/2005 |
| WO | WO-2006041877 | 4/2006 |
| WO | WO-2006063199 | 6/2006 |
| WO | WO-2007008371 | 1/2007 |
| WO | WO-2007067820 | 6/2007 |
| WO | WO-2008022077 | 2/2008 |
| WO | WO-2008028569 | 3/2008 |
| WO | WO-2008035337 | 3/2008 |
| WO | WO-2008103497 | 8/2008 |
| WO | WO-2008129405 | 10/2008 |
| WO | WO2009045338 | 4/2009 |
| WO | WO-2010006627 | 1/2010 |
| WO | WO-2010008549 | 1/2010 |
| WO | WO 2010057262 | 5/2010 |
| WO | WO-2010080594 | 7/2010 |
| WO | WO-2010098857 | 9/2010 |
| WO | WO-2010099032 | 9/2010 |
| WO | WO2010117680 | 10/2010 |
| WO | WO-2011047168 | 4/2011 |
| WO | WO-2011051043 | 5/2011 |
| WO | WO-2011057087 | 5/2011 |
| WO | WO-2011072084 | 6/2011 |
| WO | WO-2011106137 | 9/2011 |
| WO | WO-2011106544 | 9/2011 |
| WO | WO-2011111047 | 9/2011 |
| WO | WO-2011137531 | 11/2011 |
| WO | WO2011139747 | 11/2011 |
| WO | WO-2012011018 | 1/2012 |
| WO | WO-2012011108 | 1/2012 |
| WO | WO-2012027487 | 3/2012 |
| WO | WO-2012035279 | 3/2012 |
| WO | WO-2012040655 | 3/2012 |
| WO | WO-2012047644 | 4/2012 |
| WO | WO-2012055498 | 5/2012 |
| WO | WO-2012087842 | 6/2012 |
| WO | WO-2012095455 | 7/2012 |
| WO | WO-2012102928 | 8/2012 |
| WO | WO-2012106602 | 8/2012 |
| WO | WO-2012118508 | 9/2012 |
| WO | WO-2012118816 | 9/2012 |
| WO | WO-2012118894 | 9/2012 |
| WO | WO-2012177942 | 12/2012 |
| WO | WO-2013021374 | 2/2013 |
| WO | WO-2013021375 | 2/2013 |
| WO | WO-2013028387 | 2/2013 |
| WO | WO-2013059743 | 4/2013 |
| WO | WO-2013059747 | 4/2013 |
| WO | WO-2013114214 | 8/2013 |
| WO | WO-2013120181 | 8/2013 |
| WO | WO-2013123059 | 8/2013 |
| WO | WO-2013128432 | 9/2013 |
| WO | WO-2013130641 | 9/2013 |
| WO | WO-2013131925 | 9/2013 |
| WO | WO-2013140318 | 9/2013 |
| WO | WO 2013148017 | 10/2013 |
| WO | WO-2013148018 | 10/2013 |
| WO | WO-2013148019 | 10/2013 |
| WO | WO-2013150512 | 10/2013 |
| WO | WO-2013152161 | 10/2013 |
| WO | WO-2013158613 | 10/2013 |
| WO | WO-2013169448 | 11/2013 |
| WO | WO-2013175468 | 11/2013 |
| WO | WO-2013176583 | 11/2013 |
| WO | WO-2013188077 | 12/2013 |
| WO | WO-2013192107 | 12/2013 |
| WO | WO-2014036113 | 3/2014 |
| WO | WO-2014043527 | 3/2014 |
| WO | WO-2014047111 | 3/2014 |
| WO | WO-2014047325 | 3/2014 |
| WO | WO-2014055981 | 4/2014 |
| WO | WO-2014059432 | 4/2014 |
| WO | WO-2014064694 | 5/2014 |
| WO | WO-2014066365 | 5/2014 |
| WO | WO-2014089424 | 6/2014 |
| WO | WO-2014093861 | 6/2014 |
| WO | WO-2014111918 | 7/2014 |
| WO | WO-2014114794 | 7/2014 |
| WO | WO-2014114795 | 7/2014 |
| WO | WO-2014114796 | 7/2014 |
| WO | WO-2014114798 | 7/2014 |
| WO | WO-2014116502 | 7/2014 |
| WO | WO-2014121280 | 8/2014 |
| WO | WO-2014128705 | 8/2014 |
| WO | WO-2014134277 | 9/2014 |
| WO | WO-2014138194 | 9/2014 |
| WO | WO-2014138284 | 9/2014 |
| WO | WO-2014138482 | 9/2014 |
| WO | WO-2014138868 | 9/2014 |
| WO | WO-2014144100 | 9/2014 |
| WO | WO-2014144937 | 9/2014 |
| WO | WO-2014145338 | 9/2014 |
| WO | WO-2014147336 | 9/2014 |
| WO | WO-2014152306 | 9/2014 |
| WO | WO-2014152375 | 9/2014 |
| WO | WO-2014152503 | 9/2014 |
| WO | WO-2014153544 | 9/2014 |
| WO | WO-2014158617 | 10/2014 |
| WO | WO-2014162181 | 10/2014 |
| WO | WO-2014162306 | 10/2014 |
| WO | WO-2014163705 | 10/2014 |
| WO | WO-2014168655 | 10/2014 |
| WO | WO-2014179391 | 11/2014 |
| WO | WO2014181336 | 11/2014 |
| WO | WO-2014191994 | 12/2014 |
| WO | WO-2014194178 | 12/2014 |
| WO | WO-2014201384 | 12/2014 |
| WO | WO-2014201452 | 12/2014 |
| WO | WO-2014205064 | 12/2014 |
| WO | WO-2014207699 | 12/2014 |
| WO | WO-2014210124 | 12/2014 |
| WO | WO-2014210299 | 12/2014 |
| WO | WO-2015009503 | 1/2015 |
| WO | WO-2015020971 | 2/2015 |
| WO | WO-2015028986 | 3/2015 |
| WO | WO-2015051430 | 4/2015 |
| WO | WO-2015052663 | 4/2015 |
| WO | WO-2015057407 | 4/2015 |
| WO | WO-2015057735 | 4/2015 |

(56) References Cited

FOREIGN PATENT DOCUMENTS

| WO | WO-2015057995 | 4/2015 |
|---|---|---|
| WO | WO-2015061378 | 4/2015 |
| WO | WO-2015061431 | 4/2015 |
| WO | WO-2015061463 | 4/2015 |
| WO | WO-2015061533 | 4/2015 |
| WO | WO-2015075128 | 5/2015 |
| WO | WO-2015081775 | 6/2015 |
| WO | WO-2015089334 | 6/2015 |
| WO | WO-2015092554 | 6/2015 |
| WO | WO2015120122 | 8/2015 |
| WO | WO2015125024 | 8/2015 |
| WO | WO2015127264 | 8/2015 |
| WO | WO2015127283 | 8/2015 |
| WO | WO2015191604 | 8/2015 |
| WO | WO2015191839 | 8/2015 |
| WO | WO2015195823 | 8/2015 |
| WO | WO2015128739 | 9/2015 |
| WO | WO2015128741 | 9/2015 |
| WO | WO2015128747 | 9/2015 |
| WO | WO2015132667 | 9/2015 |
| WO | WO2015132668 | 9/2015 |
| WO | WO2015135050 | 9/2015 |
| WO | WO2015142648 | 9/2015 |
| WO | WO2015142834 | 9/2015 |
| WO | WO2015148241 | 10/2015 |
| WO | WO2015171190 | 11/2015 |
| WO | WO2015171743 | 11/2015 |
| WO | WO2016011185 | 1/2016 |
| WO | WO2016020918 | 2/2016 |
| WO | WO2016027272 | 2/2016 |
| WO | WO2016059533 | 4/2016 |
| WO | WO2016065158 | 4/2016 |
| WO | WO2016073741 | 5/2016 |
| WO | WO2016083551 | 6/2016 |
| WO | WO2016093877 | 6/2016 |
| WO | WO2016097337 | 6/2016 |
| WO | WO2016108181 | 7/2016 |

OTHER PUBLICATIONS

Bernard et al., "Aortic Valve Area Evolution After Percutaneous Aortic Valvuloplasty," European Heart Journal vol. 11, No. 2, pp. 98-107.

Cimino et al., "Physics of Ultrasonic Surgery using Tissue Fragmentation: Part I and Part II", Ultrasound in Medicine and Biologyl,vol. 22, No. 1, pp. 89-100, and pp. 101-117 (1996).

Cimino, Ultrasonic surgery: power quantification and efficiency optimization. Aesthetic surgery journal, 2001, 233-241.

Office Action dated Feb. 23, 2011 from Japanese Patent Application No. 2007-; 545650 together with an English language translation, 1 0 pages.

Cowell et al., "A randomized Trial of Intensive Lipid-Lowering Therapy in Calcific Aortic Stenosis," NEJM vol. 352 No. 23, pp. 2389-2397 (Jun. 9, 2005).

De Korte et al., "Characterization of plaque components and vulnerability with intravascular ultrasound elastography" Phys. Med. Biol. vol. 45, pp. 1465-1475 (2000).

Feldman, "Restenosis Following Successful Balloon Valvuloplasty: Bone Formation in Aortic Valve Leaflets," Cathet Cardiovasc Diagn, vol. 29 No. 1, pp. 1-7 (May 1993).

Final Office Action for U.S. Appl. No. 12/870,270, Mailed Jul. 3, 2012, 7 pages.

Final Office Action for U.S. Appl. No. 11/299,246, Mailed Feb. 17, 2010, 6 pages.

Final Office Action for U.S. Appl. No. 11/299,246, Mailed Jun. 6, 2008, 5 pages.

Final Office Action for U.S. Appl. No. 13/329,083, Mailed Jan. 6, 2014, 9 pages.

Final Office Action for U.S. Appl. No. 13/842,785, mailed Aug. 29, 2014, 5 pages.

Final Office Action for U.S. Appl. No. 13/946,552, Mailed Aug. 29, 2014, 5 pages.

Final Office Action for U.S. Appl. No. 13/946,628, Mailed Sep. 2, 2014, 6 pages.

Fitzgerald et al., "Intravascular Sonotherapy Decreased Neointimal Hyperplasia After Stent Implantation in Swine," Circulation, vol. 103, pp. 1828-1831 (2001).

Freeman et al., "Ultrasonic Aortic Valve Decalcification: Serial Doppler Echocardiographic Follow Up," J Am Coll Cardiol., vol. 16, No. 3, pp. 623-630 (Sep. 1990).

Greenleaf et al., "Selected Methods for Imaging Elastic Properties of Biological Tissues" Annu. Rev. Biomed. Eng., vol. 5, pp. 57-78, (2003).

Gunn et al., "New Developments in Therapeutic Ultrasound-Assisted Coronary Angioplasty," Curr Intery Cardiol Rep., vol. 1 No. 4, pp. 281-290, (Dec. 1990).

Guzman et al., "Bioeffects Caused by Changes in Acoustic Cavitation Bubble Density and Cell Concentration: A Unified Explanation Based on Cell-to-Bubble Ratio and Blast Radius," Ultrasound in Med. & Biol., vol. 29, No. 8, pp. 1211-1222 (2003).

Hallgrimsson et al., "Chronic Non-Rheumatic Aortic Valvular Disease: a Population Study Based on Autopsies," J Chronic Dis.vol. 32 No. 5, pp. 355-363, (1979).

International Search Report and Written Opinion dated May 1, 2012; International Application No. PCT/US2011/065627; Applicant: Foundry Newco XII, Inc.; 10 pages.

International Search Report and Written Opinion dated Dec. 10, 2012; International Application No. PCT/US2012/043636; Applicant: Foundry Newco XII, Inc.; 21 pages.

International Search Report and Written Opinion dated Jan. 30, 2013; International Application No. PCT/US2012/061215; Applicant: Foundry Newco XII, Inc.; 11 pages.

International Search Report and Written Opinion dated Jan. 30, 2013; International Application No. PCT/US2012/061219; Applicant: Foundry Newco XII, Inc.; 9 pages.

International Search Report and Written Opinion for International App. No. PCT/US2005/044543, dated May 22, 2007, 8 pages.

International Search Report and Written Opinion for International App. No. PCT/US2014/014704, mailed Sep. 4, 2014, 18 pages.

International Search Report and Written Opinion for International Application No. PCT/US2014/038849, mailed Oct. 20, 2014, 14 pages.

Isner et al., "Contrasting Histoarchitecture of calcified leaflets from stenotic bicuspid versus stenotic tricuspid aortic valves," J Am Coll Cardiol., vol. 15, No. 5, p. 1104, (Apr. 1990).

Lung et al., "A Prospective Survey of Patients with Valvular Heart Disease in Europe: The Euro Heart Survey on Valvular Heart Disease," Euro Heart Journal, vol. 24, pp. 1231-1243 (2003).

McBride et al "Aortic Valve Decalcification," J Thorac Cardiovas-Surg, vol. 100, pp. 36-42 (1999).

Miller et al., "Lysis and Sonoporation of Epidermoid and Phagocytic Monolayer Cells by Diagnostic Ultrasound Activation of Contrast Agent Gas Bodies, " Ultrasound in Med. & Biol., vol. 27, No. 8, pp. 1107-1113 (2001).

Mohler, "Mechanisms of Aortic Valve Calcificaion," Am J Cardiol, vol. 94 No. 11, pp. 1396-1402, A6 (Dec. 1, 2004).

Non Final Office Action for U.S. Appl. No. 11/299,246, Mailed Apr. 7, 2009, 6 pages.

Non Final Office Action for U.S. Appl. No. 11/299,246, Mailed Oct. 16, 2008, 7 pages.

Non Final Office Action for U.S. Appl. No. 11/299,246, Mailed Aug. 22, 2007, 4 pages.

Non Final Office Action for U.S. Appl. No. 12/870,270, Mailed Nov. 18, 2011, 9 pages.

Non Final Office Action for U.S. Appl. No. 13/329,083, Mailed Jul. 25, 2013, 16 pages.

Non Final Office Action for U.S. Appl. No. 13/842,785, Mailed Feb. 3, 2014, 24 pages.

Non Final Office Action for U.S. Appl. No. 13/946,552, Mailed Feb. 3, 2014, 23 pages.

Non Final Office Action for U.S. Appl. No. 13/946,628, Mailed Feb. 4, 2014, 24 pages.

(56) References Cited

OTHER PUBLICATIONS

Non Final Office Action for U.S. Appl. No. 13/949,098, Mailed Feb. 24, 2014, 28 pages.
Notice of Allowance for U.S. Appl. No. 11/299,246, Mailed May 27, 2010, 6 pages.
Otto et al., "Three-Year Outcome After Balloon Aortic Valvuloplasty. Insights into Prognosis of Valvular Aortic Stenosis," Circulation, vol. 89, pp. 642-650.
Passik et al., "Temporal Changes in the Causes of Aortic Stenosis: A Surgical Pathologic Study of 646 Cases," Mayo Clin Proc, vol. 62, pp. 19-123 (1987).
Quaden et al., "Percutaneous Aortic Valve Replacement: Resection Before Implantation," Eur J Cardiothorac Surg, vol. 27, pp. 836-840, (2005).
Riebman et al., "New Concepts in the Management of Patients With Aortic Valve Disease." Abstract, Valvular Heart Disease, JACC, 2004, p. 34A.
Rosenschein et al., "Percutaneous Transluminal Therapy of Occluded Saphenous Vein Grafts," Circulation, vol. 99, pp. 26-29, (1999).
Sakata et al., "Percutaneous Balloon Aortic Valvuloplasty: Antegrade Transseptal vs. Conventional Retrograde Transarterial Approach," Catheter Cardiovasc Interv., vol. 64, No. 3, p. 314, (Mar. 2005).
Sasaki et al., "Scanning electron microscopy and Fourier transformed infrared spectroscopy analysis of bone removal using Er:YAG and CO2 lasers" J Periodontol.; vol. 73, No. 6, pp. 643-652. (Jun. 2002).
Van Den Brand et al., "Histological Changes in the Aortic Valve after Balloon Dilation: Evidence for a Delayed Healing Process," Br Heart J, 1992; vol. 67, pp. 445-459.
Verdaadadonk et al., "The Mechanism of Action of the Ultrasonic Tissue Resectors Disclosed Using High-Speed and Thermal Imaging Techniques," SPIE , vol. 3594, pp. 221-231 (Jan. 1999).
Voelker et al., "Inoperative Valvuloplasty in Calcific Aortic Stenosis: a Study Comparing the Mechanism of a Novel Expandable Device with conventional Balloon Dilation," Am Heart J. vol. 122 No. 5, pp. 1327-1333 (Nov. 1991).
Waller et al., "Catheter Balloon Valvuloplasty of Stenotic Aortic Valves. Part II: Balloon Valvuloplasty During Life Subsequent Tissue Examination," Clin Cardiol., vol. 14 No. 11, pp. 924-930, (Nov. 1991).
Wang, "Balloon Aortic Valvuloplasty," Prog Cardiovasc Dis., vol. 40, No. 1, pp. 27-36. (Jul.-Aug. 1997).
Wilson et al., "Elastography—The movement Begins" Phys. Med. Biol., vol. 45, pp. 1409-1421, (2000).
Yock et al, "Catheter-Based Ultrasound Thrombolysis," Circulation, vol. 95 No. 6, pp. 1411-1416 (Mar. 18, 1997).
Notice of Allowance for U.S. Appl. No. 13/949,098, mailed May 8, 2015, 7 pages.
European Search Report for European App. No. 05853460.3, completed Mar. 13, 2015, 3 pages.
Final Office Action for U.S. Appl. No. 13/842,785, mailed Jan. 5, 2015, 6 pages.
Final Office Action for U.S. Appl. No. 13/946,552, Mailed Jan. 8, 2015, 6 pages.
Final Office Action for U.S. Appl. No. 13/946,628, Mailed Jan. 5, 2015, 5 pages.
International Search Report and Written Opinion for International Application No. PCT/US2014/029549, mailed Mar. 2, 2015, 20 pages.
Non Final Office Action for U.S. Appl. No. 13/949,098, Mailed Dec. 18, 2014, 11 pages.
Notice of Allowance for U.S. Appl. No. 13/842,785, mailed Apr. 7, 2015, 8 pages.
Notice of Allowance for U.S. Appl. No. 13/946,552, mailed Mar. 25, 2015, 8 pages.
Notice of Allowance for U.S. Appl. No. 13/946,628, mailed Mar. 25, 2015, 8 pages.
BlueCross BlueShield of Northern Carolina Corporate Medical Policy "Balloon valvuloplasty, Percutaneous", (Jun. 1994).
Final Office Action mailed Jul. 15, 2014 for U.S. Appl. No. 13/949,098.
Final Office Action mailed Sep. 27, 2016 for U.S. Appl. No. 14/820,830.
Final Office Action mailed Sep. 27, 2016 for U.S. Appl. No. 14/815,651.
Non Final Office Action mailed Jul. 1, 2016 for U.S. Appl. No. 15/146,750.
Non Final Office Action mailed Jul. 5, 2016 for U.S. Appl. No. 15/146,773.
Non Final Office Action mailed Mar. 14, 2016 for U.S. Appl. No. 14/807,788.
Non Final Office Action mailed May 20, 2016 for U.S. Appl. No. 14/815,651.
Non Final Office Action mailed May 20, 2016 for U.S. Appl. No. 14/820,830.
Notice of Allowance mailed Apr. 7, 2015 for U.S. Appl. No. 13/842,785.
Notice of Allowance mailed Oct. 26, 2016 for U.S. Appl. No. 14/775,575.
Office Action dated Aug. 29, 2016 for Japanese Application No. 2014537341.
Office Action dated Feb. 23, 2011 for Japanese Application No. 2007545650.
The CoreValve System Medtronic, 2012, 4 Pages.

* cited by examiner

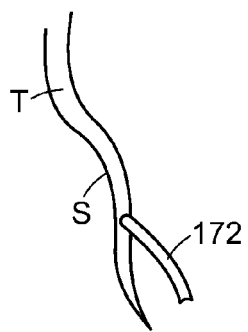
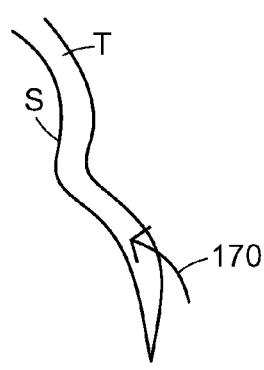
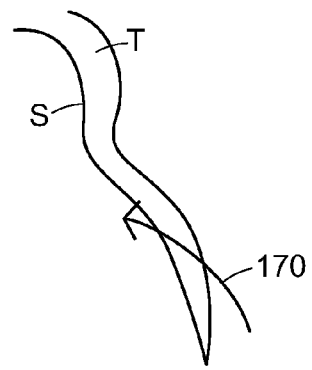
FIG. 26A　　　　FIG. 26B　　　　FIG. 26C
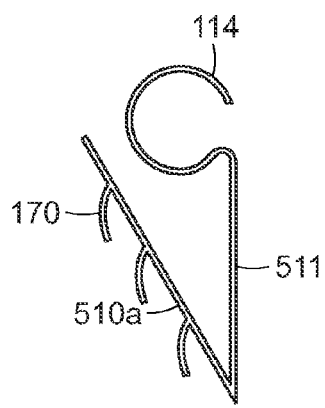
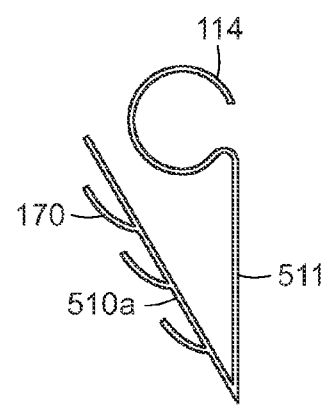
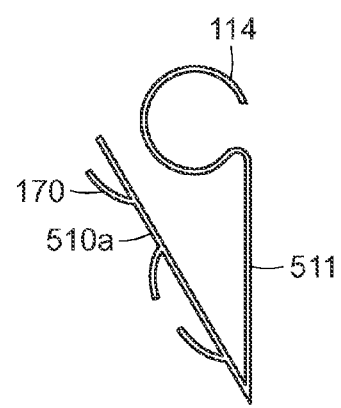
FIG. 27A　　　　FIG. 27B　　　　FIG. 27C

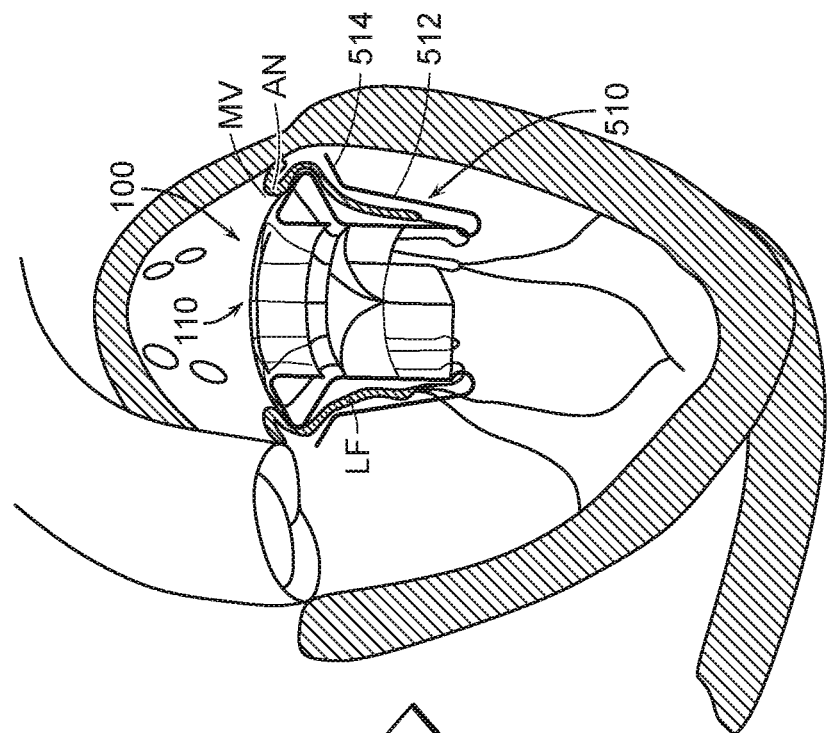
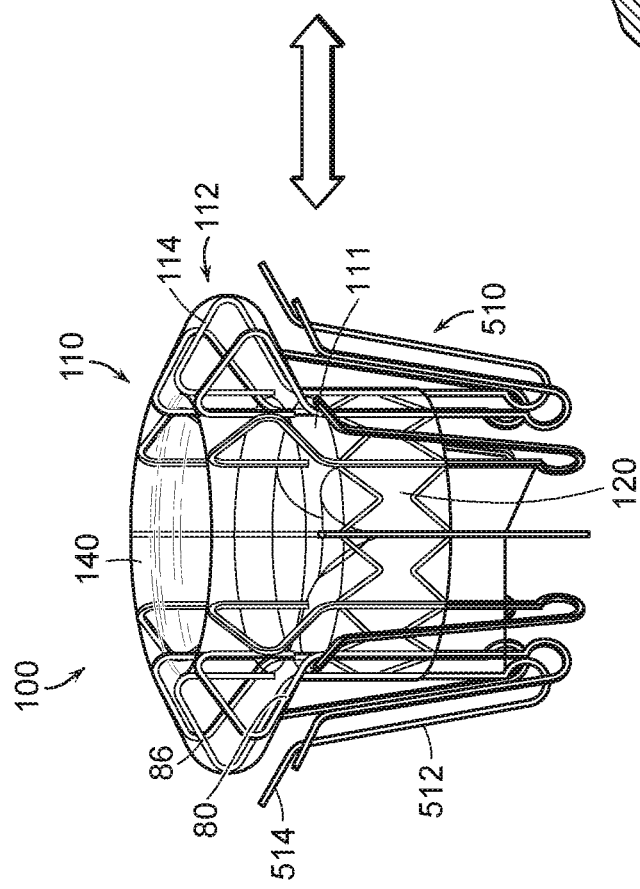
FIG. 30A
FIG. 30B

DEVICES, SYSTEMS AND METHODS FOR HEART VALVE REPLACEMENT

CROSS-REFERENCES TO RELATED APPLICATIONS

The present application is 5 U.S.C. 371 of International Application No. PCT/US12/61215, filed Oct. 19, 2012 entitled "DEVICES, SYSTEMS, AND METHODS FOR HEART VALVE REPLACEMENT," and claims priority to U.S. Provisional Patent Application No. 61/549,037, filed Oct. 19, 2011 entitled "SYSTEM FOR MITRAL VALVE REPLACEMENT," both of which are incorporated herein by reference in their entirety.

The present application also incorporates the subject matter of (1) International Patent Application No. PCT/US2012/043636, entitled "PROSTHETIC HEART VALVE DEVICES AND ASSOCIATED SYSTEMS AND METHODS," filed Jun. 21, 2012; (2) U.S. Provisional Patent Application No. 61/605,699, filed Mar. 1, 2012, entitled "SYSTEM FOR MITRAL VALVE REPLACEMENT"; (3) U.S. Provisional Patent Application No. 61/549,044, filed Oct. 19, 2011, and entitled "CONFORMABLE SYSTEM FOR MITRAL VALVE REPLACEMENT"; and (4) International Patent Application No. PCT/US2012/061219, entitled "PROSTHETIC HEART VALVE DEVICES, PROSTHETIC MITRAL VALVES AND ASSOCIATED SYSTEMS AND METHODS," filed Oct. 19, 2012, in their entireties by reference.

TECHNICAL FIELD

The present technology relates generally to prosthetic heart valve devices. In particular, several embodiments are directed to prosthetic mitral valves and devices for percutaneous repair and/or replacement of native heart valves and associated systems and methods.

BACKGROUND

Conditions affecting the proper functioning of the mitral valve include, for example, mitral valve regurgitation, mitral valve prolapse and mitral valve stenosis. Mitral valve regurgitation is a disorder of the heart in which the leaflets of the mitral valve fail to coapt into apposition at peak contraction pressures, resulting in abnormal leaking of blood from the left ventricle into the left atrium. There are a number of structural factors that may affect the proper closure of the mitral valve leaflets. For example, many patients suffering from heart disease experience dilation of the heart muscle, resulting in an enlarged mitral annulus. Enlargement of the mitral annulus makes it difficult for the leaflets to coapt during systole. A stretch or tear in the chordae tendineae, the tendons connecting the papillary muscles to the inferior side of the mitral valve leaflets, may also affect proper closure of the mitral annulus. A ruptured chordae tendineae, for example, may cause a valve leaflet to prolapse into the left atrium due to inadequate tension on the leaflet. Abnormal backflow can also occur when the functioning of the papillary muscles is compromised, for example, due to ischemia. As the left ventricle contracts during systole, the affected papillary muscles do not contract sufficiently to effect proper closure.

Mitral valve prolapse, or when the mitral leaflets bulge abnormally up in to the left atrium, causes irregular behavior of the mitral valve and may also lead to mitral valve regurgitation. Normal functioning of the mitral valve may also be affected by mitral valve stenosis, or a narrowing of the mitral valve orifice, which causes impedance of filling of the left ventricle in diastole.

Typically, treatment for mitral valve regurgitation has involved the application of diuretics and/or vasodilators to reduce the amount of blood flowing back into the left atrium. Other procedures have involved surgical approaches (open and intravascular) for either the repair or replacement of the valve. For example, typical repair approaches have involved cinching or resecting portions of the dilated annulus.

Cinching of the annulus has been accomplished by the implantation of annular or peri-annular rings which are generally secured to the annulus or surrounding tissue. Other repair procedures have also involved suturing or clipping of the valve leaflets into partial apposition with one another.

Alternatively, more invasive procedures have involved the replacement of the entire valve itself where mechanical valves or biological tissue are implanted into the heart in place of the mitral valve. These are conventionally done through large open thoracotomies and are thus very painful, have significant morbidity, and require long recovery periods.

However, with many repair and replacement procedures the durability of the devices or improper sizing of annuloplasty rings or replacement valves may result in additional problems for the patient. Moreover, many of the repair procedures are highly dependent upon the skill of the cardiac surgeon where poorly or inaccurately placed sutures may affect the success of procedures.

Less invasive approaches to aortic valve replacement have been developed in recent years. Examples of pre-assembled, percutaneous prosthetic valves include, e.g., the CoreValve Revalving® System from Medtronic/Corevalve Inc. (Irvine, Calif., USA) the Edwards-Sapien® Valve from Edwards Lifesciences (Irvine, Calif., USA). Both valve systems include an expandable frame housing a tri-leaflet bioprosthetic valve. The frame is expanded to fit the substantially symmetric circular aortic valve. This gives the expandable frame in the delivery configuration a symmetric, circular shape at the aortic valve annulus, perfectly functional to support a tri-leaflet prosthetic valve (which requires such symmetry for proper coaptation of the prosthetic leaflets). Thus, aortic valve anatomy lends itself to an expandable frame housing a replacement valve since the aortic valve anatomy is substantially uniform and symmetric. The mitral valve, on the other hand, is generally D-shaped and not symmetric, meaning that expansion of the CoreValve and Sapien systems in the mitral valve renders such systems non-functional. For example, in both systems the frame both anchors (or helps to anchor) and provides shape to the replacement valve within. If the frame is flexible enough to assume the asymmetric shape of the mitral valve, then the attached tri-leaflet replacement valve will also be similarly shaped, making it almost impossible for the leaflets to coapt properly and thus allowing leaks. Additionally, if the frame is so rigid that it remains symmetric, the outer diameter of the frame will not be able to cover the commissures of the mitral valve, also allowing leaks.

In addition, mitral valve replacement, compared with aortic valve replacement, poses unique anatomical obstacles, rendering percutaneous mitral valve replacement significantly more involved and challenging than aortic valve replacement. First, unlike the relatively symmetric and uniform aortic valve, the mitral valve annulus has a non-circular D-shape or kidney-like shape and may be of unpredictable geometry, often times lacking symmetry. Such unpredictability makes it difficult to design a mitral valve prosthesis having the ability to conform to the mitral annulus. Lack of a snug fit between the leaflets and/or annulus and the prosthesis leaves gaps therein, creating backflow of blood through these gaps. Placement of a cylindrical valve prosthesis, for example, may leave gaps in commissural regions of the native valve, potentially resulting in perivalvular leaks in those regions.

Current devices seeking to overcome the large and irregular shape of the mitral valve have several drawbacks. First, many of the devices today have a direct, structural connection between the device structure which contacts the annulus and/or leaflets and the device structure which supports the prosthetic valve. In several devices, the same stent posts which support the prosthetic valve also contact subannular tissue, directly transferring many of the distorting forces present in the heart, for example, systolic pressure, diastolic pressure, compressive intra-annular forces, etc., causing hoop stress in the stent portion surrounding the prosthetic valve. Most cardiac replacement devices utilize a tri-leaflet valve, which requires a substantially symmetric, cylindrical support around the prosthetic valve for proper opening and closing of the three leaflets. Devices which provide a direct, mechanical connection between annular and/or leaflet distorting forces and the prosthetic valve may compress and/or distort the symmetrical, cylindrical structure surrounding the prosthetic valve causing the prosthetic leaflets to malfunction.

In addition to its irregular, unpredictable shape, the mitral valve annulus lacks a significant amount of radial support from surrounding tissue. The aortic valve, for example, is completely surrounded by fibro-elastic tissue, helping to anchor a prosthetic valve by providing native structural support. The mitral valve, on the other hand, is bound by muscular tissue on the outer wall only. The inner wall of the mitral valve is bound by a thin vessel wall separating the mitral valve annulus from the inferior portion of the aortic outflow tract. As a result, significant radial forces on the mitral annulus, such as that imparted by expanding stent prostheses, could lead to collapse of the inferior portion of the aortic tract with potentially fatal consequences.

The chordae tendineae of the left ventricle may also present an obstacle in deploying a mitral valve prosthesis. This is unique to the mitral valve since aortic valve anatomy does not include chordae. The maze of chordae in the left ventricle makes navigating and positioning a deployment catheter more difficult in mitral valve replacement and repair. Deployment and positioning of a prosthetic valve or anchoring device on the ventricular side of the native valve is also complicated by the presence of the chordae.

Given the difficulties associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 26A-26C are schematic views illustrating various embodiments of tissue engaging elements for use with prosthetic heart valve devices in accordance with the present technology.

FIGS. 27A-27C are enlarged, partial side views of a prosthetic heart valve device having arms with tissue engaging elements configured to engage an inward-facing surface of the leaflets in accordance with various embodiments of the present technology.

FIGS. 30A and 30C are isometric views of the prosthetic heart valve device having arms with a similar profile as a profile of the retainer in accordance with additional embodiments of the present technology.

FIGS. 30B and 30D are side views of the prosthetic heart valve devices of FIGS. 30A and 30C, respectively, and shown implanted at a mitral valve (illustrated in cross-section) in accordance with the present technology.

FIGS. 32A-32D are schematic top views of arm location patterns in accordance with additional embodiments of the present technology.

FIGS. 33E-33G are enlarged side views of tissue engaging elements suitable for use with prosthetic heart valve devices in accordance with other embodiments of the present technology.

DETAILED DESCRIPTION

Figure 1:
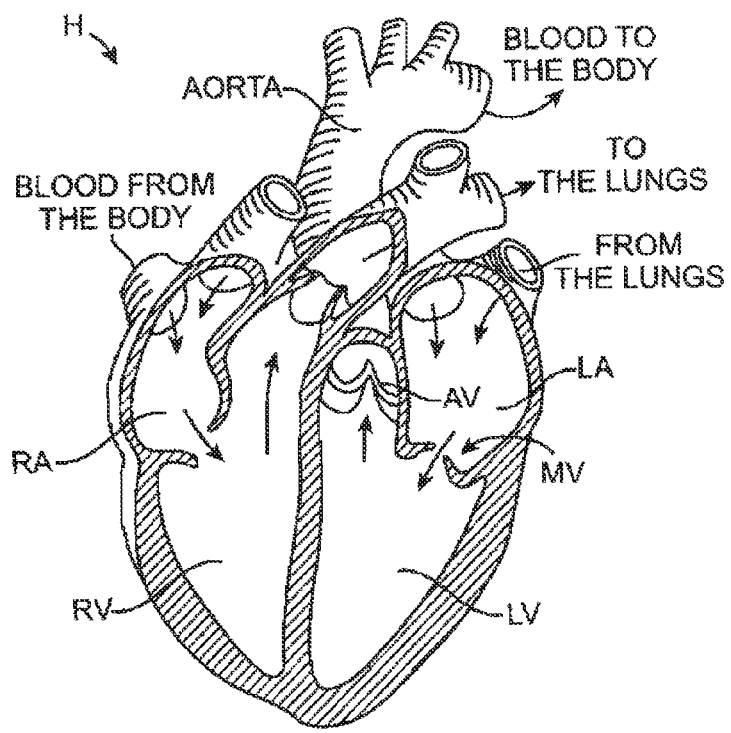
FIGS. 1 and 2 are schematic illustrations of a mammalian heart having native valve structures suitable for replacement with various prosthetic heart valve devices in accordance with embodiments of the present technology.

Specific details of several embodiments of the technology are described below with reference to FIGS. 1-40C. Although many of the embodiments are described below with respect to devices, systems, and methods for percutaneous replacement of a native mitral valve using prosthetic valve devices, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-40C.

With regard to the terms "distal" and "proximal" within this description, unless otherwise specified, the terms can reference a relative position of the portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow. For ease of reference, throughout this disclosure identical reference numbers and/or letters are used to identify similar or analogous components or features, but the use of the same reference number does not imply that the parts should be construed to be identical. Indeed, in many examples described herein, the identically numbered parts are distinct in structure and/or function. The headings provided herein are for convenience only.

Overview

Systems, devices and methods are provided herein for percutaneous replacement of native heart valves, such as mitral valves. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Embodiments of the present technology provide systems, methods and apparatus to treat valves of the body, such as heart valves including the mitral valve. The apparatus and methods enable a percutaneous approach using a catheter delivered intravascularly through a vein or artery into the heart. Additionally, the apparatus and methods enable other less-invasive approaches including trans-apical, trans-atrial, and direct aortic delivery of a prosthetic replacement valve to a target location in the heart. The apparatus and methods enable a prosthetic device to be anchored at a native valve location by engagement with a subannular surface of the valve annulus and/or valve leaflets. Additionally, the embodiments of the devices and methods as described herein can be combined with many known surgeries and procedures, for example combined with known methods of accessing the valves of the heart such as the mitral valve or tricuspid valve with antegrade or retrograde approaches, and combinations thereof.

The devices and methods described herein provide a valve replacement device that has the flexibility to adapt and conform to the variably-shaped native mitral valve anatomy while mechanically isolating the prosthetic valve from the anchoring portion of the device, which can absorb the distorting forces applied by the native anatomy. The device has the structural strength and integrity necessary to withstand the dynamic conditions of the heart over time, thus permanently anchoring a replacement valve and making it possible for the patient to resume a substantially normal life. The devices and methods further deliver such a device in a less-invasive manner, providing a patient with a new, permanent replacement valve but also with a lower-risk procedure and a faster recovery.

The devices and methods described herein provide a valve replacement device that has the flexibility to adapt and conform to the variably-shaped native mitral valve anatomy while simultaneously providing the structural strength and integrity necessary to withstand the dynamic conditions of the heart over time, thus permanently anchoring a replacement valve, making it possible for the patient to resume a substantially normal life. The devices and methods further deliver such a device in a less-invasive manner, providing a patient with a new, permanent replacement valve but also with a lower-risk procedure and a faster recovery.

In accordance with various embodiments of the present technology, a device for repair or replacement of a native heart valve, wherein the native heart valve has an annulus and leaflets coupled to the annulus is disclosed. The device can include a valve support having an upstream end and a downstream end extending around a longitudinal axis, and have an outer surface and an inner surface. The valve support can have a cross-sectional shape and the inner surface can be configured to support a prosthetic valve. The device can also include an expandable retainer that is couple dot the upstream end of the valve support. The retainer can be configured to engage tissue on or downstream of the annulus. In various embodiments, the valve support is mechanically isolated from the retainer such that the cross-sectional shape of the valve support remains sufficiently stable when the retainer is deformed in a non-circular shape by engagement with the tissue.

Some embodiments of the disclosure are directed to prosthetic heart valve devices for treating a mitral valve. The device can include a valve support configured to support a valve. The device can also include a retainer coupled to the valve support and positionable at least partially along a subannular surface of a native mitral valve annulus. The retainer can also inhibit upstream migration of the device. The retainer is coupled to the valve support so as to mechanically isolate the valve support from distorting force exerted on the retainer by native anatomy.

In some embodiments, the device may comprise an atrial extension member extending from the retainer to a position at least partially upstream of the native mitral annulus. In other embodiments, the device may further comprise a plurality of arms extending radially outward from the valve support. The arms can be configured to engage native leaflets of the mitral valve, for example. Some embodiments of the device may further comprise one or more stabilizing members for engaging subannular tissue and limiting movement of the device in an upstream or downstream direction.

In a further embodiment, a prosthetic heart valve device for treating a mitral valve can include an expandable retainer configured to engage cardiac tissue at or downstream of a native mitral valve annulus. The device can also include a valve support coupled to and at least partially surrounded by the expandable retainer. The valve support can be configured to support a prosthetic valve such as either a temporary valve, or in other embodiments, a permanent valve structure. In these arrangements, the expandable retainer is configured to conform to the shape of the native mitral valve annulus while the valve support remains substantially unchanged.

In yet a further embodiment, a prosthetic heart valve device for treating a heart valve in a patient can include a valve support having a generally circular shape and configured to support a prosthetic valve, and a deformable retainer coupled to an upstream portion of the valve support. The deformable retainer can be configured to engage cardiac tissue on or below an annulus of the heart valve. The valve support can be mechanically isolated from the retainer such that deformation of the retainer does not substantially affect the generally circular shape of the valve support. The device may also include a plurality of arms coupled to a downstream portion of the valve support. The arms can be biased outward from the valve support in an unbiased configuration such that the plurality of arms can be configured to engage a native mitral leaflet.

The disclosure further provides systems for delivery of prosthetic valves and other devices using endovascular or other minimally invasive forms of access. For example, embodiments of the present technology provide a system to treat a mitral valve of a patient, in which the mitral valve has an annulus. The system comprises a device to treat the mitral valve as described herein and a catheter having a lumen configured to retain the device within the catheter.

In yet another aspect, embodiments of the present technology provide a method of treating a heart valve of a patient. The mitral valve has an annulus and leaflets coupled to the annulus. The method can include implanting a device as described herein within or adjacent to the annulus. The device, in some embodiments, can include a valve support coupled to and at least partially surrounded by a deformable retainer. The deformable retainer can be coupled to an upstream end of the valve support. The deformable retainer can be disposed between the leaflets and be configured to engage tissue on or near the annulus to prevent migration of the device in an upstream direction. Further, the valve support can be mechanically isolated from the deformable retainer such that a cross-sectional shape of the valve support does not substantially change if the retainer is deformed by engagement with the tissue.

In yet a further aspect, embodiments of the present technology provide a method for replacement of a native heart valve having an annulus and a plurality of leaflets. The method can include positioning a prosthetic device as described herein between the leaflets, while the device is in a collapsed configuration. The method can also include allowing the prosthetic device to expand such that a retainer of the prosthetic device is in a subannular position in which it engages tissue on or downstream of the annulus. The retainer can have a diameter larger than a corresponding diameter of the annulus in the subannular position. The method can further include allowing a valve support to expand within the retainer, wherein the valve support is coupled to the retainer at an upstream end of the valve support. In various embodiments, the valve support can be mechanically isolated from the retainer such that deformation of the retainer when the retainer engages the tissue does not substantially deform the valve support.

The devices and methods disclosed herein can be configured for treating non-circular, asymmetrically shaped valves and bileaflet or bicuspid valves, such as the mitral valve. Many of the devices and methods disclosed herein can further provide for long-term (e.g., permanent) and reliable anchoring of the prosthetic device even in conditions where the heart or native valve may experience gradual enlargement or distortion.

Cardiac and Mitral Valve Physiology

Figure 2:
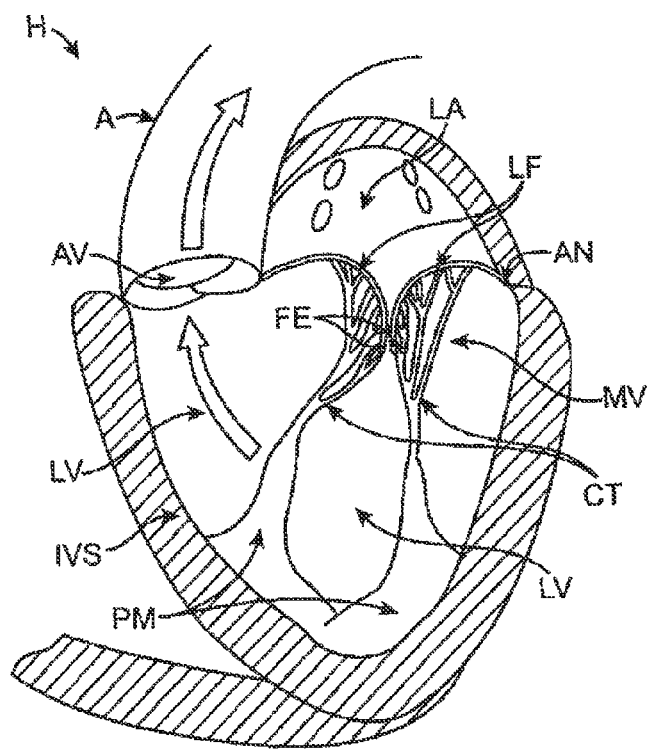

FIGS. 1 and 2 show a normal heart H. The heart comprises a left atrium that receives oxygenated blood from the lungs via the pulmonary veins PV and pumps this oxygenated blood through the mitral valve MV into the left ventricle LV. The left ventricle LV of a normal heart H in systole is illustrated in FIG. 2. The left ventricle LV is contracting and blood flows outwardly through the aortic valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA.

Figure 3:
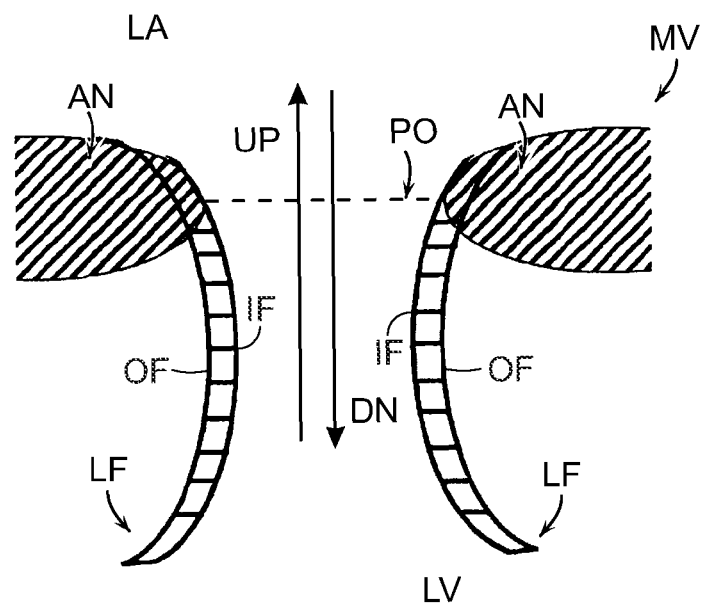
FIG. 3 is a schematic cross-sectional side view of a native mitral valve showing the annulus and leaflets.

The mitral valve MV comprises a pair of leaflets having free edges FE which meet evenly, or "coapt" to close, as illustrated in FIG. 2. The opposite ends of the leaflets LF are attached to the surrounding heart structure via an annular region of tissue referred to as the annulus AN. FIG. 3 is a schematic cross-sectional side view of an annulus and leaflets of a mitral valve. As illustrated, the opposite ends of the leaflets LF are attached to the surrounding heart structure via a fibrous ring of dense connective tissue referred to as the annulus AN, which is distinct from both the leaflet tissue LF as well as the adjoining muscular tissue of the heart wall. The leaflets LF and annulus AN are comprised of different types of cardiac tissue having varying strength, toughness, fibrosity, and flexibility. Furthermore, the mitral valve MV may also comprise a unique region of tissue interconnecting each leaflet LF to the annulus AN, referred to herein as leaflet/annulus connecting tissue LAC (indicated by overlapping cross-hatching). In general, annular tissue AN is tougher, more fibrous, and stronger than leaflet tissue LF.

Referring to FIG. 2, the free edges FE of the mitral leaflets LF are secured to the lower portions of the left ventricle LV through chordae tendineae CT (referred to hereinafter "chordae") which include a plurality of branching tendons secured over the lower surfaces of each of the valve leaflets LF. The chordae CT in turn, are attached to the papillary muscles PM, which extend upwardly from the lower wall of the left ventricle LV and interventricular septum IVS.

Figure 4A:
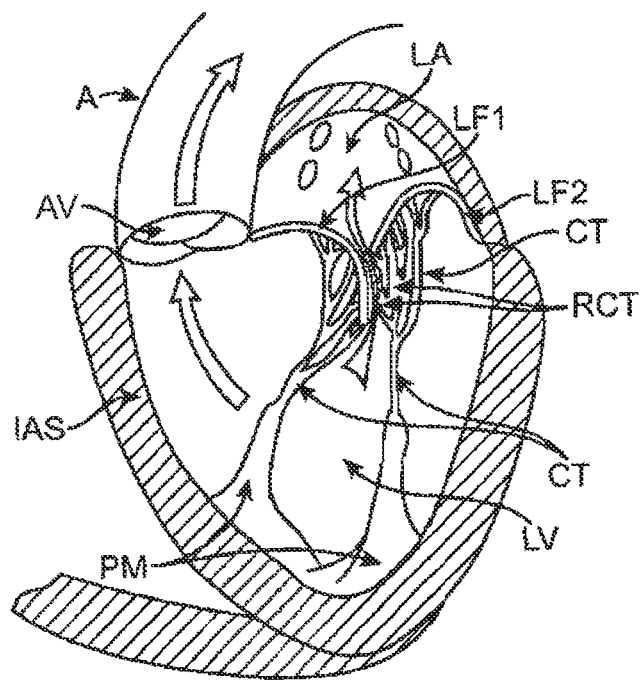
FIG. 4A is a schematic illustration of the left ventricle of a heart having either i) prolapsed leaflets in the mitral valve, or ii) mitral valve regurgitation in the left ventricle of a heart having impaired papillary muscles, and which are suitable for combination with various prosthetic heart valve devices in accordance with embodiments of the present technology.
Figure 4B:
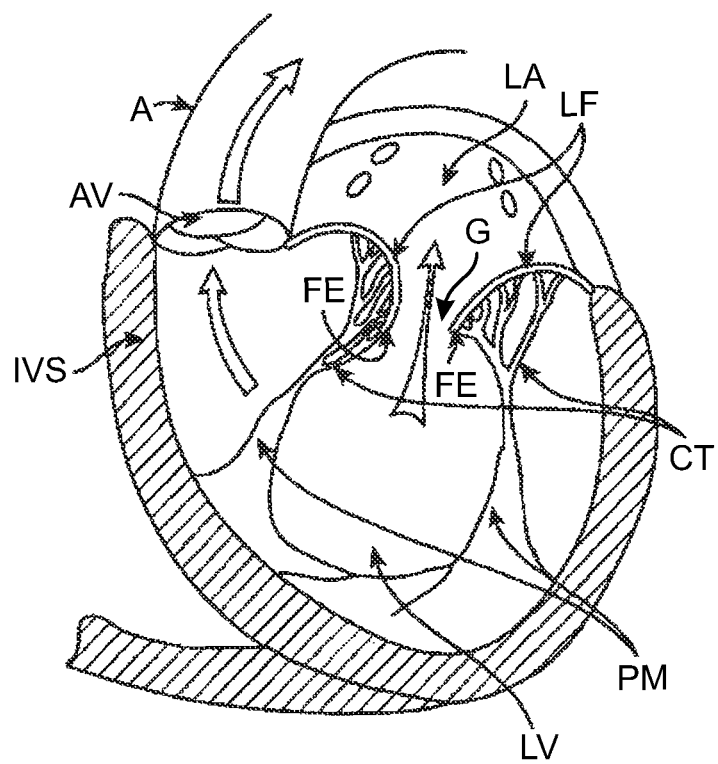
FIG. 4B is a schematic illustration of a heart in a patient suffering from cardiomyopathy, and which is suitable for combination with various prosthetic heart valve devices in accordance with embodiments of the present technology.

Referring now to FIGS. 4A to 4B, a number of structural defects in the heart can cause mitral valve regurgitation. Ruptured chordae RCT, as shown in FIG. 4A, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Regurgitation also occurs in the patients suffering from cardiomyopathy where the heart is dilated and the increased size prevents the valve leaflets LF from meeting properly, as shown in FIG. 4B. The enlargement of the heart causes the mitral annulus to become enlarged, making it impossible for the free edges FE to meet during systole. The free edges of the anterior and posterior leaflets normally meet along a line of coaptation C as shown in FIG. 5A, but a significant gap G can be left in patients suffering from cardiomyopathy, as shown in FIG. 5B.

Mitral valve regurgitation can also occur in patients who have suffered ischemic heart disease where the functioning of the papillary muscles PM is impaired, as illustrated in FIG. 4A. As the left ventricle LV contracts during systole, the papillary muscles PM do not contract sufficiently to effect proper closure. One or both of the leaflets LF1 and LF2 then prolapse. Leakage again occurs from the left ventricle LV to the left atrium LA.

Figure 5A:
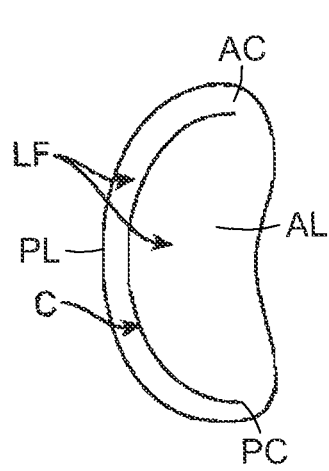
FIG. 5A is a schematic illustration of a native mitral valve of a heart showing normal closure of native mitral valve leaflets.
Figure 5B:
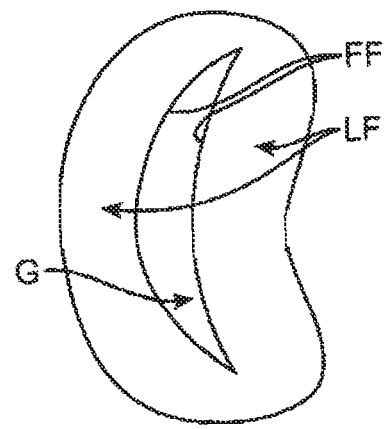
FIG. 5B is a schematic illustration of a native mitral valve of a heart showing abnormal closure of native mitral valve leaflets in a dilated heart, and which is suitable for combination with various prosthetic heart valve devices in accordance with embodiments of the present technology.
Figure 5C:
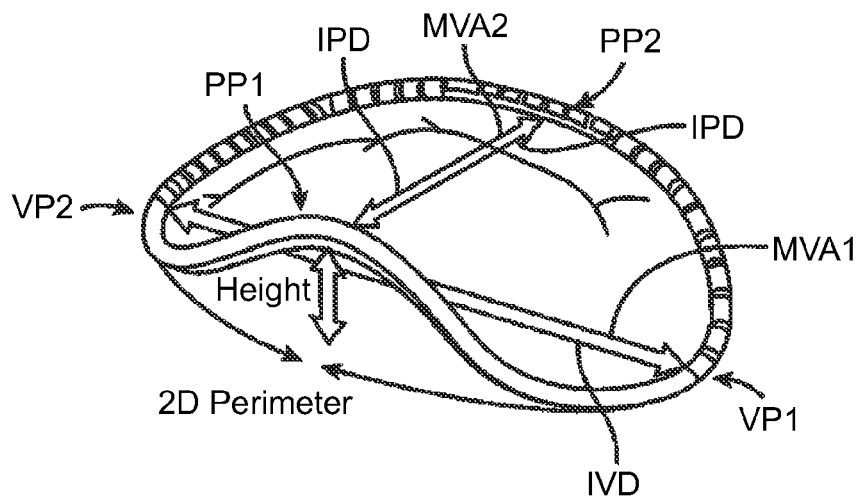
FIG. 5C is a schematic illustration of a mitral valve of a heart showing dimensions of the annulus, and which is suitable for combination with various prosthetic heart valve devices in accordance with embodiments of the present technology.

FIGS. 5A-5C further illustrate the shape and relative sizes of the leaflets L of the mitral valve. Referring to FIG. 5C, it may be seen that the overall valve has a generally "D"- or kidney-like shape, with a long axis MVA1 and a short axis MVA2. In healthy humans the long axis MVA1 is typically within a range from about 33.3 mm to about 42.5 mm in length (37.9+/−4.6 mm), and the short axis MVA2 is within a range from about 26.9 to about 38.1 mm in length (32.5+/−5.6 mm). However, with patients having decreased cardiac function these values can be larger, for example MVA1 can be within a range from about 45 mm to 55 mm and MVA2 can be within a range from about 35 mm to about 40 mm. The line of coaptation C is curved or C-shaped, thereby defining a relatively large anterior leaflet AL and substantially smaller posterior leaflet PL (FIG. 5A). Both leaflets appear generally crescent-shaped from the superior or atrial side, with the anterior leaflet AL being substantially wider in the middle of the valve than the posterior leaflet. As illustrated in FIG. 5A, at the opposing ends of the line of coaptation C the leaflets join together at corners called the anterolateral commissure AC and posteromedial commissure PC, respectively.

FIG. 5C shows the shape and dimensions of the annulus of the mitral valve. The annulus is an annular area around the circumference of the valve comprised of fibrous tissue which is thicker and tougher than that of the leaflets LF and distinct from the muscular tissue of the ventricular and atrial walls. The annulus may comprise a saddle-like shape with a first peak portion PP1 and a second peak portion PP2 located along an interpeak axis IPD, and a first valley portion VP1 and a second valley portion VP2 located along an intervalley axis IVD. The first and second peak portion PP1 and PP2 are higher in elevation relative to a plane containing the nadirs of the two valley portions VP1, VP2, typically being about 8-19 mm higher in humans, thus giving the valve an overall saddle-like shape. The distance between the first and second peak portions PP1, PP2, referred to as interpeak span IPD, is substantially shorter than the intervalley span IVD, the distance between first and second valley portions VP1, VP2.

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, work in relation to embodiments suggests that some patients may have a long dimension across the annulus and a short dimension across the annulus without well-defined peak and valley portions, and the methods and device as described herein can be configured accordingly.

Access to the Mitral Valve

Access to the mitral valve or other atrioventricular valve can be accomplished through the patient's vasculature in a percutaneous manner. By percutaneous it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well-known and described in the patent and medical literature. Depending on the point of vascular access, the approach to the mitral valve may be antegrade and may rely on entry into the left atrium by crossing the inter-atrial septum. Alternatively, approach to the mitral valve can be retrograde where the left ventricle is entered through the aortic valve. Once percutaneous access is achieved, the interventional tools and supporting catheter(s) may be advanced to the heart intravascularly and positioned adjacent the target cardiac valve in a variety of manners, as described herein.

Using a trans-septal approach, access is obtained via the inferior vena cava IVC or superior vena cava SVC, through the right atrium RA, across the inter-atrial septum IAS and into the left atrium LA above the mitral valve MV.

Figure 6A:
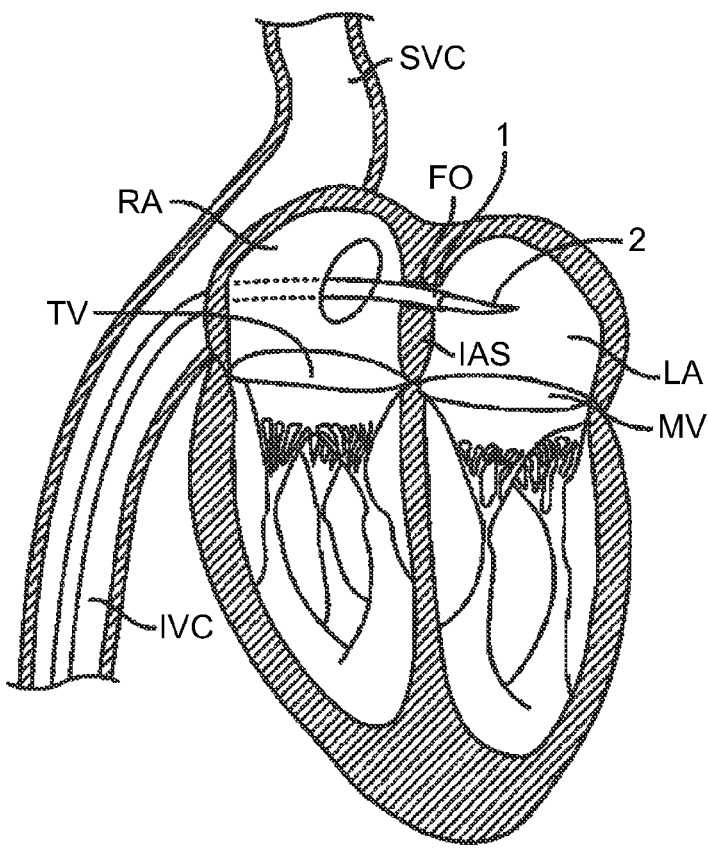
FIG. 6A is a schematic, cross-sectional illustration of the heart showing an antegrade approach to the native mitral valve from the venous vasculature in accordance with various embodiments of the present technology.

As shown in FIG. 6A, a catheter 1 having a needle 2 may be advanced from the inferior vena cava IVC into the right atrium RA. Once the catheter 1 reaches the anterior side of the inter-atrial septum IAS, the needle 2 may be advanced so that it penetrates through the septum, for example at the fossa ovalis FO or the foramen ovate into the left atrium LA. At this point, a guidewire may be exchanged for the needle 2 and the catheter 1 withdrawn.

Figure 6B:
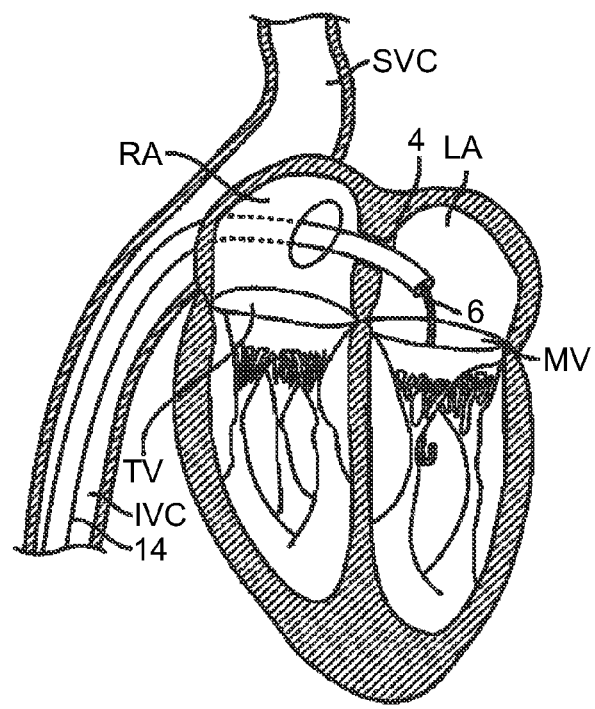
FIG. 6B is a schematic, cross-sectional illustration of the heart showing access through the inter-atrial septum (IAS) maintained by the placement of a guide catheter over a guidewire in accordance with various embodiments of the present technology.

As shown in FIG. 6B, access through the inter-atrial septum IAS may usually be maintained by the placement of a guide catheter 4, typically over a guidewire 6 which has been placed as described above. The guide catheter 4 affords subsequent access to permit introduction of the device to replace the mitral valve, as described in more detail herein.

In an alternative antegrade approach (not shown), surgical access may be obtained through an intercostal incision, preferably without removing ribs, and a small puncture or incision may be made in the left atrial wall. A guide catheter may then be placed through this puncture or incision directly into the left atrium, sealed by a purse-string suture.

The antegrade or trans-septal approach to the mitral valve, as described above, can be advantageous in many respects. For example, the use of the antegrade approach will usually allow for more precise and effective centering and stabilization of the guide catheter and/or prosthetic valve device. Precise positioning facilitates accuracy in the placement of the prosthetic valve device. The antegrade approach may also reduce the risk of damaging the subvalvular device during catheter and interventional tool introduction and manipulation. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 7:
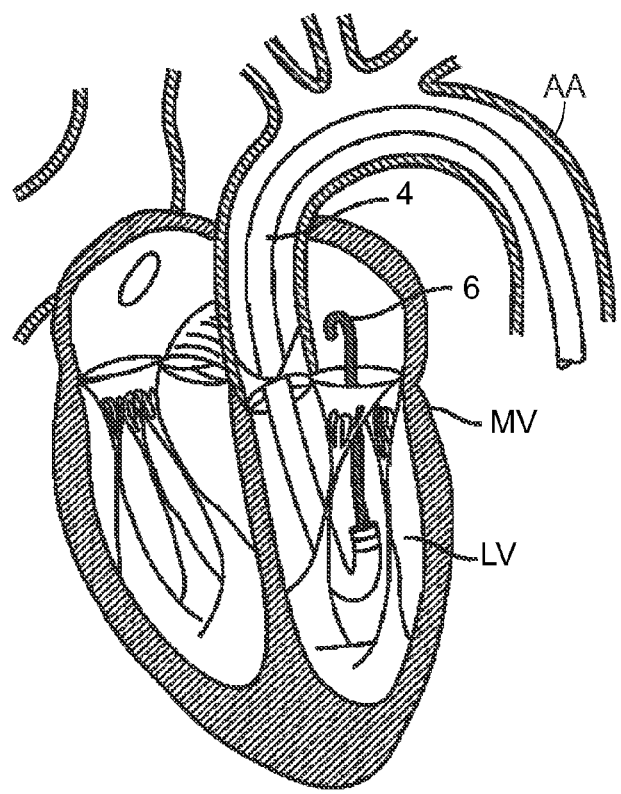
FIGS. 7 and 8 are schematic, cross-sectional illustrations of the heart showing retrograde approaches to the native mitral valve through the aortic valve and arterial vasculature in accordance with various embodiments of the present technology.
Figure 8:
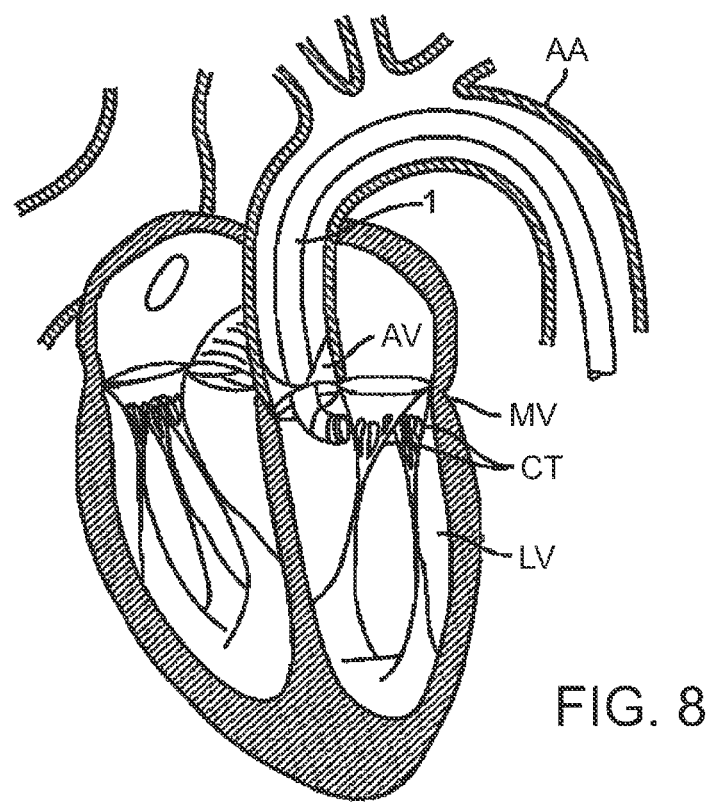

An example of a retrograde approach to the mitral valve is illustrated in FIGS. 7 and 8. The mitral valve MV may be accessed by an approach from the aortic arch AA, across the aortic valve AV, and into the left ventricle LV below the mitral valve MV. The aortic arch AA may be accessed through a conventional femoral artery access route, as well as through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein.

In some specific instances, a retrograde arterial approach to the mitral valve may be chosen due to certain advantages. For example, use of the retrograde approach can eliminate the need for a trans-septal puncture. The retrograde approach is also more commonly used by cardiologists and thus has the advantage of familiarity.

Figure 9:
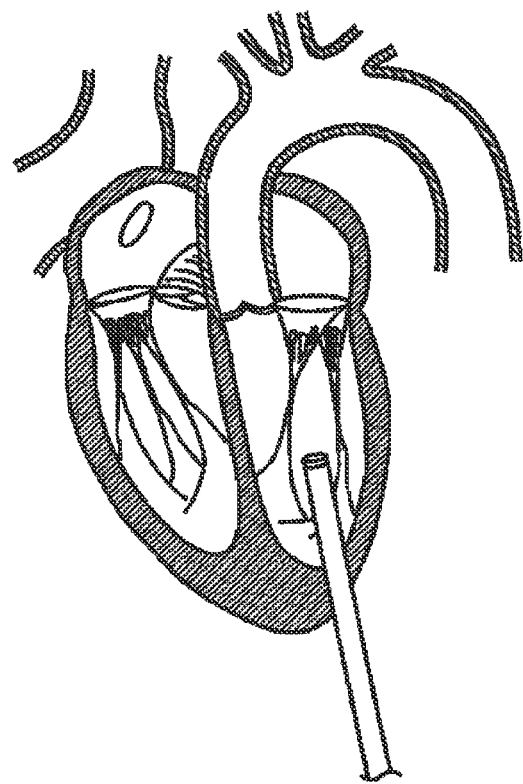
FIG. 9 is a schematic, cross-sectional illustration of the heart showing an approach to the native mitral valve using a trans-apical puncture in accordance with various embodiments of the present technology.

An additional approach to the mitral valve is via trans-apical puncture, as shown in FIG. 9. In this approach, access to the heart is gained via thoracic incision, which can be a conventional open thoracotomy or sternotomy, or a smaller intercostal or sub-xyphoid incision or puncture. An access cannula is then placed through a puncture, sealed by a purse-string suture, in the wall of the left ventricle at or near the apex of the heart. The catheters and prosthetic devices of the invention may then be introduced into the left ventricle through this access cannula.

The trans-apical approach has the feature of providing a shorter, straighter, and more direct path to the mitral or aortic valve. Further, because it does not involve intravascular access, the trans-apical procedure can be performed by surgeons who may not have the necessary training in interventional cardiology to perform the catheterizations required in other percutaneous approaches.

The prosthetic treatment device may be specifically designed for the approach or interchangeable among approaches. A person of ordinary skill in the art can identify an appropriate approach for an individual patient and design the treatment apparatus for the identified approach in accordance with embodiments described herein.

Orientation and steering of the prosthetic valve device can be combined with many known catheters, tools and devices. Such orientation may be accomplished by gross steering of the device to the desired location and then refined steering of the device components to achieve a desired result.

Gross steering may be accomplished by a number of methods. A steerable guidewire may be used to introduce a guide catheter and the prosthetic treatment device into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

A guide catheter may be pre-shaped to provide a desired orientation relative to the mitral valve. For access via the trans-septal approach, the guide catheter may have a curved, angled or other suitable shape at its tip to orient the distal end toward the mitral valve from the location of the septal puncture through which the guide catheter extends. For the retrograde approach, as shown in FIGS. 7 and 8, guide catheter 4 may have a pre-shaped J-tip which is configured so that it turns toward the mitral valve MV after it is placed over the aortic arch AA and through the aortic valve AV. As shown in FIG. 7, the guide catheter 4 may be configured to extend down into the left ventricle LV and to assume a J-shaped configuration so that the orientation of an interventional tool or catheter is more closely aligned with the axis of the mitral valve MV. In either case, a pre-shaped guide catheter may be configured to be straightened for endovascular delivery by means of a stylet or stiff guidewire which is passed through a lumen of the guide catheter. The guide catheter might also have pull-wires or other means to adjust its shape for more fine steering adjustment.

Selected Embodiments of Prosthetic Heart Valve Devices and Methods

Embodiments of the present technology as described herein can be used to treat one or more of the valves of the heart as described herein, and in particular embodiments, can be used for treatment of the mitral valve. Examples of prosthetic heart valve devices, system components and associated methods in accordance with embodiments of the present technology are described in this section with reference to FIGS. 10A-40C. It will be appreciated that specific elements, substructures, advantages, uses, and/or other features of the embodiments described with reference to FIGS. 10A-40C can be suitably interchanged, substituted or otherwise configured with one another in accordance with additional embodiments of the present technology. Furthermore, suitable elements of the embodiments described with reference to FIGS. 10A-40C can be used as stand-alone and/or self-contained devices.

Figure 10A:
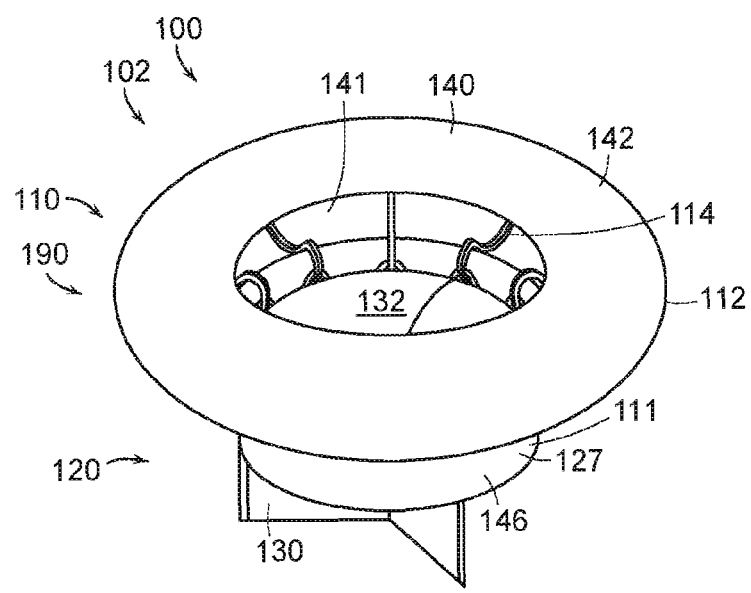
FIG. 10A shows an isometric view of a prosthetic heart valve device in accordance with an embodiment of the present technology.
Figure 10B:
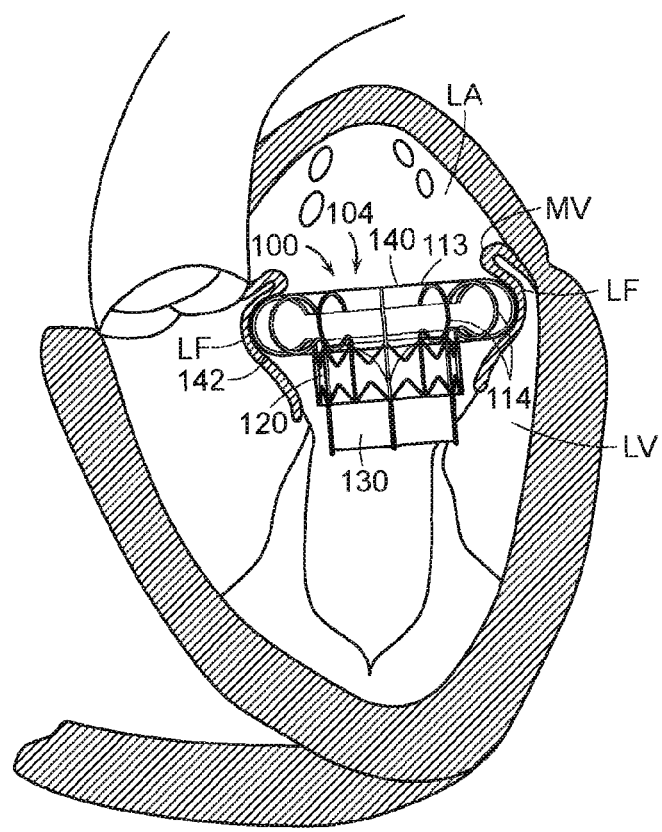
FIG. 10B illustrates a cut-away view of a heart showing the prosthetic heart valve device of FIG. 10A implanted at a native mitral valve in accordance with an embodiment of the present technology.

Systems, devices and methods are provided herein for percutaneous implantation of prosthetic heart valves in a heart of a patient. In some embodiments, methods and devices are presented for the treatment of valve disease by minimally invasive implantation of artificial replacement heart valves. In one embodiment, the artificial replacement valve can be a prosthetic valve device suitable for implantation and replacement of a mitral valve between the left atrium and left ventricle in the heart of a patient. In another embodiment, the prosthetic valve device can be suitable for implantation and replacement of another valve (e.g., a bicuspid or tricuspid valve) in the heart of the patient. FIG. 10A shows an isometric view of a prosthetic heart valve device 100 in an expanded configuration 102 in accordance with an embodiment of the present technology, and FIG. 10B is a schematic illustration of a cross-sectional view of a heart depicting the left atrium, left ventricle, and native mitral valve of the heart. FIG. 10B also shows an embodiment of the expandable prosthetic valve device 100 implanted in the native mitral valve region of the heart.

Figure 10C:
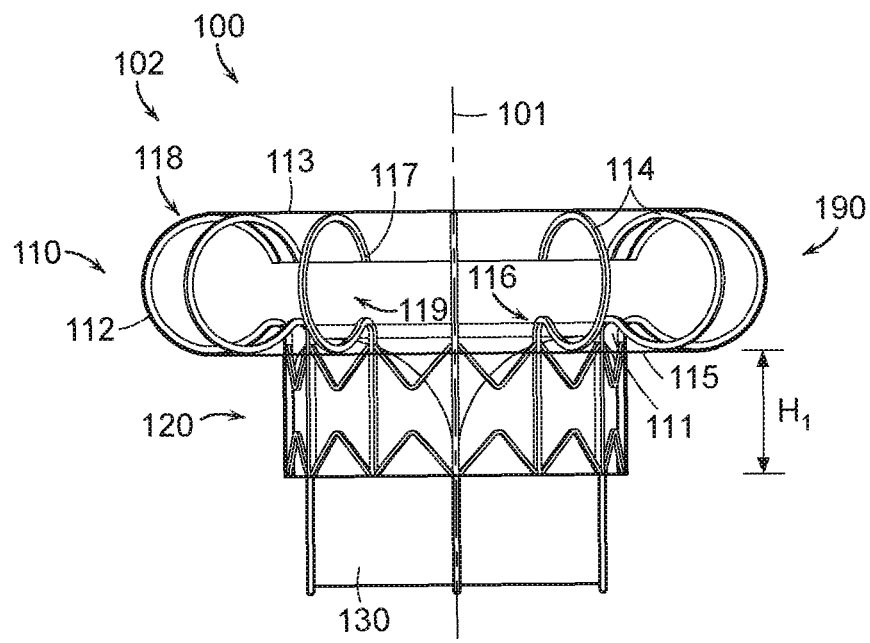
FIGS. 10C-10D are side and top views, respectively, of a prosthetic heart valve device in accordance with an embodiment of the present technology.
Figure 10D:
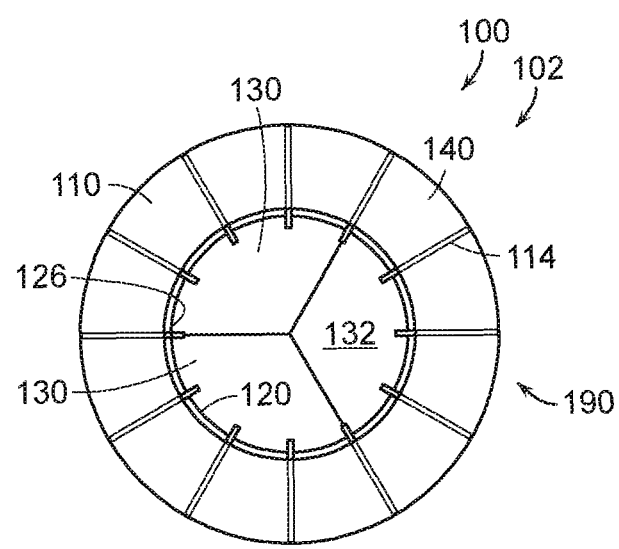

As shown in FIG. 10A, the device 100 can include an expandable retainer 110 at least partially surrounding and coupled to an inner valve support 120. The device 100 can further include a prosthetic valve 130 coupled to, mounted within, or otherwise carried by the valve support 120. FIGS. 10C-10D are side and top views, respectively, of the prosthetic heart valve device 100 in accordance with the present technology. Referring to FIG. 10A, the device 100 can also include one or more sealing members 140 that can extend around an inner surface 141 or outer surface 142 (as shown) of the retainer 110 and/or around an interior surface 126 (shown in FIG. 10D) or exterior surface 127 (shown in FIG. 10A) of the valve support 120 to prevent paravalvular (e.g., paraprosthetic) leaks between the device 100 and the native tissue and/or between the retainer 110 and the valve support 120.

The prosthetic heart valve device 100 can be movable between a delivery configuration (not shown), an expanded configuration 102 (FIG. 10A), and a deployed configuration 104 (FIG. 10B). In the delivery configuration, the prosthetic heart valve device 100 has a low profile suitable for delivery through small-diameter guide catheters positioned in the heart via the trans-septal, retrograde, or trans-apical approaches described herein. In some embodiments, the delivery configuration of the prosthetic heart valve device 100 will preferably have an outer diameter no larger than about 8-10 mm for trans-septal approaches, about 8-10 mm for retrograde approaches, or about 8-12 mm for trans-apical approaches to the mitral valve MV. As used herein, "expanded configuration" refers to the configuration of the device when allowed to freely expand to an unrestrained size without the presence of constraining or distorting forces. "Deployed configuration," as used herein, refers to the device once expanded at the native valve site and subject to the constraining and distorting forces exerted by the native anatomy.

Referring back to FIG. 3, "subannular," as used herein, refers to a portion of the mitral valve MV that lies on or downstream DN of the plane PO of the native orifice. As used herein, the plane PO of the native valve orifice is a plane generally perpendicular to the direction of blood flow through the valve and which contains either or both the major axis MVA1 or the minor axis MVA2 (FIG. 5C). Thus, a subannular surface of the mitral valve MV is a tissue surface lying on the ventricular side of the plane PO, and preferably one that faces generally downstream, toward the left ventricle LV. The subannular surface may be disposed on the annulus AN itself or the ventricular wall behind the native leaflets LF, or it may comprise a surface of the native leaflets LF, either inward-facing IF or outward-facing OF, which lies below the plane PO. The subannular surface or subannular tissue may thus comprise the annulus AN itself, the native leaflets LF, leaflet/annulus connective tissue, the ventricular wall or combinations thereof.

In operation, the prosthetic heart valve device 100 can be intravascularly delivered to a desired location in the heart, such as an intracardiac location near the mitral valve MV, while in the delivery (e.g., collapsed) configuration within a delivery catheter (not shown). Referring to FIG. 10B, the device 100 can be advanced to a position within or downstream of the native annulus AN where the device 100 can be released from the delivery catheter to enlarge toward the expanded configuration 102 (FIG. 10A). The device 100 will engage the native tissue at the desired location, which will deform or otherwise alter the shape of the device 100 into the deployed configuration 104 (FIG. 10B). Once released from the catheter, the device 100 can be positioned such that at least a portion of the expandable retainer 110 engages a subannular surface of the native valve so as to resist systolic forces and prevent upstream migration of the device 100 (FIG. 10B). In the embodiment illustrated in FIG. 10B, an upstream perimeter 113 of the retainer 110 engages the inward-facing surfaces IF (FIG. 3) of the native leaflets LF, which are pushed outwardly and folded under the native annulus AN. The leaflets LF engage a ventricular side of the annulus AN and are prevented from being pushed further in the upstream direction, thus maintaining the retainer 110 below the plane of the native valve annulus. In some embodiments, however, some portions of the retainer 110 may extend above the annulus AN, with at least some portions of the retainer 110 engaging tissue in a subannular location to prevent migration of the device 100 toward the left atrium LA. As shown in FIG. 10B, the leaflets LF can lie in apposition against the outer surface 142 of the retainer 110 forming a blood-tight seal with the sealing member 140.

In accordance with aspects of the present technology, the expandable retainer 110, while in a deployed configuration 104, conforms to the irregularly-shaped mitral annulus AN, effectively sealing the device 100 against the native annulus AN to anchor the device and to prevent paravalvular leaks.

As described further herein, the retainer 110 mechanically isolates the valve support 120 from distorting forces present in the heart such that the retainer 110 may adapt and/or conform to native forces while the valve support 120 maintains its structural integrity. Accordingly, the retainer 110 can be sufficiently flexible and resilient and/or coupled to the valve support 120 in such a manner as to mechanically isolate the valve support 120 from the forces exerted upon the retainer 110 by the native anatomy. Alternatively, or in addition to the above features, the valve support 120 may be more rigid and/or have greater radial strength than the radial strength of the retainer 110 so as to maintain its cylindrical or other desired shape and to ensure proper opening and closing of the prosthetic valve 130 housed within the valve support structure 120. In some embodiments, the valve support 120 has a radial strength of at least 100%, or in other embodiments at least 200%, and in further embodiments at least 300%, greater than a radial strength of the retainer 110. In one embodiment, the valve support 120 can have a radial strength of approximately 10 N to about 12 N. Thus, if deformed from its unbiased shape by exerting a radially compressive force against its circumference, the valve support 120 can exhibit a hoop force which is about 2 to about 20 times greater for a given degree of deformation than will be exhibited by the retainer 110.

The retainer 110 comprises a flexible, upstream portion of the device 100 and is implanted such that at least a portion of the retainer 110 engages tissue at or near the native mitral annulus. The retainer 110 can be a generally outward oriented portion of the device 100, as shown in FIG. 10C. In one embodiment, the retainer 110 forms a donut-shaped flange 190 having an arcuate outer surface 142 for engaging tissue and an inner lumen defining a passage for blood to flow through the valve support 120. In another example, the outer surface 142 can have other shapes, such as linear, triangular, an irregular shape, etc. in some embodiments, the retainer 110 can include a plurality of circumferentially positioned, resiliently deformable and flexible ribs 114 which are coupled at their downstream ends 116 to the valve support 120. Once deployed, at least a portion of the upstream region 118 of the flexible ribs 114 can expand outward from the valve support 120 to engage a surface at or near the native valve (e.g., mitral valve). As shown in FIG. 10C, the inflow end of the valve support 120 is radially inward from and longitudinally overlapping a portion of the retainer 110 when the device 100 is in the expanded configuration 102.

Additionally, FIGS. 10A-10D also illustrate that the flexible ribs 114, in one embodiment, can have a general C-shape configuration with tips 117 of the flexible ribs 114 and opening 119 of the C-shape configuration oriented toward a longitudinal axis 101 of the device 100. As shown in FIGS. 10A-10D, the each individual flexible rib 114 can be independent or otherwise unconnected to any other (e.g., adjacent) flexible rib 114 of the retainer 110. However, in some embodiments, not shown, the retainer 110 can have circumferential connectors connecting one or more flexible ribs 114 of the retainer 110. In some embodiments, the flexible ribs 114 may be divided along their length into multiple, separated segments (shown below with respect to FIGS. 13A-13G). The plurality of flexible ribs 114 can be formed from a deformable material or from a resilient or shape memory material (e.g., nitinol). In other embodiments, the retainer 110 can comprise a mesh or woven construction in addition to or in place of the flexible ribs 114. For example, the retainer 110 could include a plurality of flexible wires or filaments arranged in a diamond pattern or other configuration. In a particular example, the retainer 110 can be formed of a pre-shaped nitinol tube having, for example, a wall thickness of approximately 0.010 inches to about 0.130 inches.

Figure 11:
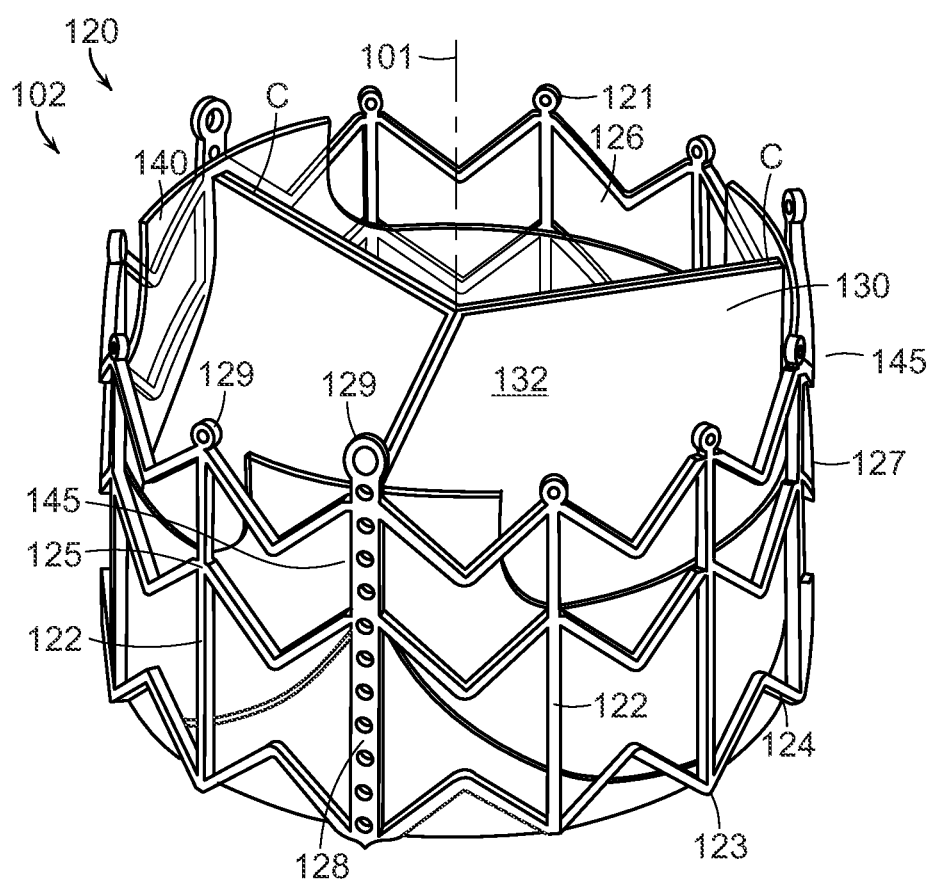
FIG. 11 is an isometric view of a valve support with a prosthetic valve mounted therein in accordance with an embodiment of the present technology.

FIG. 11 shows an embodiment of the valve support 120 that can be used in the various embodiments of the prosthetic heart valve device 100 shown in FIGS. 10A-10D. FIG. 11 is an isometric view of the valve support 120 shown in an expanded configuration 102 in accordance with the present technology. Referring to FIGS. 10A-10D and 11 together, several embodiments of the valve support 120 can be generally cylindrical having an upstream end 121 and a downstream end 123 formed around the longitudinal axis 101 with a circular, oval, elliptical, kidney-shaped, D-shaped, or other suitable cross-sectional shape configured to support a tricuspid or other prosthetic valve 130. In some embodiments, the valve support 120 includes a plurality of posts 122 connected circumferentially by a plurality of struts 124. The posts 122 and struts 124 can be arranged in a variety of geometrical patterns that can expand and provide sufficient resilience and column strength for maintaining the integrity of the prosthetic valve 130. For example, the plurality of posts 122 can extend longitudinally across multiple rows of struts 124 to provide column strength to the valve support 120. However, in other embodiments, the valve support 120 can include a metallic, polymeric, or fabric mesh or woven construction.

Generally, the plurality of posts 122 can extend along an axial direction generally parallel to the longitudinal axis 101 and the struts 124 can extend circumferentially around and transverse to the longitudinal axis 101. The posts 122 can extend an entire longitudinal height $H_1$ (shown in FIG. 10C) of the valve support 120 and in one embodiment the height $H_1$ can be approximately 14 mm to about 17 mm. Referring to FIG. 11, the struts 124 can form a series of rings around the longitudinal axis 101, wherein each ring has a circumferentially expandable geometry. In the example shown in FIG. 11, the struts 124 are formed in a series of zig-zags to form a chevron configuration. Alternative expandable geometries can include sinusoidal patterns, diamond configurations, closed cells, open cells, or other expandable configurations. The plurality of struts 124 can attach to the plurality of posts 122 so as to define a plurality of nodes 125 where the struts and posts intersect. The plurality of struts 124 and the plurality of posts 122 can be formed from a deformable material or from a resilient or shape memory material (e.g., nitinol).

As shown in FIG. 11, the valve support 120 has the interior surface 126 and the exterior surface 127, and the valve support 120 is configured to receive the prosthetic valve 130 within an interior lumen of the valve support 120 to inhibit retrograde blood flow (e.g., blood flow from the left ventricle into the left atrium). Accordingly, the valve support 120 can provide a scaffold to which prosthetic valve tissue can be secured and provide a scaffold that has sufficient axial rigidity to maintain a longitudinal position of the prosthetic valve 130 relative to the retainer 110. The valve support 120 can further provide such a scaffold having radial rigidity to maintain circularity (or other desired cross-sectional shape) to ensure that leaflets 132 of the prosthetic valve 130 coapt or otherwise seal when the device 100 is subject to external radial pressure. In one embodiment, the valve support 120 can have a support region 145 along the longitudinal axis 101 that is configured to attach to the prosthetic valve, or in other embodiments, be aligned with the coaptation portion of the leaflets 132 (shown in FIG. 11).

The valve 130 may comprise a temporary or permanent valve adapted to block blood flow in the upstream direction and allow blood flow in the downstream direction through the valve support 120. The valve 130 may also be a replacement valve configured to be disposed in the valve support 120 after the device 100 is implanted at the native mitral valve. The leaflets 132 may be formed of various flexible and impermeable materials including PTFE, Dacron®, pyrolytic carbon, or other biocompatible materials or biologic tissue such as pericardial tissue or xenograft valve tissue such as porcine heart tissue or bovine pericardium. Other aspects of valve 130 are described further below.

The interior surface 126 within the lumen of the valve support 120 can be covered at least partially by an impermeable sealing member 140 to prevent blood flow from inside the valve support 120 to the outside of the valve support 120, where it could leak around the exterior of the valve support 120. In another embodiment, the sealing member 140 may be affixed to the exterior surface 127 of the valve support 120 and, in either embodiment, may be integrally formed with or attached directly to valve 130. In an additional embodiment, the sealing member 140 can be applied on at least portions of both the interior surface 126 and the exterior surface 127 of the valve support 120.

In accordance with aspects of the present technology and as shown in FIG. 11, the prosthetic valve 130 can be sutured, riveted, glued, bonded, or otherwise fastened to posts 122 or commissural attachment structures 128, which are configured to align with valve commissures C. The posts 122 or commissural attachment structures 128 can include eyelets 129, loops, or other features formed thereon to facilitate attachment of sutures or other fastening means to facilitate attachment of the prosthetic valve 130. In one embodiment, as shown in FIG. 11, the attachment structures 128 can be integrated into the structural frame of the valve support 120 such that the attachment structures 128 are distributed around the circumference of the valve support 120 and function as posts 122. In other embodiments, not shown, the attachment structures 128 can be attachment pads formed on parts of the posts 122 (e.g., along an upper end of the posts 122) or can be separate structures that can be coupled to posts 122, struts 124 or other components along the interior surface 126 of the valve support 120. The prosthetic valve 130 may also be attached to the sealing member 140, which can be a sleeve attached to the interior surface 126 of the valve support 120.

Once attached, the prosthetic valve 130 can be suitable to collapse or compress with the device 100 for loading into a delivery catheter (not shown). In one embodiment, the prosthetic valve 130 has a tri-leaflet configuration, although various alternative valve configurations may be used, such as a bi-leaflet configuration. The design of the prosthetic valve 130, such as the selection of tri-leaflet vs. bi-leaflet configurations, can be used to determine the suitable shape of the valve support 120. For example, for a tri-leaflet valve, the valve support 120 can have a circular cross-section, while for a bi-leaflet valve, alternative cross-sectional shapes are possible such as oval or D-shaped cross-sections. In particular examples, the valve support can have a circular cross-sectional diameter of approximately 25 mm to about 30 mm, such as 27 mm.

In some arrangements, the valve support 120 can have a permanent prosthetic valve pre-mounted therein, or the valve support 120 may be configured to receive a separate catheter-delivered valve following implantation of the device 100 at the native mitral valve. In arrangements where a permanent or replacement valve is desirable, the valve support 120 can further include a temporary valve pre-mounted within the interior lumen. If a period of time between placement of the device 100 and further implantation of the permanent prosthetic valve is desirable, a temporary valve sewn into or otherwise secured within the valve support 120 can assure regulation of blood flow in the interim. For example, temporary valves may be used for a period of about 15 minutes to several hours or up to a several days. Permanent or replacement prosthetic valves may be implanted within a temporary valve or may be implanted after the temporary valve has been removed. Examples of pre-assembled, percutaneous prosthetic valves include, e.g., the CoreValve ReValving® System from Medtronic/Corevalve Inc. (Irvine, Calif., USA), or the Edwards-Sapien® valve from Edwards Lifesciences (Irvine, Calif., USA). If adapted to receive a separate catheter-delivered valve, the valve support 120 may have features within its interior lumen or on its upper or lower ends to engage and retain the catheter-delivered valve therein, such as inwardly extending ridges, bumps, prongs, or flaps. Additional details and embodiments regarding the structure, delivery and attachment of prosthetic valves, temporary valves and replacement valves suitable for use with the prosthetic heart valve devices disclosed herein can be found in International PCT Patent Application No. PCT/US2012/043636, entitled "PROSTHETIC HEART VALVE DEVICES AND ASSOCIATED SYSTEMS AND METHODS," filed Jun. 21, 2012, the entire contents of which are incorporated herein by reference.

In some embodiments, a downstream portion 111 of the retainer 110 can be coupled to or near the upstream end 121 of the valve support 120 and extend outward and in an upstream direction from the valve support 120 in a manner that does not unduly influence the shape of the valve support 120. Accordingly, in some embodiments, the retainer 110 can be configured to engage and deform to the shape of the native tissue on or under the annulus while a cross-sectional shape of the valve support 120 remains sufficiently stable or substantially undeformed. For example, the valve support 120 (e.g., at least at the upstream end 121) can be spaced longitudinally downstream from at least a tissue engaging portion 112 of the retainer 110 such that if the retainer 110 is deformed inwardly, the cross-sectional shape of the valve support 120, which remains positioned downstream of the tissue engaging portion 112 of the retainer 110, remains substantially undeformed. As used herein, "substantially undeformed" can refer to situations in which the valve support 120 is not engaged or deformed, or can refer to scenarios in which the valve support 120 can deform slightly but the prosthetic valve 130 remains intact and competent (e.g., the leaflets 132 coapt sufficiently to prevent retrograde blood flow). In such arrangements, leaflets 132 of the prosthetic valve 130 can close sufficiently even when the device 100 is under systolic pressures or forces from the pumping action of the heart.

As illustrated in FIGS. 10A-10D, the retainer 110 can be coupled to or near the upstream end 121 of the valve support 110 the valve support 120 in such that the valve support 120 and valve 130 reside within the left ventricle. Alternatively, the retainer 110 can be coupled to the valve support 120 anywhere along a length of the valve support 120 such that the valve support 120 and valve 130 can reside within the annulus or above the annulus of the native heart valve. The valve support 120 and retainer 110 may be coupled by a variety of methods known in the art, e.g., suturing, soldering, welding, bonding, staples, rivets or other fasteners, mechanical interlocking, friction, interference fit, or any combination thereof.

Figure 12A:
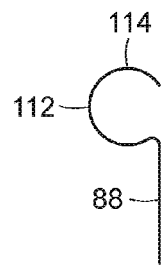
FIGS. 12A-12H are side views of various mechanisms of coupling a valve support to a retainer in accordance with additional embodiments of the present technology.
Figure 12B:
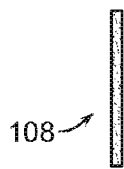
Figure 12C:
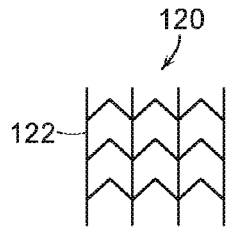
Figure 12D:
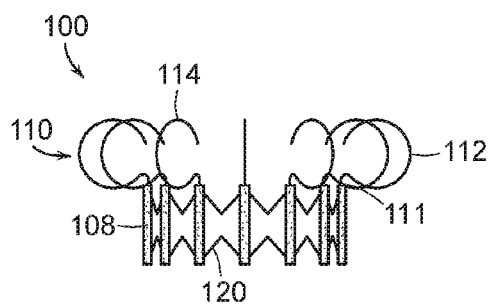

FIGS. 12A-12H are side views of additional mechanisms of coupling the valve support 120 to the retainer 110 that can allow mechanical isolation of the valve support 120 from the retainer 110 in accordance with additional embodiments of the present technology. Referring to FIGS. 12A-12D, the flexible ribs 114 can include rib posts 88 (FIG. 12A) that can be coupled to valve support posts 122 (FIG. 12C) using individual hypotubes 108 (shown in FIG. 12B). For example, as shown in FIG. 12D, the rib post 88 may be aligned with the individual valve support posts 122 and the hypotube 112 may be slipped over both the valve support posts 122 and the rib posts 88. The hypotubes 108 can be crimped or otherwise adhered to valve support posts 122 and the rib posts 88 such that the flexible ribs 114 are connected to and aligned with valve support posts 122 in a manner that allows the tissue engaging portions 112 to extend outward and in an upstream direction from the valve support 120.

Figure 12E:
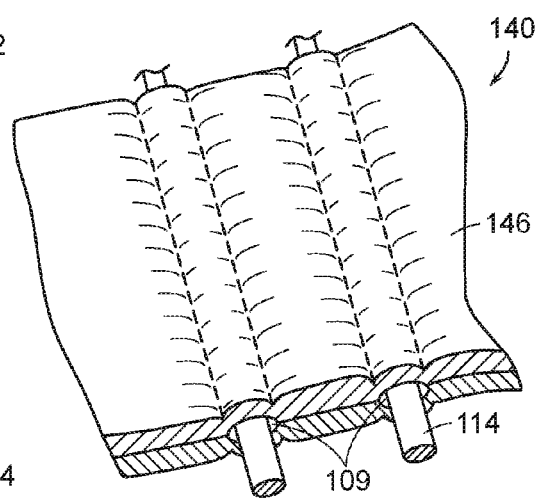
Figure 12F:
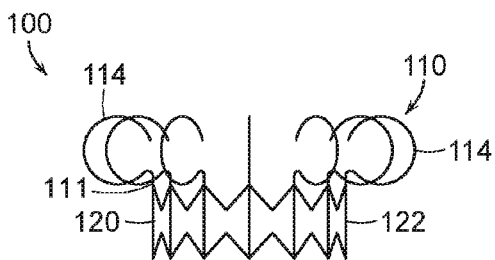

If the retainer 110 and the valve support are separate structures, a sealing member 140 or other overlaying structure may be attached to both the retainer 110 and the valve support 120 to interconnect the two structures. For example, the valve support 120 can be covered by a sealing member 140, such as a sleeve 146 that includes a plurality of longitudinal pockets 109 formed (e.g., by suturing or bonding two layers of sleeve fabric together) or otherwise incorporated circumferentially around the sleeve 146. As shown in FIG. 12E, each individual rib 114 can be constrained within the pockets 109 formed in the sleeve 146, and the sleeve can be coupled to an interior or exterior surface 126, 127 of the valve support (FIG. 11). In other embodiments, the valve support 120 and the retainer 110 can be integrally formed with one another. For example, the flexible ribs 114 can be formed integrally with the posts 122 of the valve support 120 (shown in FIGS. 10C and 12F.

Figure 12G:
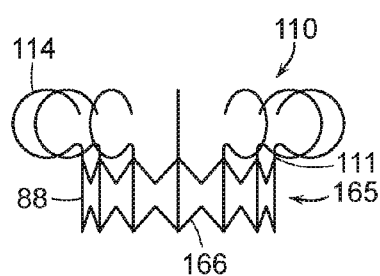
Figure 12H:
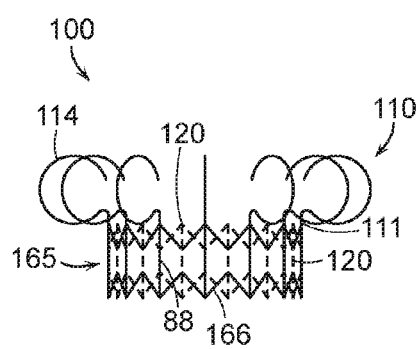

In a further embodiment shown in FIGS. 12G-12H, the retainer 110 may include a retainer frame 165, separate from the frame of the valve support 120 (FIG. 12G). The retainer frame 165, in one embodiment, may include rib posts 88 connected circumferentially by deformable and/or flexible connectors 166, and can be configured to receive or partially surround the valve support 120 (FIG. 12H). In one arrangement, the retainer frame 165 can be delivered by catheter and deployed at a target site in the native heart valve and the valve support 120 can be delivered separately following deployment and implantation of the retainer frame 165. In another arrangement, the retainer frame 165 can be configured to receive or be coupled to the support frame 120 prior to delivery of the device 100 to the target site.

Referring back to FIGS. 10A-10D, the flexible ribs 114 can be less rigid than the posts 122 and/or struts 124 of the valve support 120, allowing greater flexibility in the retainer 110 and/or more stability to the shape and position of the valve support 120. In some embodiments, the flexibility of the retainer 110 can allow the retainer 110 to absorb distorting forces as well as allow the device 100 to conform to the irregular, non-circular shape of the native annulus (while leaving the valve support 120 substantially unaffected), encouraging tissue ingrowth and creating a seal to prevent leaks between the device 100 and the native tissue. In addition, the flexible ribs 114 can be configured to press radially outward against the native valve, ventricular and/or aortic structures so as to anchor the device 100 in a desired position, as well as maintain an upstream deployed circumference 150' larger than that of the native annulus such that subannular positioning effectively prevents upstream migration of the device 100 (described further below in FIG. 18C). Furthermore, the flexible ribs 114 can have sufficient resilience and column strength (e.g., axial stiffness) to prevent longitudinal collapse of the retainer 110 and/or the device 100 and to resist movement of the device 100 in an upstream direction.

In accordance with embodiments of the present technology, the valve 130 and valve support 120 are effectively mechanically isolated from the distorting forces exerted on the retainer 110 by the native tissue, e.g., radially compressive forces exerted by the native annulus and/or leaflets, longitudinal diastolic and systolic forces, hoop stress, etc. For example, deformation of the retainer 110 by the native tissue can change a cross-section of the retainer 110 (e.g., to a non-circular or non-symmetrical cross-section), while the valve support 120 may be substantially undeformed. In one embodiment, at least a portion of the valve support 120 can be deformed by the radially compressive forces, for example, where the retainer 110 is coupled to the valve support 120 (e.g., the downstream end 123). However, the upstream end 121 of the valve support 120 and/or the valve support region 145 (FIG. 11) is mechanically isolated from the retainer 110 and the compressive forces such that at least the valve support region 145 can be substantially undeformed. Thus the valve support 120, and at least the valve support region 145, can maintain a circular or other desirable cross-section so that the valve remains stable and/or competent. The flexibility of the ribs 114 can contribute to the absorption of the distorting forces, and also aid in mechanically isolating the valve support 120 and valve 130 from the retainer 110 and from the native anatomy.

As shown in FIG. 10C, the retainer 110 is comprised of a series of circumferentially positioned flexible ribs 114 which are coupled or otherwise integrated at their downstream ends 116 to the valve support 120. Unlike valve support posts 122, the flexible ribs 114 may not be circumferentially connected by struts which can allow for greater movement, flexing, bending, rotating and/or deformation of the individual ribs 114 and the retainer 110 as a whole. In certain embodiments in which the retainer 110 did include circumferential struts or supports (not shown) for retaining or connecting the ribs 114, the struts may be more flexible than the struts 124 utilized in the valve support 120.

Figure 13A:
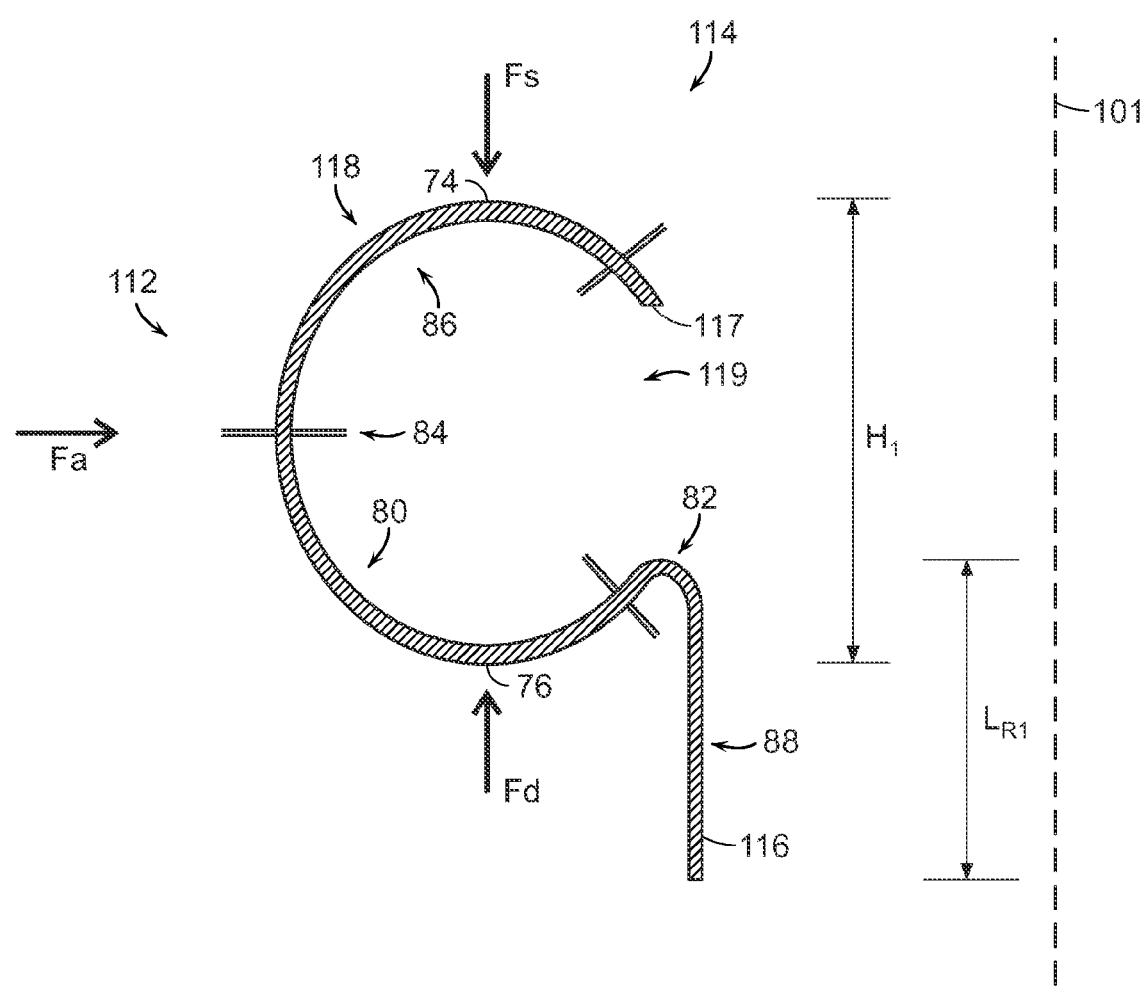
FIGS. 13A-13G are partial side views of a variety of flexible rib configurations in accordance with additional embodiments of the present technology.
Figure 13B:
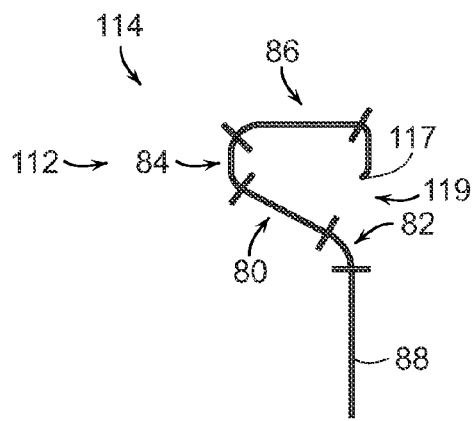
Figure 13C:
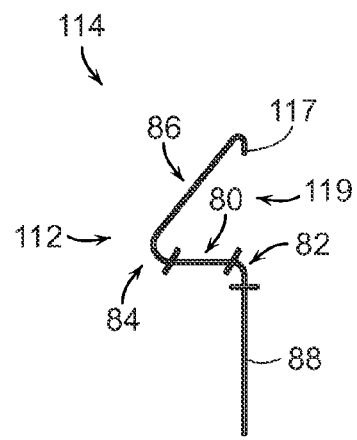
Figure 13D:
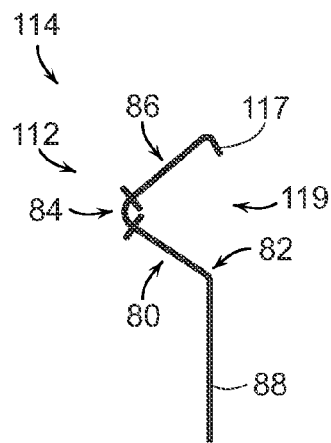
Figure 13E:
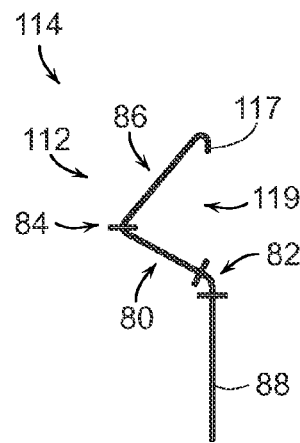

FIGS. 13A-13G are partial side views of a variety of flexible rib configurations in accordance with additional embodiments of the present technology. Referring to FIG. 13A, the ribs 114, in one embodiment, can generally have an arcuate or C-shaped tissue engaging portion 112 and include the rib post 88 at the downstream end 116 of the rib 114. In some embodiments, the rib post 88 can be generally linear and have a suitable length $L_{R1}$ for extending the retainer 110 a desirable distance upstream from a connection (not shown) to the valve support 120. In some embodiments, the rib post 88 can be generally parallel to the longitudinal axis 101 of the device 100 and/or valve support 120 (shown in FIG. 10C). Following the general curvature of the C-shaped tissue engaging portion 112 shown in FIG. 13A, a first segment 80 of the tissue engaging portion 112 can extend radially outward from the rib post 88 beginning at a first transition 82. The first transition 82 can be a curved or U-shaped section as shown to orient the first segment 82 outward from the rib post 88. The first segment 80 can be arcuate or generally curved in an outward and upstream direction to reach a second transition 84. A second segment 86 of the tissue engaging portion 112 can be arcuate or generally curved and extend (e.g., relative to the rib post 88) from the second transition 84 in an upstream and inward direction. The second segment 86 can also curve slightly downstream at the rib tip 117. The opening 119 of the C-shaped tissue engaging portion 112 of the rib 114 is created in the space between the first transition 82 and the rib tip 117.

Additional embodiments of rib shapes are shown in FIGS. 13B-13G. For example, rib segments, such as the first and second segments 80, 86, can be generally linear (FIGS. 13B-13E). Other embodiments of tissue engaging portion 112 can have transitions 82 and 84 with less curvature or greater curvature. For example, the first transition segment 82 may comprise a curved section with a distinct inflection point (shown in FIGS. 13A and 13C-13E) or a short continuous segment with a constant radial curve (FIG. 12B). The tissue engaging portion 112 can also include additional transitions and/or segments to form desirable rib shapes, such as generally square-shaped (FIG. 13B), or generally triangular-shaped (FIGS. 13C-13E) tissue engaging portions 112. Similar to the embodiment of the tissue engaging portion 112 shown in FIG. 13A, the tissue engaging portion 112 shown in FIGS. 13B-13E have the openings 119 which can face inward toward a retainer interior (shown in FIGS. 10A-10D); however, one of ordinary skill in the art will recognize that the ribs 114 can be oriented in a different direction, such as having the opening 119 facing outward with respect the longitudinal axis 101 of the device 100 (not shown). Additional embodiments of the tissue engaging portion 112 can be formed without openings 119.

Figure 13F:
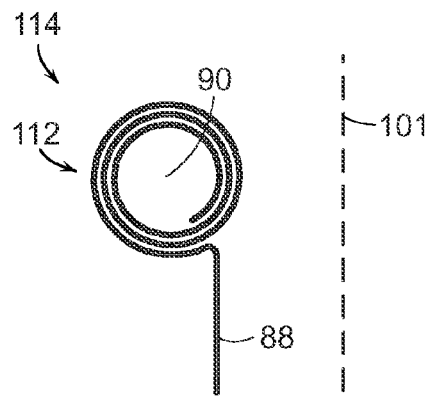
Figure 13G:
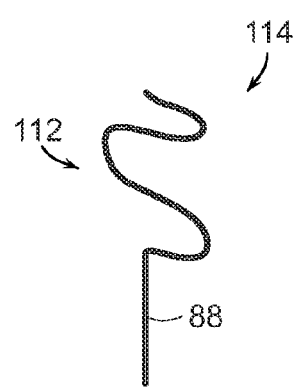

In other embodiments, the tissue engaging portion 112 may take on other unique geometries. As shown in FIG. 13F, the tissue engaging portion 112 may coil or extend around an axis 90 transverse to the longitudinal axis 101. Or, as shown in FIG. 13G, the tissue engaging portion 112 may have multiple segments extending radially outward and/or multiple segments extending radially inward with respect to the rib post 88 in an irregular or in a patterned configuration.

Referring back to FIG. 13A, the tissue engaging portion 112 can have a height $H_1$ between an upper surface 74 and a lower surface 76. Accordingly, in addition to the shape of the tissue engaging portion 112, the overall height $H_1$ of the tissue engaging portion 112 can be selected to accommodate the anatomy at the desired target location of the heart valve.

Referring again to FIG. 13A, the tissue engaging portion 112 of the rib 114 can be configured to absorb, translate and/or mitigate distorting forces present with the heart during, for example, systole and diastole. The shape of the tissue engaging portion 112 can be selected to accommodate forces, such as radially compressive forces, e.g., exerted by the native annulus and/or leaflets Fa, longitudinal diastolic Fd and systolic Fs forces, hoop stress, etc. Absorption of the distorting forces can serve to mechanically isolate the retainer 110 from the valve support 120. In accordance with the present technology, the ribs 114 may flex, bend, rotate or twist under the distorting forces while the valve support 120 substantially maintains its rigidity and/or original shape (e.g., a generally circular shape). In a particular example, the device 100 can include a tricuspid valve 130 retained within a generally circular valve support 120 (FIGS. 10A-11). When deployed and operational, the cross-sectional shape of the valve support 120 can remain sufficiently stable when the retainer 110 is deformed in a non-circular shape by engagement with the tissue such that the valve 130 remains competent.

FIGS. 14A-14J are side views of various flexible ribs 114 flexing in response to a distorting force F in accordance with further embodiments of the present technology. The degree of flexibility of individual ribs 114 (and thus the retainer 110) may be consistent among all ribs 114 of a retainer 110, or, alternatively, some ribs 114 may be more flexible than other ribs 114 within the same retainer 110. Likewise, a degree of flexibility of individual ribs 114 may be consistent throughout an entire length of the rib 114 or curvature of the tissue engaging portion 112, or the degree of flexibility can vary along the length and/or curvature of each rib 114.

As shown FIGS. 14A-14J, the tissue engaging portions 112 of the ribs 114 may flex relative to the rib post 88 in response to varying distorting forces F that can be applied by the surrounding tissue during or after implantation of the device 100. From a static position (FIG. 14A), the tissue engaging portion 112a may flex downward to a position 112b (FIG. 14B) or upward to a position 112c (FIG. 14C) in response to a downward force $F_1$ or an upward force $F_2$, respectively. Similarly, the tissue engaging portion 112a may flex inward to a position 112d (FIG. 14D) or outward to a position 112e (FIG. 14E) in response to a laterally directed inward force $F_3$ or a laterally directed outward force $F_4$, respectively. As shown in FIGS. 14A-14E, the tissue engaging portion 112a may flex and/or rotate inwardly/outwardly in response to the laterally directed forces $F_3$, $F_4$, or upward/downward in response to the generally vertically directed forces $F_1$, $F_2$ without altering the general shape of the tissue engaging portion 112. In one embodiment, the position of the tissue engaging portion 112 can occur by flex or rotation around the first transition 82 (FIGS. 14A-14E).

Figures 14A, 14B, 14C, 14D, 14E:
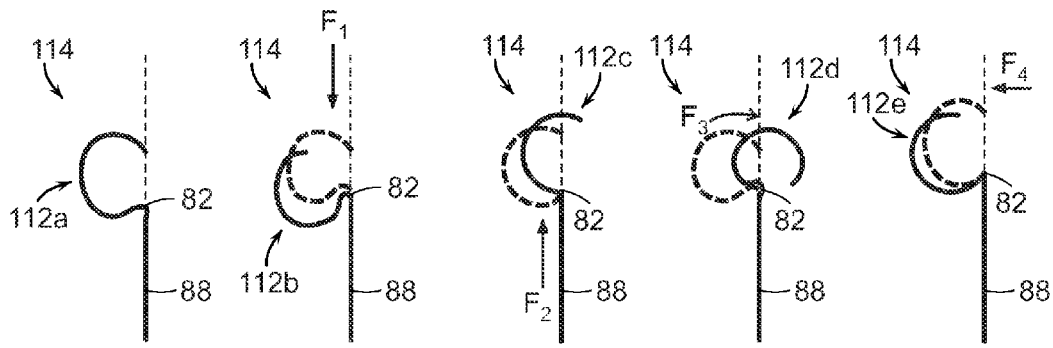
FIGS. 14A-14J are side views of various flexible ribs flexing in response to a distorting force in accordance with further embodiments of the present technology.
Figures 14F, 14G:
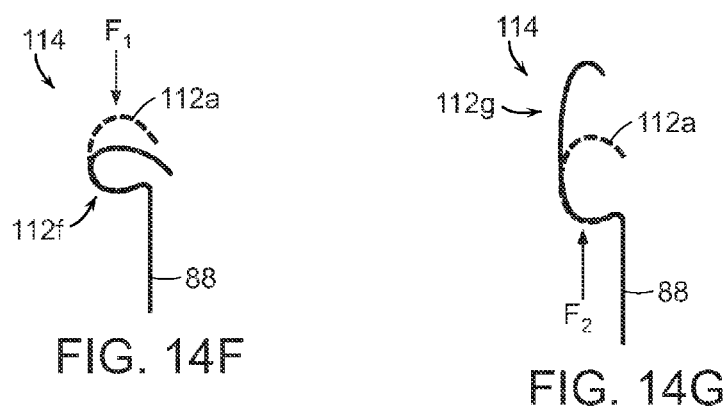
Figures 14H, 14I, 14J:
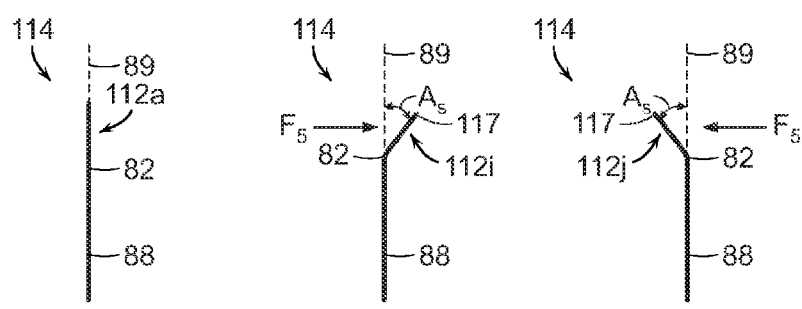

In other arrangements, the rib 114 can be configured to alter the shape of the tissue engaging portion 112a in response to forces, such as to the shape/position 112f in response to the downward force $F_1$ (FIG. 14F) and to the shape/position 112g in response to the upward force $F_2$ (FIG. 14G). Alteration of the shape and/or position of the tissue engaging portion 112, as shown in FIGS. 14F-14G, may occur by flexing, rotating and/or deformation around segments 80, 86 and/or transitions 82, 84, for example. As shown in FIGS. 14H-14J, the tissue engaging portion 112a (FIG. 14H) may also flex and/or rotate laterally (e.g., to positions 112i or 112j) in response to a laterally-directed force $F_5$, by bending at transition 82, for example, at unique and variable splay angles $A_S$ off a midline 89 such that the rib tips 117 may be splayed away from each other.

Figure 15A:
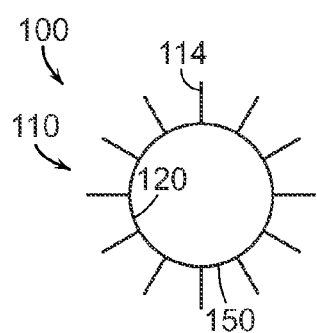
FIGS. 15A-15E are schematic top views of the prosthetic heart valve device showing a variety of rib configurations in accordance with further embodiments of the present technology.
Figure 15B:
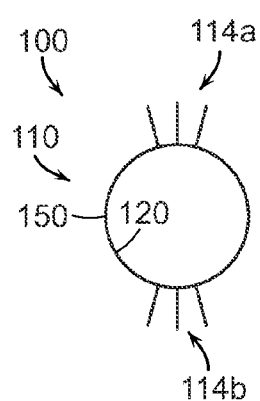
Figure 15C:
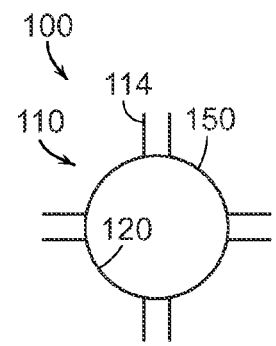
Figure 15D:
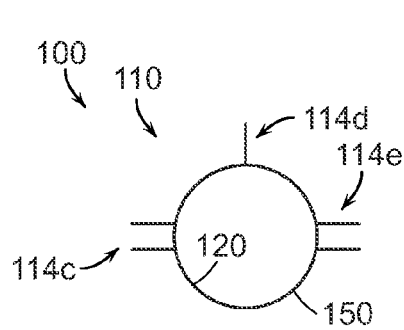
Figure 15E:
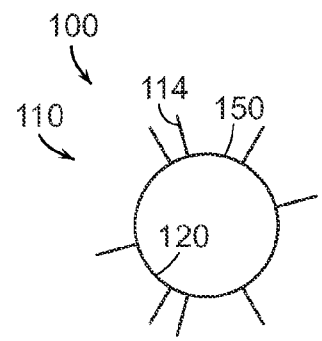

In addition to having a variety of shapes and variations in flexibility, individual ribs 114 can also be placed in a variety of positions around a circumference 150 of the retainer 110. FIGS. 15A-15E are schematic top views of the prosthetic heart valve device 100 showing a variety of rib configurations in accordance with further embodiments of the present technology. FIG. 15A shows and embodiment of the device 100 having a plurality of ribs 114 symmetrically and evenly spaced around the circumference 150 of the retainer 110. In some embodiments, the device 100 can include a first plurality of ribs 114a and second plurality of ribs 114b (FIG. 15B). In some embodiments, the first plurality of ribs 114a can have a characteristic different than the second plurality of ribs 114b. Various characteristics could include size of the rib, rib shape, rib stiffness and the number of ribs 114 within a given area of the retainer 110. As shown in FIGS. 15C and 15D, the retainer 110 can include multiple groups of ribs 114 spaced symmetrically (FIG. 15C) or asymmetrically (FIG. 15D) around the circumference 150 of the retainer 110. Referring to FIG. 15C, the groups of ribs 114c and 114e may include different numbers of ribs 114 than in other groups (e.g., 114d). In other embodiments, the ribs 114 can be unevenly spaced around the circumference 150 of the retainer 110 (FIG. 15E). The retainer 110 can include, in one embodiment, between approximately 2 ribs to about 30 ribs, and in another embodiment, between approximately 6 ribs to about 20 ribs.

Figure 16A:
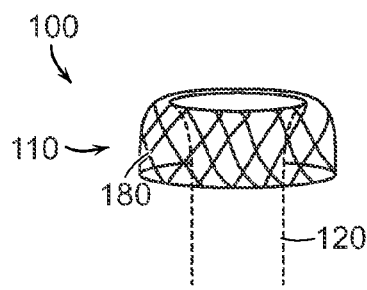
FIGS. 16A-16B are schematic side and cross-sectional views of the prosthetic heart valve device showing additional embodiments of the retainer in accordance with the present technology.
Figure 16B:
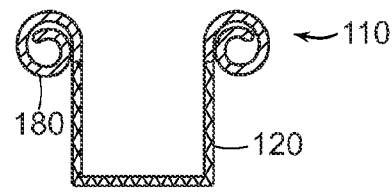

FIGS. 16A-16B are schematic side and cross-sectional views of the prosthetic heart valve device 100 showing additional embodiments of the retainer 110 in accordance with the present technology. In some embodiments, the retainer 110 can be formed from a self-expanding mesh 180 or weave of material formed from a deformable material or a resilient or shape memory material (e.g., nitinol) that can evert (FIG. 16A) or that can roll (FIG. 16B) to form the retainer 110. In other embodiments, the retainer 110 can comprise the self-expanding mesh or woven construction in addition to the flexible ribs 114. In one embodiment, the self-expanding mesh 180 could include a plurality of flexible wires or filaments arranged in a diamond pattern (FIG. 16A) or other configuration. In a particular example, the retainer 110 can be formed of a pre-shaped nitinol tube having, for example, a wall thickness of approximately 0.010 inches to about 0.130 inches.

Figure 17A:
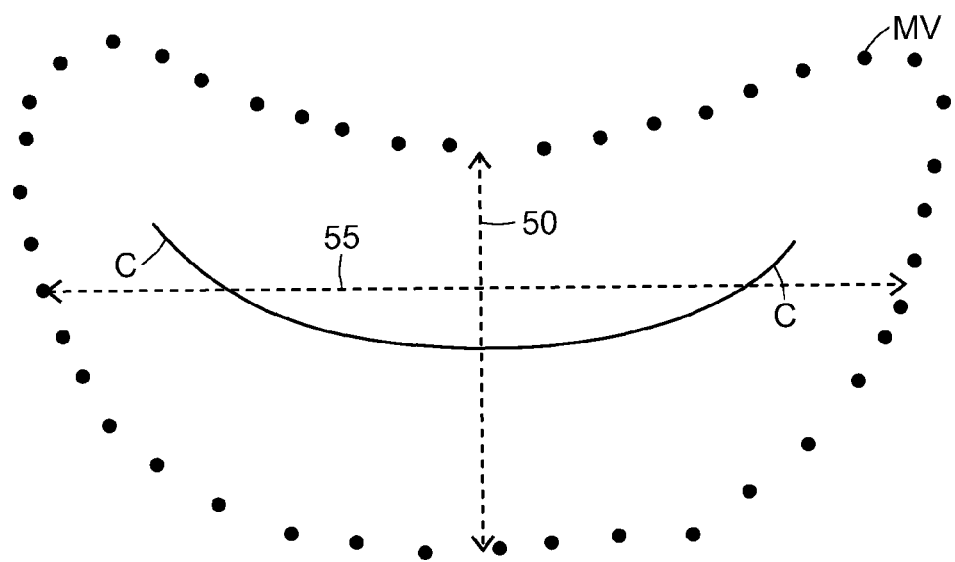
FIG. 17A is a schematic top view of a native mitral valve illustrating the major and minor axes.

The flexible characteristics of the individual ribs 114 can allow for the flexibility and conformability of the retainer 110 to engage and seal the device 100 against uneven and uniquely-shaped native tissue. Additionally, the flexibility can assist in creating a seal between the device 100 and the surrounding anatomy. FIG. 17A is a schematic top view of a native mitral valve MV illustrating the minor axis 50 and major axis 55, and FIGS. 17B-17C are schematic top views of an retainer 110 in an expanded configuration 102 and in a deployed configuration 104, respectively, overlaying the schematic of the native mitral valve MV in accordance with an embodiment of the present technology.

Figure 17B:
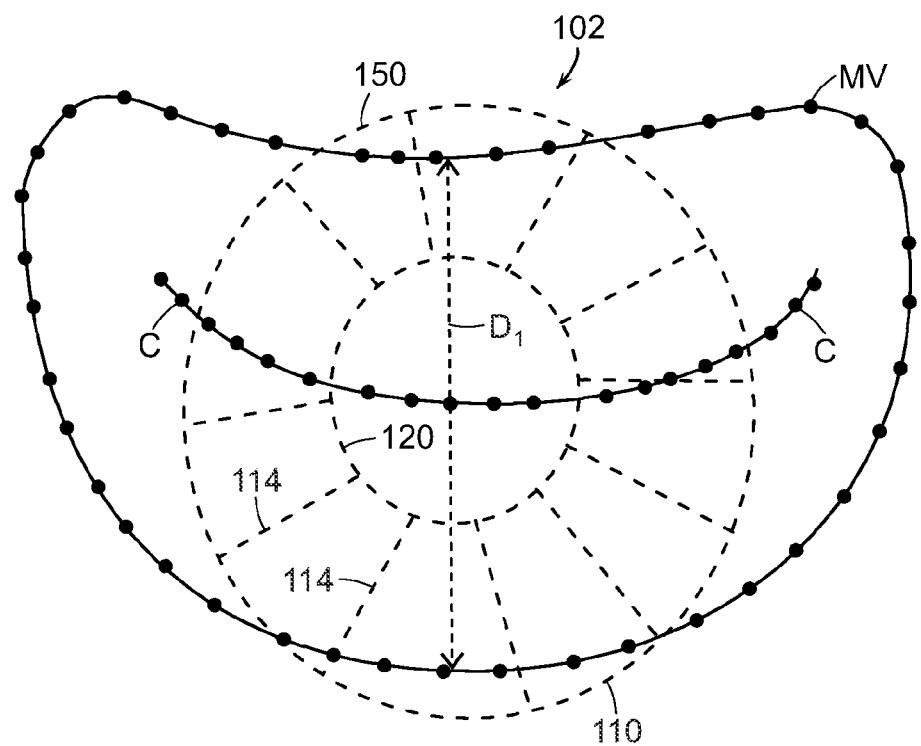
FIGS. 17B-17C are schematic top views of a retainer in an expanded configuration and in a deployed configuration, respectively, in accordance with an embodiment of the present technology.

Referring to FIG. 17B, the retainer 110 can have an outer circumference 150 with a diameter $D_1$ that is greater than the minor axis 50 (FIG. 17A) of the native annulus, and usually less than the major axis 55 of the annulus, when the retainer 110 is in an expanded configuration 102 (shown as dashed lines). In other embodiments, the retainer 110 may have a diameter $D_1$ at least as large as the distance between the native commissures C, and may be as large as or even larger than the major axis 55 of the native annulus. In some embodiments, the outer circumference 150 of the retainer 110 has the diameter $D_1$ which is approximately 1.2 to 1.5 times the diameter (not shown) of the valve support 120 (or the prosthetic valve 130), and can be as large as 2.5 times the diameter of the valve support 120 (or the prosthetic valve 130). While conventional valves must be manufactured in multiple sizes to treat diseased valves of various sizes, the valve support 120 and the prosthetic valve 130, in accordance with aspects of the present technology, may be manufactured in just a single diameter to fit a multitude of native valve sizes. For example, the valve support 120 and the prosthetic valve 130 do not need to engage and fit the native anatomy precisely. In a specific example, the valve support 120 may have a diameter (not shown) in the range of about 25 mm to about 32 mm for adult human patients. Also in accordance with aspects of the present technology, the retainer 110 may be provided in multiple diameters or having a variable size circumference 150 to fit various native valve sizes, and may range in diameter from about 28 mm to about 80 mm, or in other embodiments, greater than 80 mm.

Figure 17C:
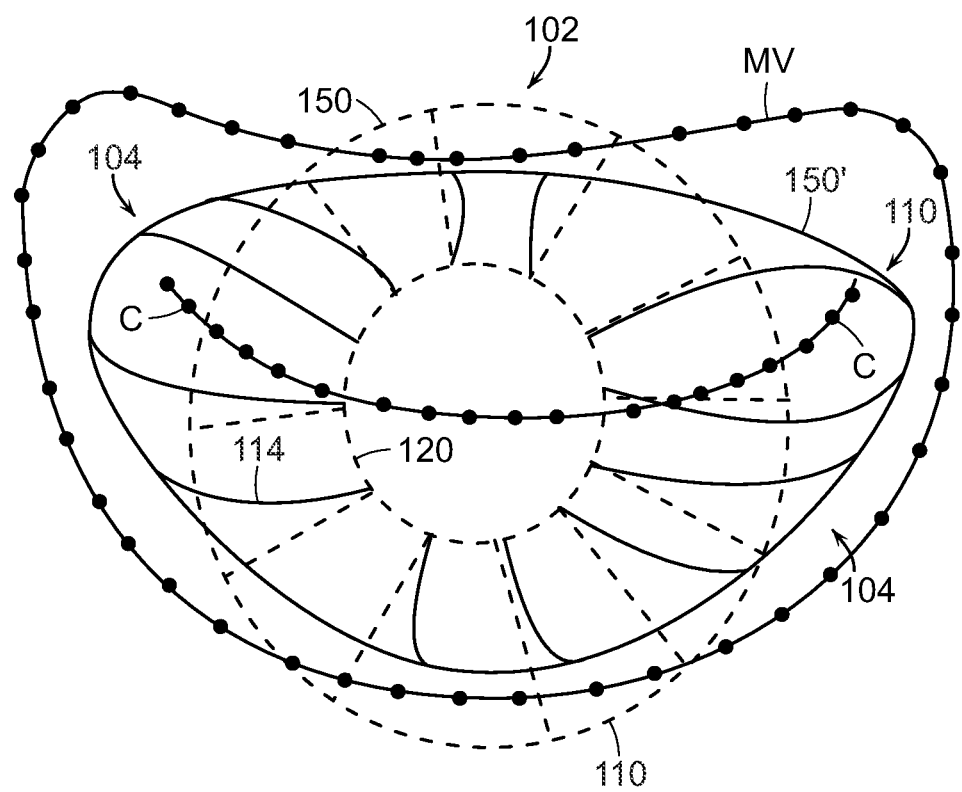

The top view of the retainer 110 shown in FIG. 17C illustrates how flexibility and/or deformation of one or more flexible ribs 114 and/or rib segments allows the retainer 110 to distort relative to the expanded configuration 102, as shown by the dashed lines, into a deployed configuration 104, as shown by the bolded lines. As shown in FIG. 17C, the retainer 110, when deployed or implanted at or under the mitral valve annulus, can conform to the highly variable native mitral valve tissue shape MV, as shown in the dotted lines. The ribs 114 can bend, twist, and stretch such that the overall shape of the retainer 110 has a deployed (e.g., a generally more oval or D-shaped, or other irregular shape) configuration 104 instead of a fully expanded configuration 102. Referring to FIGS. 17B-17C together, the retainer 110 covers the mitral valve commissures C in the deployed configuration 104, whereas the commissures C would be left unsealed or exposed in the more circular expanded configuration 102, potentially allowing paravalvular leaks. The retainer 110 could also be pre-shaped to be in a generally oval or D-shape, or other shape, when in an unbiased condition.

In many embodiments, the retainer 110 can have sufficient flexibility such that the retainer 110 conforms to the native mitral annulus when in the deployed configuration 104 (FIG. 17C), however, the retainer 110 can be configured to remain biased towards its expanded configuration 102 (e.g., FIGS. 10A and 17B) such that, when in the deployed configuration 104, the retainer 110 pushes radially outwards against the native annulus, leaflets, and/or ventricular walls just below the annulus. In some arrangements, the radial force generated by the biased retainer shape may be sufficient to deform the native anatomy such that the minor axis 50 (FIG. 17A) of the native valve is increased slightly, and/or the shape of the annulus is otherwise altered. Such radial force can enhance anchoring of the device 100 to resist movement toward the atrium when the valve 130 is closed during ventricular systole as well as movement toward the ventricle when the valve 130 is open. Furthermore, the resulting compression fit between the retainer 110 and leaflets and/or ventricular walls or other structures helps create a long-term bond between the tissue and the device 100 by encouraging tissue ingrowth and encapsulation.

Figure 18:
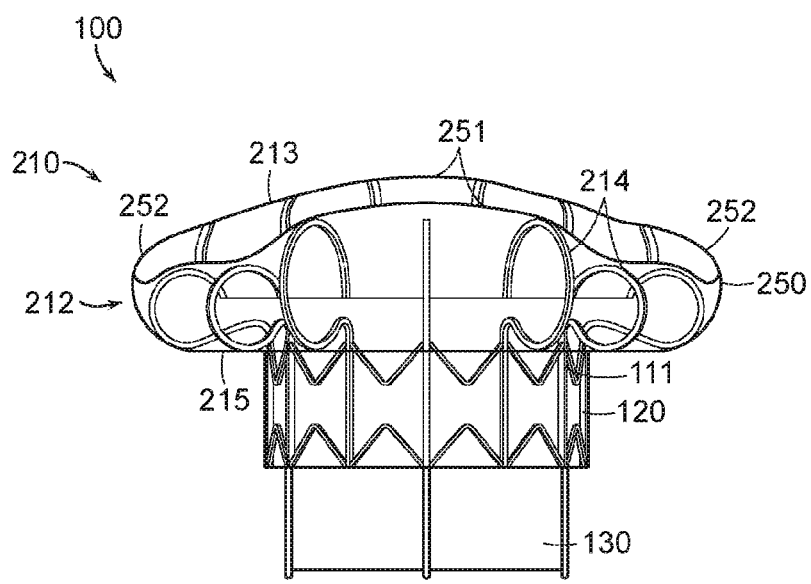
FIG. 18 is a side view of a prosthetic heart valve device shown in an expanded configuration in accordance with a further embodiment of the present technology.

FIG. 18 is a side view of a prosthetic heart valve device 100 shown in an expanded configuration 102 in accordance with a further embodiment of the present technology. The device 100 can include features generally similar to the features of the prosthetic heart valve device 100 described above with reference FIGS. 10A-17C. For example, the device 100 includes the valve support 120 and the prosthetic valve 130 housed within an interior lumen of the valve support 120. However, in the embodiment shown in FIG. 18, the device 100 includes a retainer 210 having an oval or D-shaped upstream perimeter 213 and a plurality of elevations around a circumference 250 of the retainer 210 such that the retainer 210 is suitable for engaging and conforming with tissue in the subannular region of the mitral valve.

Similar to the retainer 110 of device 100 (FIG. 10A), the tissue engaging portion 212 of the retainer 210 can be a generally outward oriented portion of the device 100. As shown in FIG. 18, the retainer 110 can include of a series of circumferentially positioned, resiliently deformable and flexible ribs 214. In other embodiments, the retainer 210 can include flexible wires or filaments arranged in a diamond pattern or configuration (not shown). The flexible ribs 214 can, in some embodiments, provide column strength sufficient to inhibit movement of the device 100 relative the annulus under the force of systolic blood pressure against the valve 130 mounted in the valve support 120.

In some embodiments, the upstream perimeter 213 of the retainer 210 does not lie in a single plane. For example, the ribs 214 can have variable lengths and/or be off-set from each other at variable angles such that a distance (e.g., elevation) between a downstream perimeter 215 and the upstream perimeter 213 can vary around the circumference 250. For example, the upstream perimeter 213 can form a rim having a plurality of peaks 251 and valleys 252 for adapting to the shape of the native mitral valve (see FIG. 5C). As used herein, "peaks" and "valleys" refers to portions of the upstream perimeter 213 having an undulating shape formed by changes in elevation with respect to the downstream perimeter 215. In some embodiments, the peak portions of the upstream perimeter 213 are about 2 to about 20 mm, or more preferably about 5 mm to about 15 mm, higher (further upstream) than the valley portions relative to a reference plane perpendicular to the direction of blood flow through the valve.

In one embodiment, the upstream perimeter 213 of the retainer 210 can have two peaks 251 that are separated by two valleys 252. In some embodiments, a first peak can have a different shape or elevation than that of a second peak. In other embodiments, the shape of a valley 252 can be different than a shape of an inverted peak 251. Accordingly, the peaks 251 and valleys 252 can be asymmetrically positioned and shaped around the circumference 250 of the retainer 210. In various arrangements, the valleys 252 can be configured for positioning along commissural regions of the native annulus, and the peaks 251 can be configured for positioning along leaflet regions of the native annulus. In one embodiment, the peaks 251 can have apices configured to be positioned near midpoint regions of the leaflets.

Although the retainer 210 is deformable in response to distorting forces exerted by the native anatomy, the valve support 120 can have sufficient rigidity to maintain a circular or other original cross-sectional shape, thus ensuring proper functioning of the prosthetic valve leaflets 132 when opening and closing. Such mechanical isolation from the retainer 210 may be achieved by the valve support 120 having sufficient rigidity to resist deformation while retainer 210 is deformed, and by selecting a location and means for coupling the valve support 120 to the retainer 210 so as to mitigate the transmission of forces through the retainer 210 to the valve support 120 or the prosthetic valve 130 contained therein. For example, the valve support 120 may be coupled to the retainer 210 only at the upstream end 121 of the valve support 120, and the retainer 110 can further extend away from the valve support in an outward and upstream direction. Thus, forces exerted on the retainer 210 by the annulus or subannular tissue can be absorbed by the flexible ribs 214 of the retainer 210 to mitigate transmission of such forces to the valve support 120.

Additional Components and Features Suitable for Use with the Prosthetic Heart Valve Devices Additional components and features that are suitable for use with the prosthetic heart valve devices (e.g., devices 100 described above) are described herein. It will be recognized by one of ordinary skill in the art that while certain components and features are described with respect to a particular device (e.g., device 100), the components and features can also be suitable for use with or incorporated with other devices as described further herein.

As discussed above with respect to FIG. 10A, some embodiments of the prosthetic heart valve device 100 can include a sealing member 140 that extends around portions of the retainer 110 and/or the valve support 120. For example, the embodiment illustrated in FIG. 10A has a sealing member 140 around the outer surface 142 of the retainer 110 and around an exterior surface 127 of the valve support 120 to prevent paravalvular leaks both between the device 100 and the anatomy but also through components of the device 100. Additionally, the sealing member 140 can be configured to promote in-growth of tissue for facilitating implantation of the device 100 in the native heart valve. In one embodiment, the sealing member can be a sleeve 146 (FIG. 10A) which can include an impermeable sealing material that is cylindrical and configured to fit within or over various frame or skeleton structures of the device 100 as further described below.

In FIG. 10A, the sleeve 146 is on the exterior surface 127 of the valve support 120; however, in other embodiments, the sleeve 146 or other sealing member 140 can be disposed on the interior surface 126 of the valve support 120. While FIG. 10A illustrates an embodiment of the device 100 in which the sleeve 146 is disposed on the outer surface 142 of the retainer 110, one of ordinary skill will recognize other configurations where the sleeve 146 can be disposed on the inner surface 141 of the retainer 110.

One of ordinary skill in the art will recognize that the sealing members 140, such as the sleeves 146, can fully cover the surfaces 126, 127, 141 and 142 or in other embodiments, at least partially cover the surfaces 126, 127, 141 and 142 of the retainer 110 and the valve support 120, respectively. Any combination of sealing members 140 is contemplated. Additionally, the sealing member 140 can comprise a single continuous sheet of fluid impervious material (e.g., for covering a surface 141, 142 of the retainer 110 and a surface 126, 127 of the valve support 120), which could create a seal between the retainer 110 and the valve support 120. In various embodiments, the sealing member 140, such as the sleeve 146, can comprise a fabric or other flexible and biocompatible material such as Dacron®, ePTFE, bovine pericardium, or other suitable flexible material to integrate with tissue and minimize paravalvular leaks. In other embodiments, the sealing member 140 can include a polymer, thermoplastic polymer, polyester, Gore-Tex®, a synthetic fiber, a natural fiber or polyethylene terephthalate (PET). The valve 130 may also be attached to the sealing member 140 or integrally formed with the sealing member 140.

Figure 19:
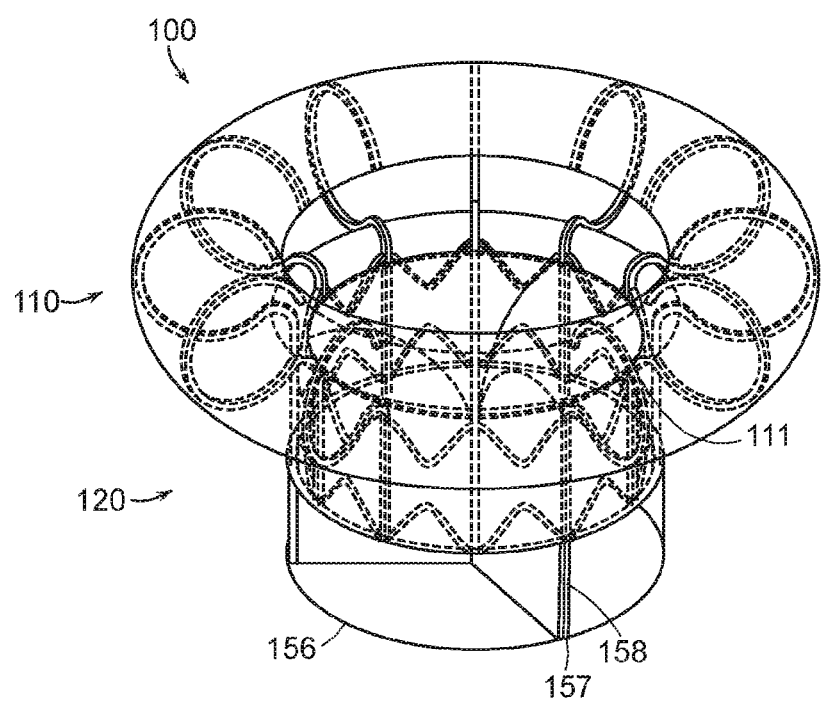
FIG. 19 is an isometric view of the prosthetic heart valve device having a connecting ring in accordance with an embodiment of the present technology.

The prosthetic heart valve device 100 can also include additional support features for maintaining a desired shape and/or rigidity of the valve support 120 or the retainer 110. FIG. 19 is an isometric view of the prosthetic heart valve device 100 having a connecting ring 156 in accordance with an embodiment of the present technology. As shown in FIG. 19, the connecting ring 156 can be coupled to plurality of commissure posts 158 integrated and/or coupled to the valve support 120. As shown in FIG. 19, the connecting ring 156 can be coupled to the downstream ends 157 of the commissure posts 158; however, the connecting ring 156 may also be coupled to another portion of the commissure posts 158 or the valve support 120. The connecting ring 156 can have a variety of symmetrical or non-symmetrical geometrical cross-sections and can provide support for the commissure posts 158 to keep the posts from bending or deforming.

Figure 20A:
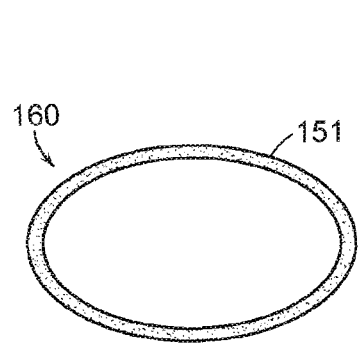
FIGS. 20A-20B are isometric views of a retainer support ring and the prosthetic heart valve device having the retainer support ring in accordance with an additional embodiment of the present technology.
Figure 20B:
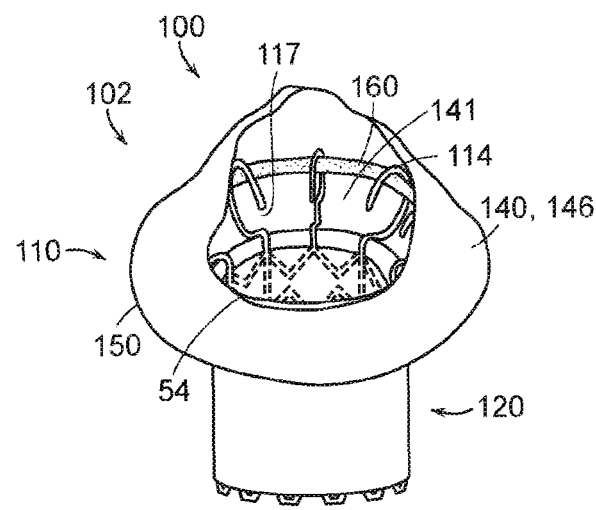
Figure 21:
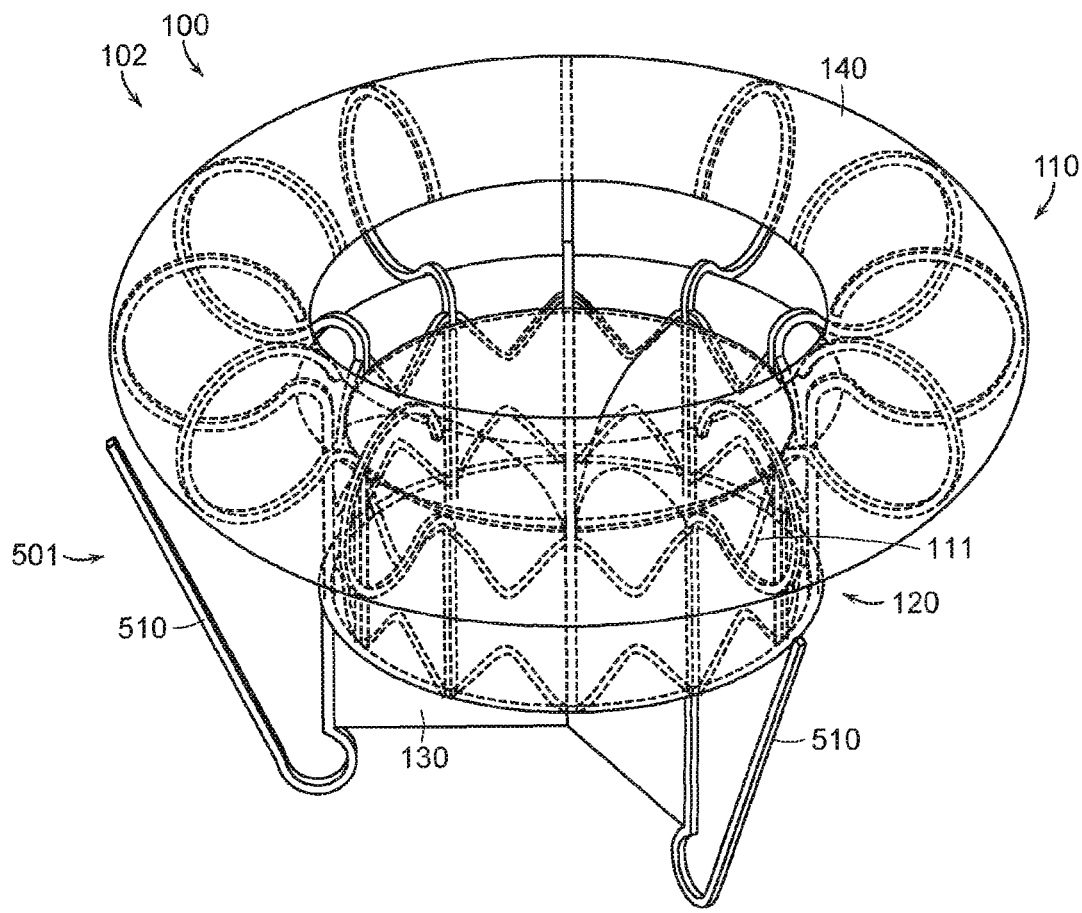
FIG. 21 is an isometric view of a prosthetic heart valve device in an expanded configuration and having a plurality of stabilizing elements in accordance with an embodiment of the present technology.

FIGS. 20A-20B are isometric views of a retainer support ring 160 and the prosthetic heart valve device 100 having the retainer support ring 160 in accordance with an additional embodiment of the present technology. As shown in FIG. 20A, the retainer support ring 160 can be a circular-shaped ring element that has a ring circumference 151 approximately similar to a desired circumference 150 of the retainer 110 when the device 100 is in the expanded configuration 102. In another embodiment, not shown, the support ring 160 can have a different shape (e.g., oval, D-shaped, irregular, etc.) such that the support ring 160 can be configured to encourage the retainer 110 into the different shape. In one embodiment, the support ring 160 can be formed from a shape memory material (e.g., nitinol) that can collapse in a delivery configuration (not shown) to fit within a delivery catheter, and to expand toward the ring circumference 151 when the device 100 is deployed at the target location at or near the native heart valve. In other embodiments, the retainer support ring 160 may be a solid, coiled, or woven wire or band of a flexible, resilient material (e.g., biocompatible polymers or metals) with the desired degree of rigidity.

In FIG. 21B, the sealing member 140, such as the sleeve 146, is pulled away for clarity only to expose the retainer support ring 160 disposed within the inner surface 141 of the retainer 110. For example, the support ring 160 can be configured to be disposed in the openings 117 of the C-shaped ribs 114 of the retainer 110 to provide additional circumferential support for the retainer 110, enhance radial rigidity and to resist and distribute distorting forces exerted on the retainer 110 during and after delivery of the device 100.

Prosthetic Heart Valve Devices Having Stabilizing Members

Figure 22:
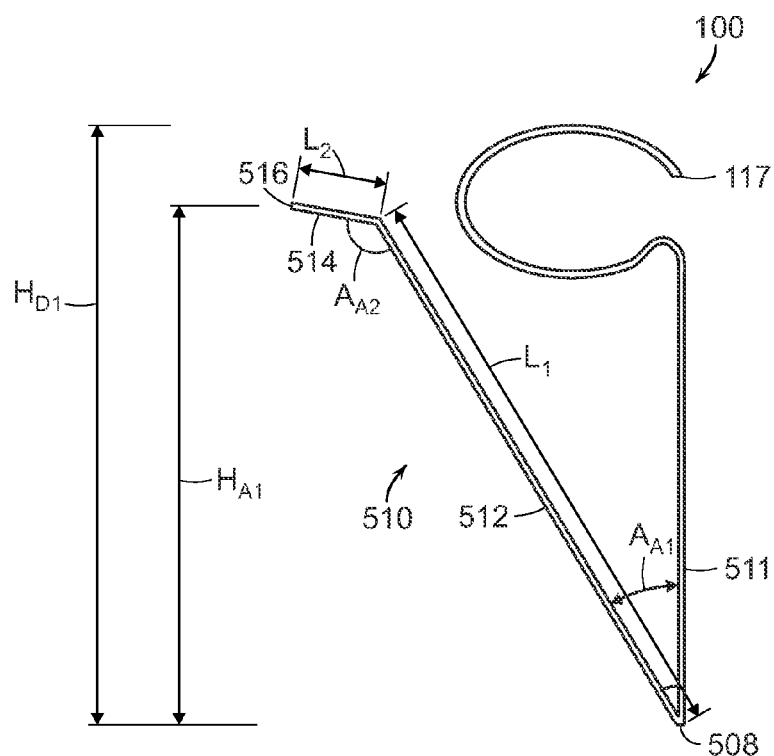
FIG. 22 is an enlarged schematic, side view of a prosthetic heart valve device having an extended arm in accordance with an embodiment of the present technology.

FIG. 22 illustrates one embodiment of the prosthetic heart valve device 100 in an expanded configuration 102 that further comprises one or more stabilizing members 501 to help stabilize the device 100 at the native valve site and, in some embodiments, prevent tilting or lateral migration, or to inhibit upstream or downstream migration of the device 100. In some embodiments, the stabilizing members 501 may comprise one or more arms 510 extending from a lower or downstream end 123 of the valve support 120, or from the commissure posts 158. In another embodiment, the arms 510 can be configured to extend from a downstream end of rib posts 88 (shown in FIG. 22). The arms 510 are configured to engage the native tissue, e.g. the valve leaflets, subannular tissue, or ventricular wall, either inside or outside the native leaflets, depending on the configuration.

Figure 23A:
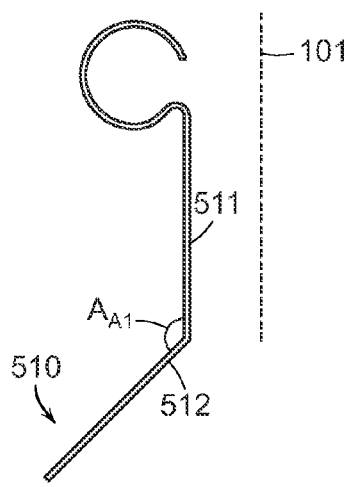
FIGS. 23A-23C are enlarged partial side views of a prosthetic heart valve device having arms coupled to the device at various angles with respect to a longitudinal axis of the device in accordance with further embodiments of the present technology.
Figure 23B:
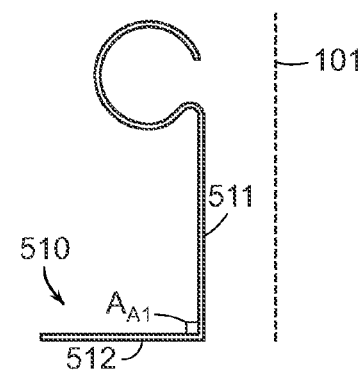
Figure 23C:
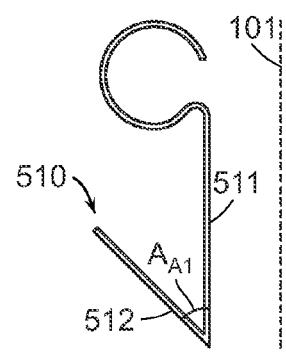

FIG. 22 is an enlarged schematic, side view of a prosthetic heart valve device 100 having an extended arm in accordance with an embodiment of the present technology. As shown in FIG. 22, an individual arm 510 may comprise an arm body 512, an arm extension 514, and an arm tip 516. The arm body 512 has an arm body length $L_1$ and may connect to a post 511 at a first joint 508. The post 511 can be a valve support post 122, a retainer rib post 88, and/or another feature of the device 100 (e.g., a commissure post 158). In one embodiment, the arm body 512 may be welded, bonded, crimped, or otherwise mechanically attached to the post 511 the first joint 508. Alternatively, arms 510 may be integrally formed with posts 511, such as the valve support posts 122 or the rib posts 88. A first arm angle $A_{A1}$ is formed by the intersection of the axes of post 511 and the arm body 512 and is selected such that the arm 512 is positionable so that the tip 516 can engage the native tissue at a desired location, e.g. the subannular tissue or ventricular wall behind the native leaflets. FIGS. 23A-23C are enlarged partial side views of a prosthetic heart valve device 100 having arms 510 coupled to the device at various angles with respect to a longitudinal axis 101 of the device 100 in accordance with further embodiments of the present technology. In one embodiment, the first arm angle $A_{A1}$ can be about 10° to about 45°. In other embodiments, the first arm angle $A_{A1}$ can be an obtuse angle (FIG. 23A), generally perpendicular or approximately a 90° angle (FIG. 23B), or an acute angle (FIG. 23C).

Referring back to FIG. 22, the arm body 512 can connect to the arm extension 514 at a distal end of the arm body 512. The arm extension 514 can have an arm extension length $L_2$ which can be selected or optimized for penetrating a desired distance into the native tissue, such as about 0.5-2 mm. The arm extension 514 can extend from the arm body 212 at second arm angle $A_{A2}$. The second arm angle $A_{A2}$ can be formed by the intersection between the arm extension 514 and arm body 512 and be selected to provide the desired angle of engagement with the native tissue, such as about 100° to about 135°. In other embodiments, the arm extension 514 may be parallel or collinear with the arm body 512 (not shown), or may be eliminated entirely. The arm extension 514 terminates at the arm tip 516. In embodiments without an arm extension 514, the arm tip 516 can be the most distal portion of the arm body 512 (not shown).

Figure 24A:
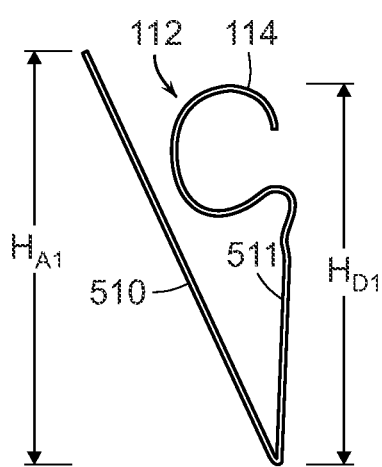
FIGS. 24A-24C are enlarged, partial side views of a prosthetic heart valve device having arms of various lengths coupled to the device in accordance with additional embodiments of the present technology.
Figure 24B:
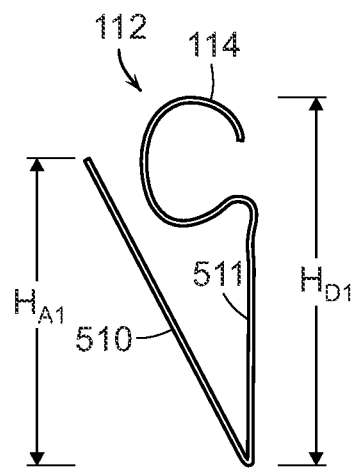
Figure 24C:
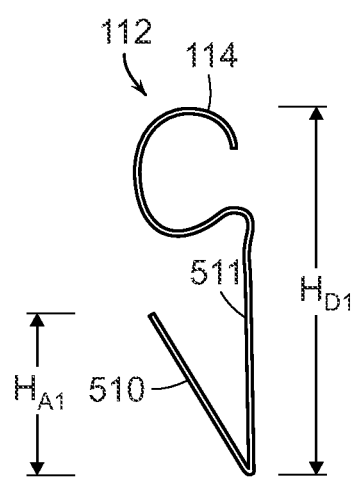

The arm 510 may have an arm height $H_{A1}$ extending from the first joint 508 to the most distal reaching point of the arm, which could be the arm tip 516 (shown in FIG. 22) along an axis parallel to the longitudinal axis 101 of the device 100. The arm height $H_{A1}$ can be selected or optimized such that the arm tip 516 engages a desired location in the subannular anatomy when the device 100 is in a desired longitudinal position relative to the native mitral valve (e.g., when the retainer 110 is in engagement with the subannular tissue). The arm height $H_{A1}$ will depend upon of the overall height of the retainer 110 and/or valve support 120 as well as the location of the joint 508. FIGS. 24A-24C are enlarged, partial side views of prosthetic heart valve devices having arms 510 of various lengths ($L_1+L_2$), and accordingly having variable heights $H_{A1}$. As shown, the arm height $H_{A1}$ may be greater than the overall height $H_{D1}$ of the device 100 (represented by the post 511 and rib 114) (FIG. 24A), be intermediate between the respective heights $H_{D1}$, $H_{V1}$ of the retainer 110 (represented by the tissue engaging portion 112 of the rib 114) and the valve support 120 (represented by post 511) (FIG. 24B), or be less than the overall height $H_{D1}$ of both the retainer 110 (represented by rib 114) and the valve support 120 (FIG. 24C).

Additional details and embodiments regarding the structure and attachment of arms or other stabilizing members suitable for use with the device 100 can be found in International PCT Patent Application No. PCT/US2012/043636, entitled "PROSTHETIC HEART VALVE DEVICES AND ASSOCIATED SYSTEMS AND METHODS," filed Jun. 21, 2012, the entire contents of which are incorporated herein by reference.

Figure 25A:
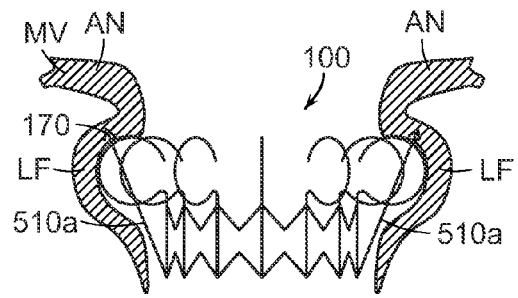
FIGS. 25A-25E are cross-sectional views of a heart with an implanted prosthetic heart valve device having arms disposed on an inward-facing surface of the leaflets in accordance with various embodiments of the present technology.
Figure 25B:
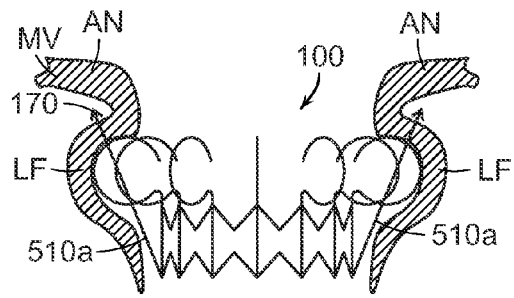
Figure 25C:
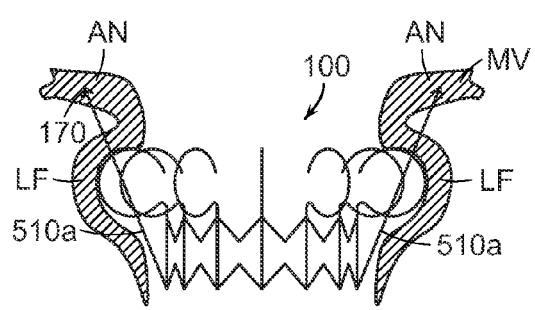
Figure 25D:
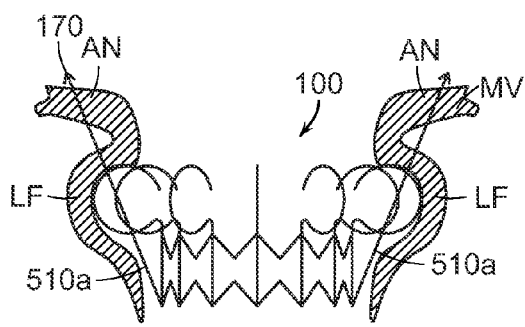
Figure 25E:
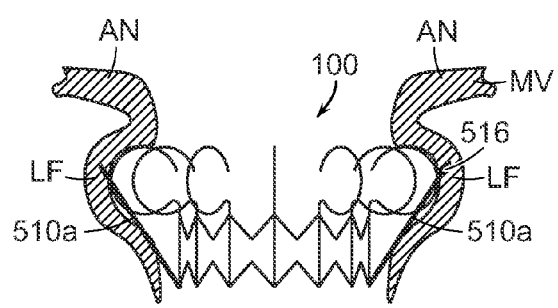

FIGS. 25A-25E are cross-sectional views of a heart with an implanted prosthetic heart valve device 100 having arms 510a disposed on an inward-facing surface of the leaflets LF. The embodiments of prosthetic heart valve devices 100 illustrated in FIGS. 25A-25E have arms 510a configured to expand to a position radially inside the leaflets LF, radially outside the leaflets LF, or a combination of inside and outside the leaflets LF. For example, FIG. 25A shows the arms 510a expanding and engaging an inward surface of the leaflets LF and shows the arms 510a partially piercing the leaflets LF. In another example illustrated in FIG. 25B, the arms 510a may fully penetrate the leaflets LF. In a further example, the device 100 can incorporate arms 510a that 1) completely penetrate the leaflets LF and 2) partially pierce subannular tissue (FIG. 25C). Referring to FIG. 25D, the device 100 can be configured to incorporate arms 510a that fully penetrate both the leaflets LF and the annular tissue of the mitral valve MV. In an additional example, FIG. 25E shows the arms 510a radially engaging a greater length of the leaflet LF along the arm 510a as well as optionally piercing the leaflet LF and/or annular tissue AN at the arm tip 516. In some embodiments, all or a portion of the arms 510a may have a curvature or other suitable shape which allows the leaflets LF to conform to the outer surface of the arms 510a.

FIGS. 26A-26C are schematic views illustrating various embodiments of tissue engaging elements 170 for use with prosthetic heart valve devices 100 in accordance with the present technology. Tissue engaging elements 170 can include any feature that engages tissue in an atraumatic manner, such as a blunt element, or which partially pierces or fully penetrates cardiac tissue, such as a barb or spike. As used herein, "tissue engaging" refers to an element 170 which exerts a force on the tissue T but does not necessarily pierce the tissue T, such as being atraumatic to the tissue T, as shown in FIG. 26A. As used herein, "partially piercing" refers to a tissue engaging feature 170 which at least partially penetrates the tissue T but does not break through an opposite surface S, as shown in FIG. 26B. As used herein, "fully piercing" refers to a tissue engaging feature 170 which can both enter and exit the tissue T, as shown in FIG. 26C. "Piercing" alone may refer to either partial or full piercing. Tissue engaging elements 170 may take the form of spikes, barbs, or any structure known in art capable of piercing cardiac tissue, or alternatively, any blunt or atraumatic feature configured to apply pressure on the cardiac tissue without piercing the tissue. Further details on positioning of such elements are described herein.

FIGS. 27A-27C are enlarged, partial side views of a prosthetic heart valve device 100 having arms 510a with tissue engaging elements 170 configured to engage an inward-facing surface of the leaflets in accordance with various embodiments of the present technology. As illustrated in FIGS. 27A-27C, tissue engaging elements 170 can be incorporated on and extend from the arms 510a in either a downstream direction (FIG. 27A), upstream direction (FIG. 27B), or in both the downstream and upstream directions (FIG. 27C). In other embodiments, the tissue engaging elements 170 can be incorporated on and extend from the components of the retainer 110 and/or the valve support 120 in either or both the upstream and downstream directions.

Figure 28A:
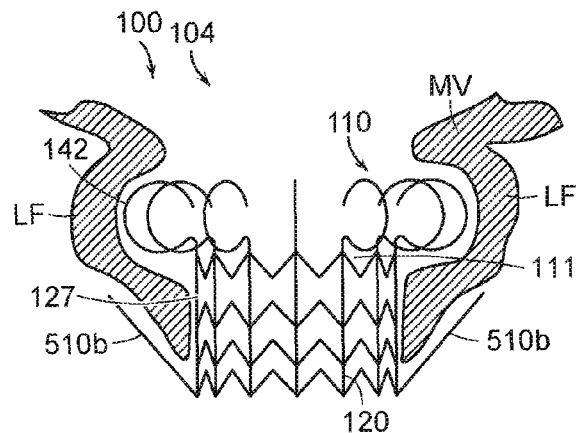
FIGS. 28A-28B are side views showing prosthetic heart valve devices implanted at a mitral valve MV (illustrated in cross-section) in a deployed configuration, wherein the devices have arms for engaging an outward-facing surface of the native leaflets in accordance with further embodiments of the present technology.
Figure 28B:
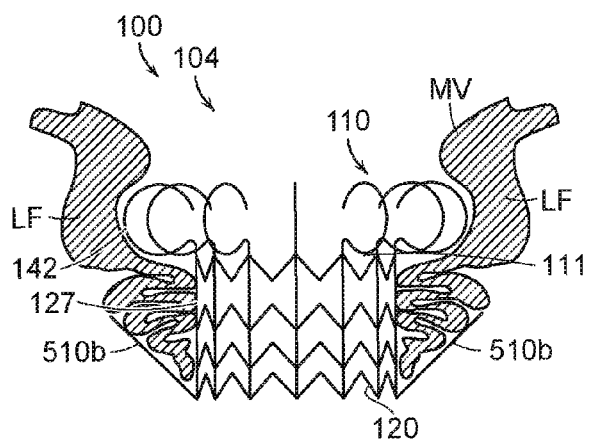
Figure 28C:
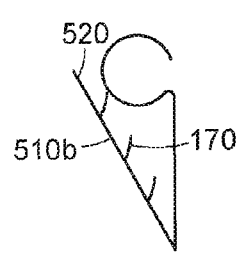
FIG. 28C is an enlarged, partial side view of a prosthetic heart valve device having an arm with tissue engaging elements configured to engage an outward-facing surface of the leaflets in accordance with another embodiment of the present technology.

FIGS. 28A-28B are side views showing prosthetic heart valve devices 100 implanted at a mitral valve MV (illustrated in cross-section) in a deployed configuration 104, wherein the devices have arms 510b for engaging an outward-facing surface of the native leaflets LF in accordance with various embodiments of the present technology. FIG. 28A shows an embodiment of the device 100 that includes arms 510b configured to reach behind the leaflets LF such that the leaflets LF are effectively sandwiched between the arms 510b and the outer surface 142 of the retainer 110 and/or the exterior surface 127 of the valve support 120. In another embodiment, and as shown in FIG. 28B, the arms 510b may cause leaflets LF to fold upon themselves in the space between the arms 510b and the outer surface 142 of the retainer 110 and/or the exterior surface 127 of the valve support 120. FIG. 28C is an enlarged, partial side view of a prosthetic heart valve device 100 having the arm 510b with tissue engaging elements 170 configured to engage an outward-facing surface of the leaflets in accordance with various embodiments of the present technology. As shown in FIG. 28C, the arm 510b includes tissue engaging elements 170 on an inside surface 520 of the arm 510b such that they are oriented toward the leaflet tissue.

Figure 29A:
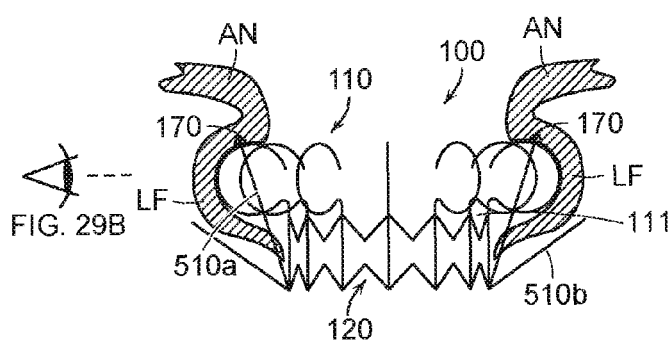
FIG. 29A is a side view of a prosthetic heart valve device and shown implanted at a mitral valve (illustrated in cross-section), the device having arms for engaging an outward-facing surface of the native leaflets and arms for engaging an inward-facing surface of the native leaflets in accordance with an additional embodiment of the present technology.
Figure 29B:
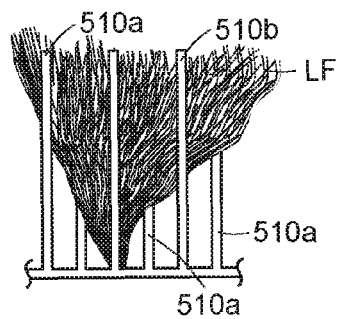
FIG. 29B is an enlarged view of the arms engaging the inward-facing and outward-facing surfaces of the leaflets as shown in FIG. 29A.

In accordance with another embodiment of the present technology, FIG. 29A is a side view showing a prosthetic heart valve device 100 implanted at a mitral valve MV (illustrated in cross-section). The device shown in FIG. 29A has arms 510b for engaging an outward-facing surface of the native leaflets LF and arms 510a for engaging an inward-facing surface of the native leaflets LF. Inside/outside arms 510a, 510b may further comprise tissue engaging elements 170 on a radially inside surface or radially outside surface of the arms 510a, 510b, respectively, for engaging or piercing the leaflet tissue. The arrangement of inside/outside arms 510a, 510b around a circumference of the device 100 can alternate in a pre-designed pattern. For example, inside arms 510a can alternate with outside arms 510b as shown in FIG. 29B, or alternatively, arms 510a, 510b may extend radially outward and/or radially inward randomly or at irregular intervals, depending on placement of the device 100 and with respect to alignment with the native posterior and anterior leaflets.

Figure 30D:
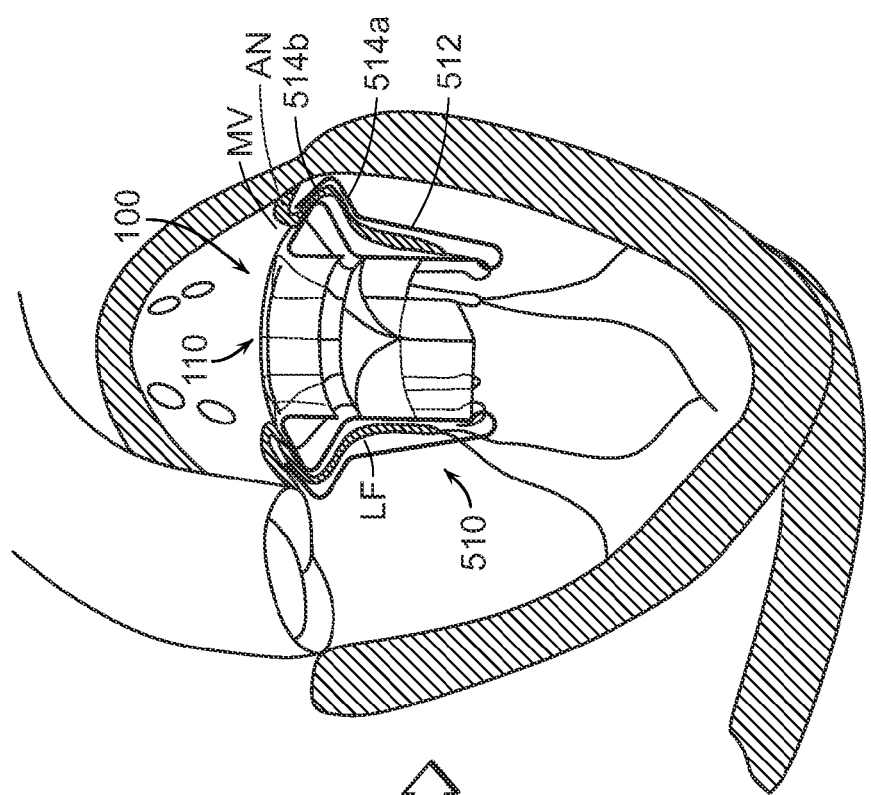
Figure 30C:
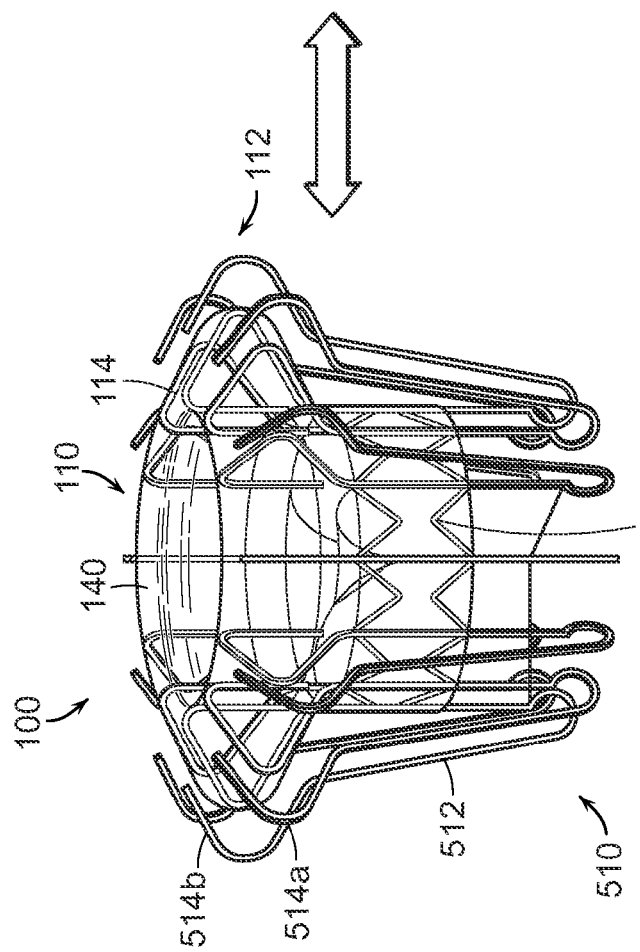

FIGS. 30A and 30C are isometric views of the prosthetic heart valve device 100 having arms 510 with a similar profile as a profile of the retainer 110, and FIGS. 30B and 30D are side views of the prosthetic heart valve devices 100 of FIGS. 30A and 30C, respectively, and shown implanted at a mitral valve (illustrated in cross-section) in accordance with another embodiment of the present technology. As shown in FIG. 30A, the arms 510 can have a similar overall profile as a profile of the retainer 110. The retainer 110 can include ribs 114 having varying shapes, sizes and/or outwardly or inwardly oriented tissue engaging portion segments 80, 86 for forming the overall retainer 110 profile. Accordingly, the arms 510 can also have varying shapes, sizes and/or outwardly or inwardly oriented arm segments that mimic the retainer 110 profile. In the embodiment shown in FIGS. 30A-30B, the arms 510 are configured to clamp leaflets LF and/or the annulus AN tissue between the arms 510 and the tissue engaging portion 112 of the ribs 114 so as to conform the leaflet tissue to the shape of the retainer 110 for enhanced sealing and anchoring of the device 100. For example, FIG. 30A illustrates one embodiment in which the arm extensions 514 and/or the arm bodies 512 may partially mimic the shape of the ribs 114 and/or the tissue engaging portion segments 80, 86.

FIGS. 30C-30D illustrates another embodiment in which first and second arm extensions 514a and 514b and/or arm bodies 512 more closely follow the shape of the ribs 114. For example, the arms 510 can include the arm body 512 and multiple arm extensions (e.g., first arm extension 514a and second arm extension 514b) that are configured to clamp leaflets LF and/or the annulus AN tissue between the arms 510 and the tissue engaging portion 112 of the ribs 114 so as to conform the leaflet tissue to both lower and upper regions of the tissue engaging portion 112 for enhanced sealing and anchoring of the device 100. Embodiments encompassed by FIGS. 30A-30D can apply to outward surface engaging arms 510b and/or inward surface engaging arms 510a.

Figure 31A:
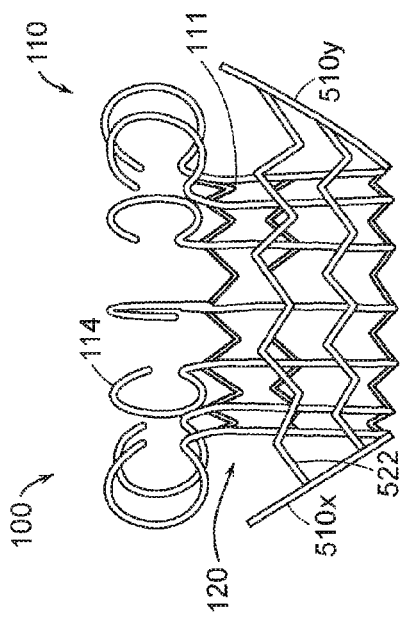
FIG. 31A is a side view of a prosthetic heart valve device having a plurality of non-interconnected arms in accordance with a further embodiment of the present technology.
Figure 31B:
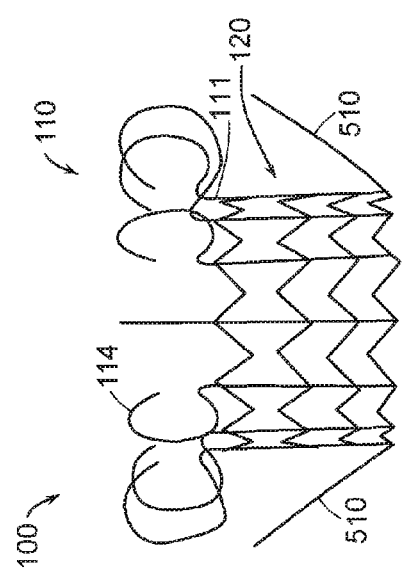

In some embodiments, the prosthetic heart valve device 100 may incorporate a plurality of arms 510 around a circumference of the device 100; however, in other embodiments, the device 100 may include the plurality of arms in groupings (e.g., first and second groupings so as to engage the posterior and anterior leaflets, respectively). Additionally, the arms 510 may extend from the retainer 110 and/or valve support 120 independently of other components including other arms 510, such as shown in FIG. 31A. In other embodiments and as shown in FIG. 31B, the device 100 may further include at least one first arm 510x interconnected with at least one second arm 510y by interconnecting arm struts 522. The arm struts 522 can be configured to be circumferentially expandable and may connect all arms 510 (e.g., arm 510x and 510y) or one or more groups of arms 510. In some embodiments, the arm struts 522 can limit the outward extension of the arms 510x, 510y away from the device 100.

Figure 32A:
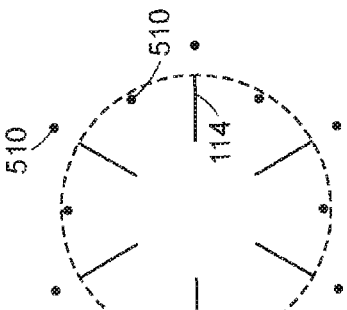
Figure 32B:
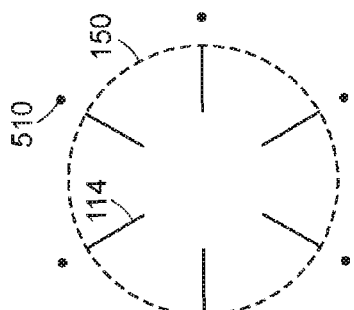
FIG. 32B is a side view of a prosthetic heart valve device having a plurality of circumferentially connected arms in accordance with a further embodiment of the present technology.
Figure 32C:
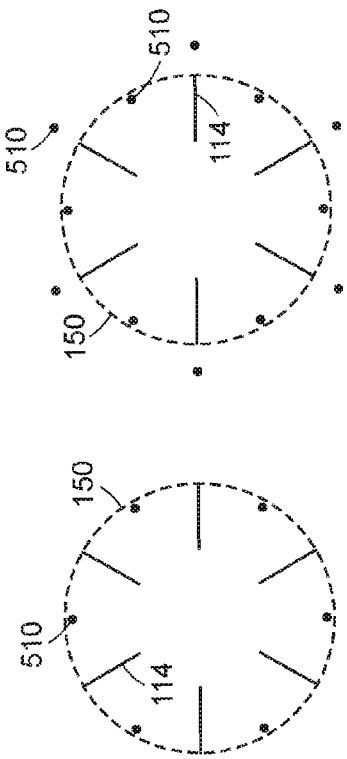
Figure 32D:
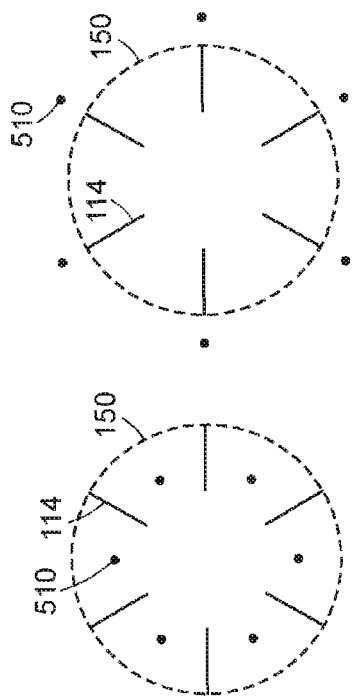

In accordance with aspects of the present technology, the arms 510 can be coupled to and/or extend from components of the device 100 symmetrically and/or asymmetrically around the circumference 150 of the device 100. FIGS. 32A-32D are schematic top views of arm location patterns with respect to the ribs 114 of the retainer 110 (e.g., as shown in FIG. 31A). The arms 510 can be interspersed with ribs 114 (FIGS. 32A and 32C), in the same radial plane as the ribs 114 of the retainer 110 (FIG. 32B), or both interspersed and in plane with the ribs 114 (FIG. 32D). Further, the arms 510 may be configured to extend outside the expanded outer circumference 150 of the retainer 110 (FIG. 32B), inside the expanded outer circumference 150 of the retainer 110 (FIG. 32A), extend to the same outer circumference 150 of the retainer 110 (FIG. 32C), or a combination of these configurations (FIG. 32D).

In the above-described embodiments, the arms 510 may be configured to engage tissue independently of the deployment of retainer 110. For example, delivery catheters suitable for the delivery of the prosthetic heart valve devices 100 may be equipped with separate mechanisms operable to deploy the arms 510 and the retainers 110 individually or otherwise independently of each other. In this way, the retainer 110 may be first released into engagement with the native tissue so that the position of device 100 may be assessed and adjusted by the operator until the desired final position has been attained. Following deployment and positioning of the retainer 110, the arms 510 can be released to engage the tissue. Such deployment systems and methods are useful when the arms 510 are equipped with tissue engaging elements 170 which, once deployed, may prohibit any repositioning of the device 100. In some embodiments, the retainer 110 will be equipped with atraumatic tissue engagement elements 170 which do not penetrate tissue or inhibit device relocation once the retainer 110 has been deployed. Accordingly, some embodiments of the device 100 may be repositionable even with the retainer 110 expanded so long as the arms 510 are constrained in an undeployed configuration, with the device 100 becoming permanently anchored only when the arms 510 are released.

Figure 33A:
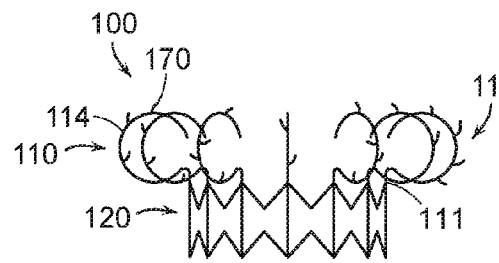
FIGS. 33A-33E are side views of prosthetic heart valve devices having tissue engaging elements on varying structures of the device in accordance with additional embodiments of the present technology.
Figure 33B:
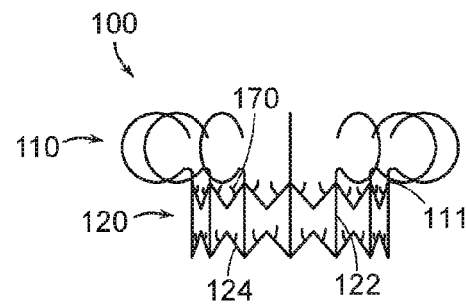
Figure 33C:
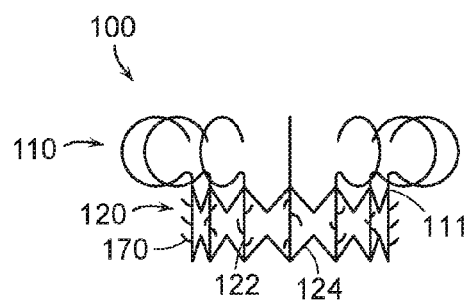
Figure 33D:
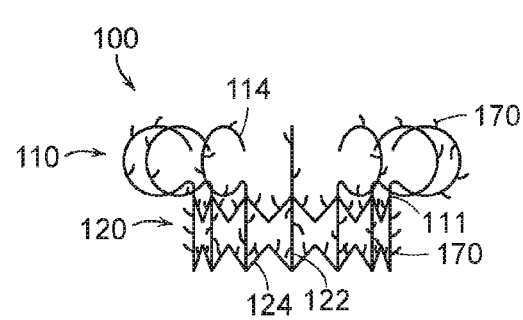

Alternatively or in addition to tissue engaging elements 170 present on the arms 510 as described above, tissue engaging elements 170 may be present on other components of the device 100. FIGS. 33A-33E are side views of prosthetic heart valve devices 100 having tissue engaging elements 170 on varying structures of the device 100 in accordance with additional embodiments of the present technology. FIG. 33A shows tissue engaging elements 170 incorporated on the tissue engaging portion 112 of the ribs 114 of the retainer 110. FIG. 33B illustrates an embodiment of the device 100 having the tissue engaging elements 170 along the struts 124 of the valve support 120. Likewise, FIG. 33C shows an embodiment of the device 100 having the tissue engaging elements 170 along the posts of the valve support 120. In another embodiment, shown in FIG. 33D, the tissue engaging elements 170 can be incorporated along the surfaces of several device components, such as the ribs 114 as well as the posts 122 and struts 124 of the valve support 120.

The tissue engaging elements 170 are shown in FIGS. 33A-33D schematically, but one of ordinary skill in the art will recognize that the elements can be any of a variety of tissue engaging elements 170 described herein (e.g., atraumatic, partially piercing, fully penetrating, etc.), or in other embodiments, a combination of different types of tissue engaging elements 170. Additionally, the tissue engaging elements 170 are shown oriented in an upstream direction (e.g., to inhibit upstream migration of the device 100) in FIGS. 33A-33B; however, in other embodiments, the tissue engaging elements 170 can be oriented in a downstream direction (e.g., to inhibit downstream migration of the device 100), or in a combination of downstream and upstream oriented directions (shown in FIGS. 33C-33D). The tissue engaging elements 170 can be incorporated symmetrically around a circumference or outside surface of the device 100, or in other embodiments, the tissue engaging elements 170 can be incorporated asymmetrically. For example, in some embodiments, the tissue engaging elements 170 can be present on a side of the device 100 aligned with the posterior leaflet, but be absent or have a different arrangement on a side of the device 100 aligned with the anterior leaflet such that the wall separating the aortic valve from the left ventricle will not be affected by the tissue engaging elements 170.

Figure 33E:
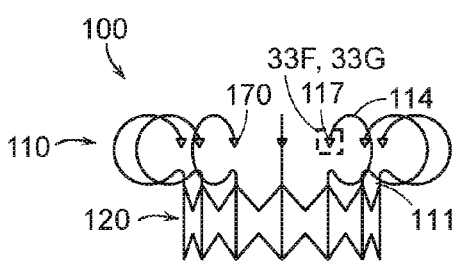
Figure 33F:
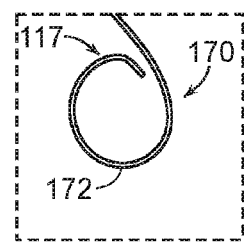
Figure 33G:
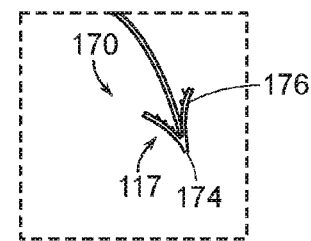

FIG. 33E illustrates an embodiment of the device 100 having tissue engaging elements 170, such as spikes on a rib tip 117 of the rib 114, wherein the spikes 174 can be configured to fully or partially penetrate subannular tissue when the device 100 is deployed on or under the annulus of the mitral valve. In some embodiments, the tissue engaging elements 170 (e.g., spikes) can include barbs 176 or other features for retaining the tissue engaging elements 170 (e.g., spikes) in the tissue. In other embodiments, the tissue engaging elements 170 (e.g., spikes) can be blunt so as to engage but not penetrate the subannular tissue. FIGS. 33F-33G are enlarged side views of tissue engaging elements 170 (e.g., hooks, spikes, etc.) suitable for use on rib tips 117 of the ribs 114. In one embodiment, shown in FIG. 3F, the rib tip 117 may include a rounded hook 172 that may partially pierce other fully penetrate cardiac tissue at the target location with the retainer 110 is deployed. In another embodiment, shown in FIG. 33G, the rib tip 117 may include a barbed protrusion such as a spike 174, 176 for piercing cardiac tissue at the target location.

Alternatively, tissue engaging elements 170, such as bumps, ridges, or other protrusions configured to exert frictional forces on cardiac tissue, may be also present on one or more valve support struts 124, valve support posts 122, and/or other components (e.g., sealing members 140). These tissue engaging elements 170 can be disposed on an outer portion of these features and can be configured to extend outwardly to engage the native leaflets and to stabilize and firmly anchor the device 100 in the desired location. Alternatively, ridges, scales, bristles, or other features having directionality may be formed on the surface of the ribs 114 or sealing member 140 to allow movement relative to native tissue in one direction, while limiting movement in the opposite direction.

Figure 34B:
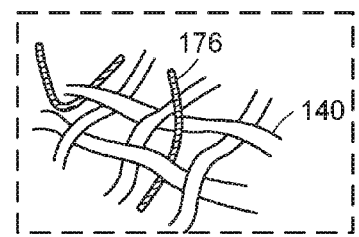
FIGS. 34A-34B are an isometric view and an enlarged detail view of a prosthetic heart valve device having a sealing member configured with tissue engaging elements in accordance with another embodiment of the present technology
Figure 34A:
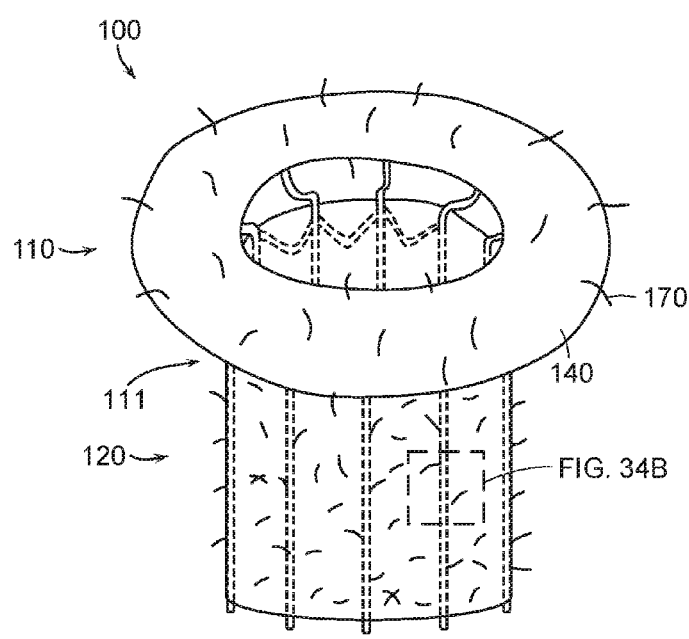

In accordance with another embodiment of the prosthetic treatment device 100, tissue engaging elements 170 can be incorporated into sealing members 140 (e.g., sleeve 146). FIGS. 34A-34B are an isometric view and an enlarged detail view of a prosthetic heart valve device 100 having a sealing member 140 configured with tissue engaging elements 170. Referring to FIGS. 34A-34B together, the tissue engaging elements 170 can comprise metallic or polymeric wires 178 or fibers, rigid and sharp enough to penetrate tissue, which are woven into or otherwise coupled to sealing member 140 materials. The sealing member 140 can then be attached to outer and/or inner surfaces 141, 142 of the retainer 110 and/or interior and/or exterior surfaces 126, 127 of the valve support 120 such that tissue engaging elements 170 extend radially outward from the sealing member 140 to engage the adjacent leaflets or other tissue.

Figures 35A, 35B, 35C, 35D:
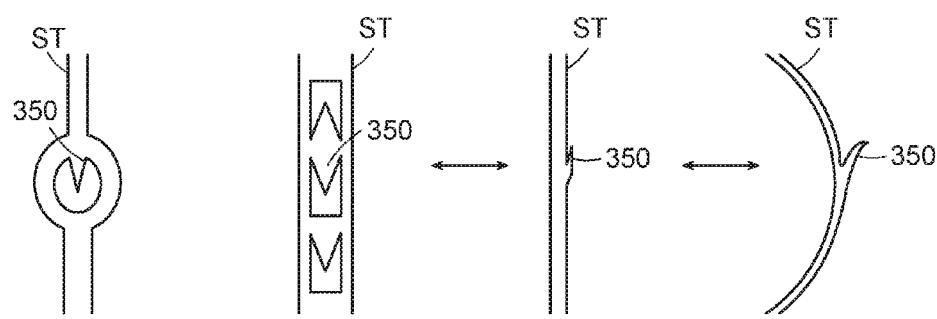
FIGS. 35A-35F are enlarged side views of embodiments of tissue engaging elements suitable for use with prosthetic heart valve devices in accordance with additional embodiments of the present technology.
Figure 35E:
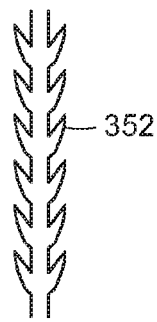
Figure 35F:
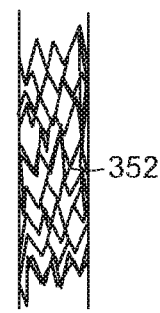

FIGS. 35A-35F are enlarged side views of embodiments of additional tissue engaging elements that can be incorporated on various device structures (referred collectively as "ST"), such struts, posts, arms, and/or ribs which may be incorporated into device features, such as the retainer 110 or valve support 120. For example, the additional tissue engaging elements may comprise one or more cut-out protrusions 350 (FIGS. 35A and 35B) in place of or in addition to tissue engaging elements 170. In a collapsed or straightened configuration, as shown by the side view of FIG. 35C, cut-out protrusion 350 maintains low relief relative to the surface of structure ST to maintain a low profile during delivery. As the device 100 expands and structure ST changes to its deployed configuration (e.g. a curvature as shown in FIG. 35D), the protrusion separates from the ST to a higher relief. The protrusion 350 may also be configured to grab subannular tissue, pulling the cut-out protrusions even farther away from structure ST. The device structures ST may also be shaped to include sharp protrusions 352 along one or more of its edges or faces, as illustrated in FIG. 35E, or may also include pointed scale-like protrusions 354, as shown in FIG. 35F.

Prosthetic Heart Valve Devices Having Atrial Extension Members

Figure 36A:
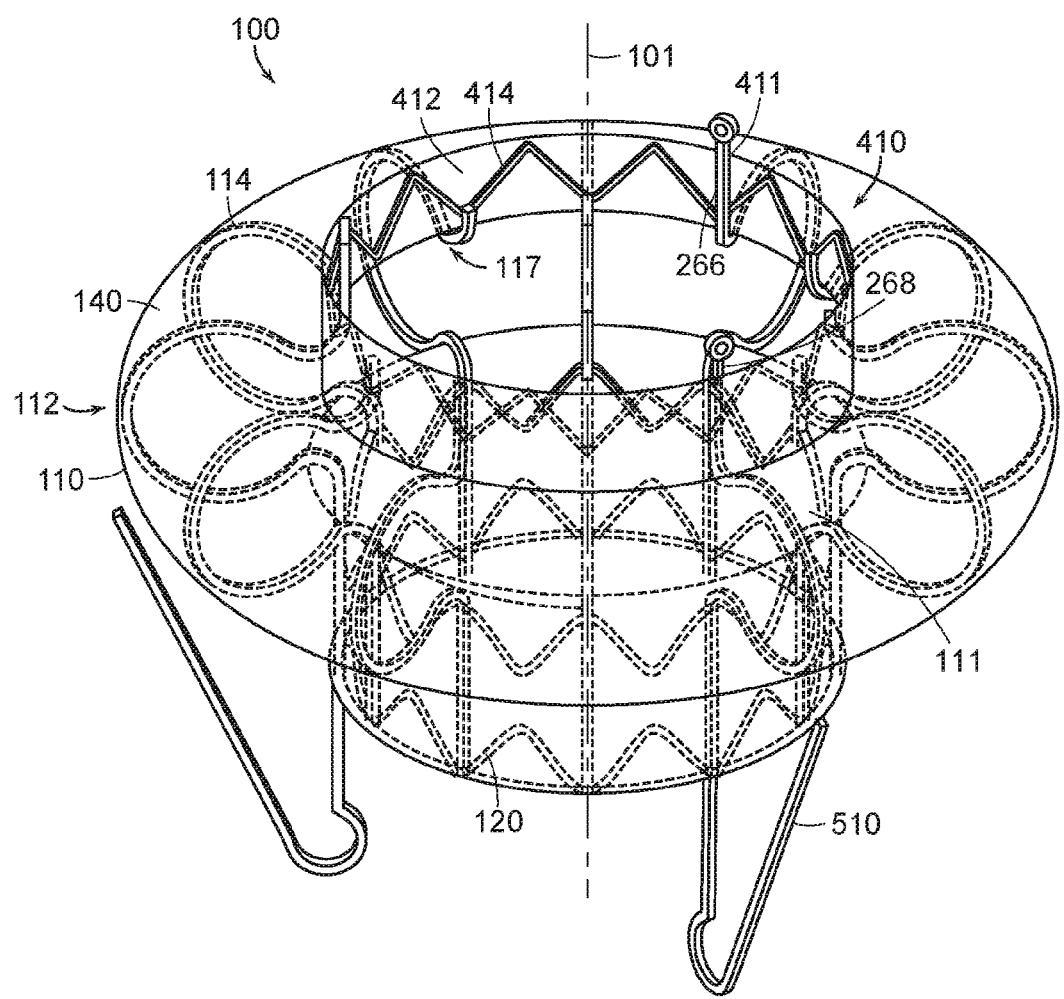
FIG. 36A is an isometric view of a prosthetic heart valve device 100 having an atrial extension member 410 in accordance with various embodiments of the present technology.

FIG. 36A is an isometric view of a prosthetic heart valve device 100 having an atrial extension member 410 in accordance with various embodiments of the present technology. The atrial extension member 410 can be generally cylindrical, being formed around the longitudinal axis 101 of the device 100 with a circular, oval, elliptical, kidney-shaped or other suitable cross-section. As shown in FIG. 36A, the atrial extension member 410 can be coupled to the retainer ribs 114, to the posts 122 of the valve support 120, or to some other device component. In one embodiment, the atrial extension member 410 can be formed by extension 411 of the ribs 114 in an upward direction. The atrial extension member 410 can include an upstream portion 412 formed by the extension 411 of the ribs 114 and including interconnecting struts 414 and/or other posts which can be arranged in a variety of geometric patterns (e.g., chevron, diamond, etc.) for support and resilience of the atrial extension member 410. The atrial extension member can be configured to extend into an intra-annular, supra-annular or atrial location in the heart to provide additional support to the device 100 and/or prevent the device 100 from moving in a downstream or upstream direction. A sealing member 140, such as the sleeve 146, can optionally reside on the inner 420 and/or outer 422 surface of the atrial extension member 410.

Figure 36B:
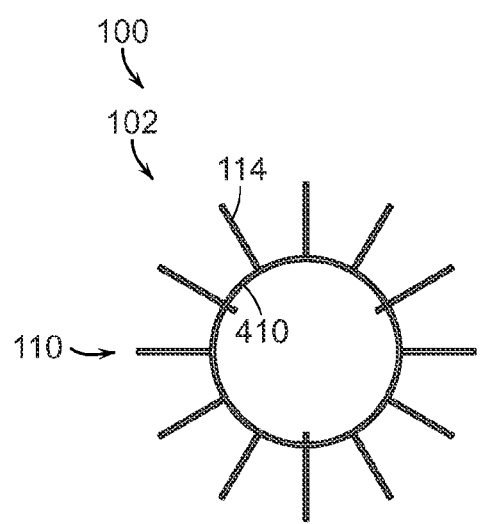
FIGS. 36B-36C are schematic, top views of an embodiment of a prosthetic heart valve device having an atrial extension member without (FIG. 36B) and with (FIG. 36C) a twisting force applied to the device in accordance with the present technology.
Figure 36C:
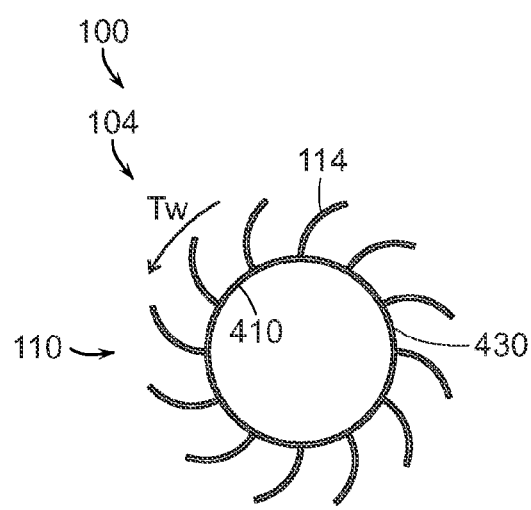

FIGS. 36B-36C are schematic, top views of an embodiment of a prosthetic heart valve device 100 having an atrial extension member 410 without (FIG. 36B) and with (FIG. 36C) a twisting force applied to the device 100 in accordance with the present technology. FIG. 36B shows the device 100 in the expanded configuration 102 having the atrial extension member 410 and a plurality of ribs 114 positioned circumferentially around the device 100 to form the retainer 110. FIG. 36B shows the device 100 in a deployed configuration 104 wherein a twisting force $T_w$ is applied to the retainer 110 such that the ribs 114 are flexed, bent and/or rotated with respect to an outer surface 430 of the device 100 and/or the atrial extension member 410 to conform to the native heart valve tissue (e.g., mitral valve annulus).

The expandable retainer, valve support, arms, atrial extension may be made from any number of suitable biocompatible materials, e.g., stainless steel, nickel-titanium alloys such as Nitinol™, various polymers, ELGILOY® (Elgin, Ill.), pyrolytic carbon, silicone, polytetrafluoroethylene (PTFE), or any number of other materials or combination of materials depending upon the desired results. The arm members may also be coated or covered with a material that promotes tissue in-growth, e.g., Dacron®, PTFE, coatings, etc.

Delivery Systems

FIGS. 37A-37D illustrate one embodiment of a delivery system 10 suitable for delivery of the prosthetic heart valve devices disclosed herein. As used in reference to the delivery system, "distal" refers to a position having a distance farther from a handle of the delivery system 10 along the longitudinal axis of the system 10, and "proximal" refers to a position having a distance closer to the handle of the delivery system 10 along the longitudinal axis of the system 10.

Figure 37A:
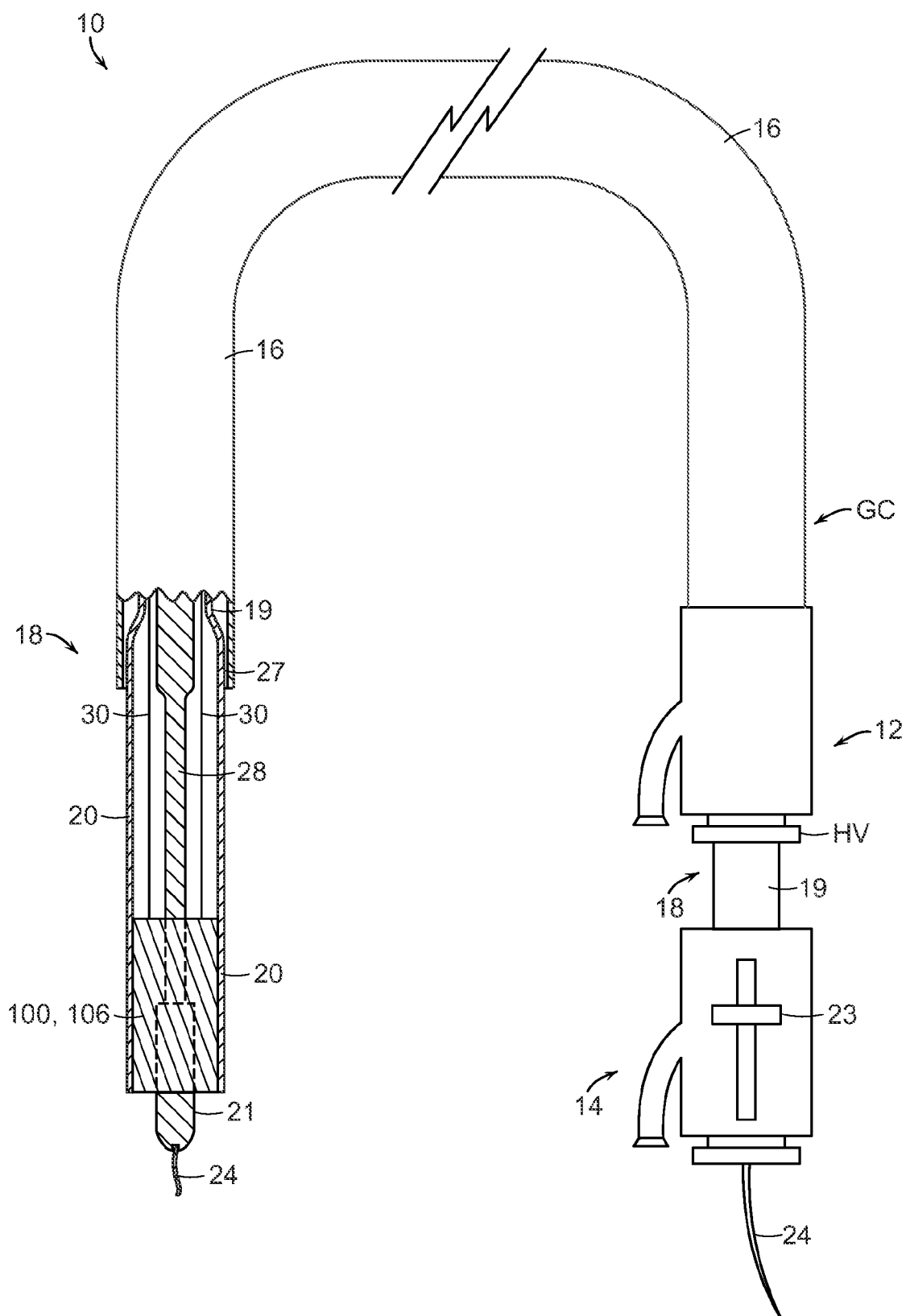
FIG. 37A is side partial cut-away view of a delivery system in accordance with an embodiment of the present technology.

FIG. 37A illustrates one embodiment of the delivery system 10 which may be used to deliver and deploy the embodiments of the prosthetic heart valve device 100 disclosed herein through the vasculature and to the heart of a patient. The delivery system 10 may optionally include a guiding catheter GC having a handle 12 coupled to a delivery shaft 16, which in one embodiment is 34 F or less, and in another embodiment, 28 F or less in diameter. The guiding catheter GC may be steerable or pre-shaped in a configuration suitable for the particular approach to the target valve. The delivery catheter 18 is placed through a hemostasis valve HV on the proximal end of guiding catheter GC and includes a flexible tubular outer shaft 19 extending to a delivery sheath 20 in which the device 100 is positioned in a collapsed or delivery configuration 106. A flexible inner shaft 28 is positioned slideably within outer shaft 19 and extends through the device 100 to a nosecone 21 at the distal end. The inner shaft 28 has a guidewire lumen through which a guidewire 24 may be slideably positioned. The device 100 is coupled to the inner shaft 28 and is releasable from the inner shaft 28 by release wires 30, as more fully described below. The delivery sheath 20 can protect and secure the device 100 in its collapsed configuration 106 during delivery. The outer shaft 20 is coupled to a retraction mechanism 23 on the handle 14 of the delivery catheter 18. Various retraction mechanisms 23 may be used, such as an axially-slidable lever, a rotatable rack and pinion gear, or other known mechanisms. In this way, the outer shaft 20 may be retracted relative to the inner shaft 28 to release (e.g., deploy) the device 100 from the sheath 20.

Figure 37B:
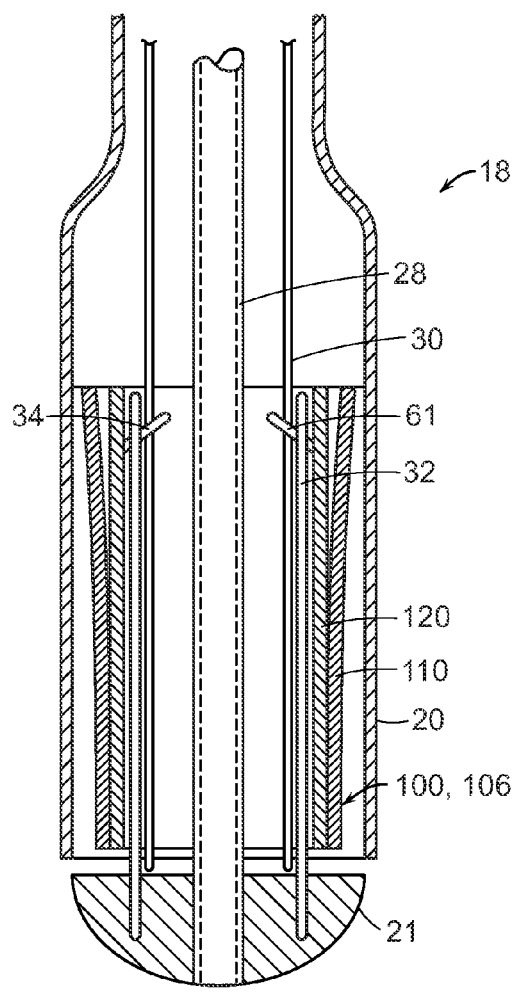
FIG. 37B is an enlarged cross-sectional view of a distal end of a delivery system in accordance with an embodiment of the present technology.
Figure 37C:
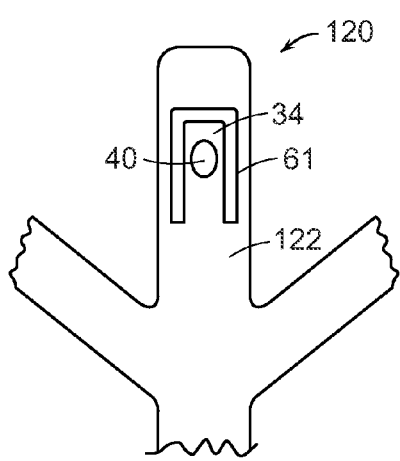
FIGS. 37C-37D are enlarged partial side views of a valve support configured for use with the delivery system of FIG. 37B in accordance with an embodiment of the present technology.
Figure 37D:
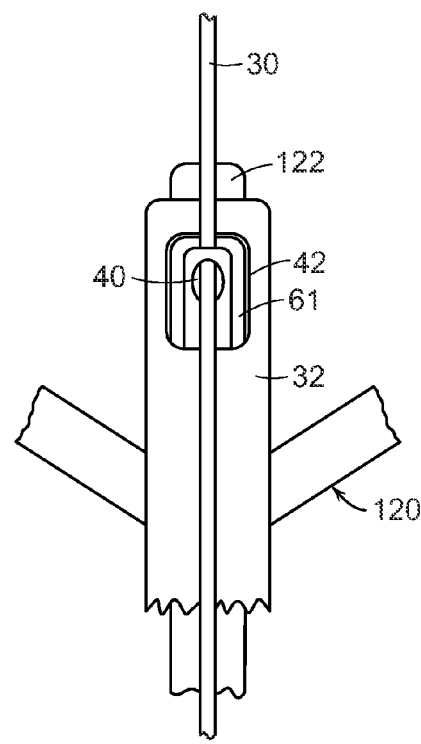

FIG. 37B shows the distal end of the delivery catheter 18 with the sheath 20 cut away to illustrate the coupling of the device 100 to the inner shaft 28. A plurality of locking fingers 32 are coupled to the nose cone 21 and extend proximally through the interior of the valve support 120 of the device 100. As shown in FIG. 37C, a selected number of posts 122 of the valve support 120 have a coupling element 61 comprising a tab 34 cut out from each post 122 at a proximal end thereof. The tab 34 may be deflected inwardly from the post 122 as shown in FIG. 37B and is configured to extend through a window 42 in the locking finger 32 as shown in FIG. 37D. The release wires 30 pass through the holes 40 in the tabs 34, which prevents the tabs 34 from being withdrawn from the windows 42 to secure the device 100 to the inner shaft 28. The pull-wires 30 can be sandwiched tightly between the tabs 34 and the locking fingers 32, such that friction temporarily prevents the pull-wire 30 from slipping in a proximal or distal direction. In this way, the sheath 20 may be refracted relative to the device 100 to permit expansion of the device 100 while the inner shaft 28 maintains the longitudinal position of the device 100 relative to the anatomy. The pull-wires 30 may extend proximally to the handle 14, for example, in between the inner shaft 28 and the outer shaft 19 or within one or more designated lumens. A suitable mechanism (not shown) on the handle 14 can allow the operator to retract the release wires 30 in a proximal direction until they are disengaged from the tabs 34. Accordingly, the device 100 can be released from the locking fingers 32 and expand for deployment at the target site.

Figure 38A:
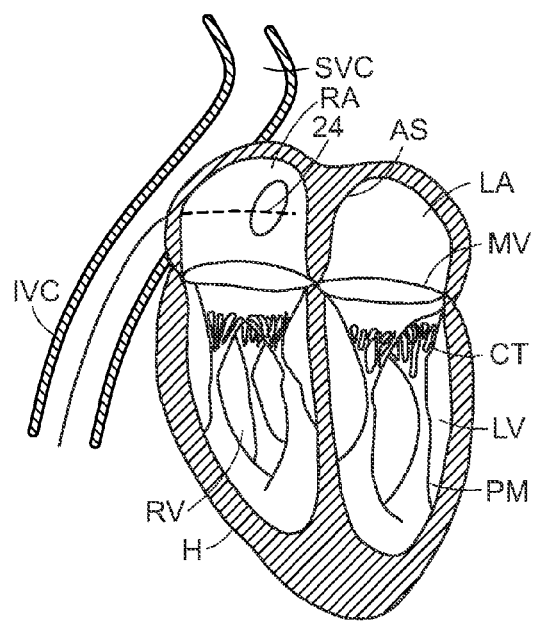
FIGS. 38A-38D are cross-sectional views of a heart showing an antegrade or trans-septal approach to the mitral valve in accordance with an embodiment of the present technology.
Figure 38B:
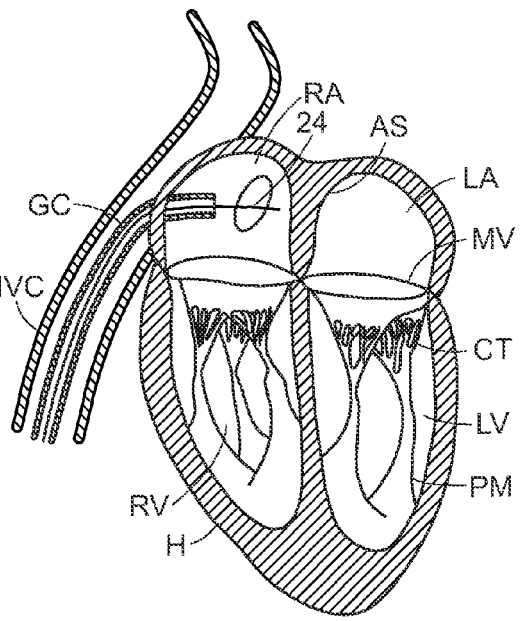
Figure 38C:
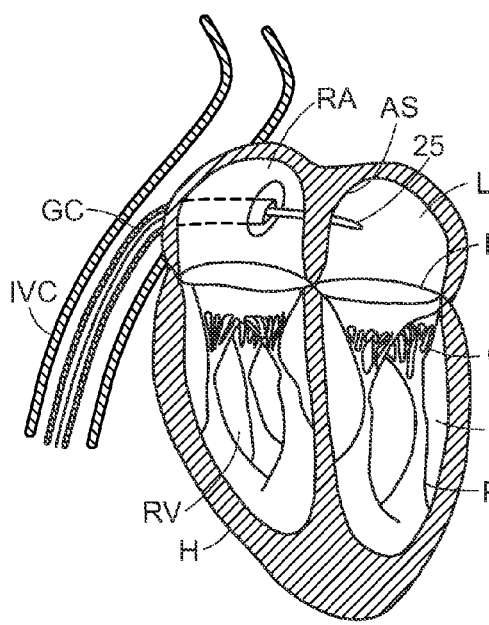
Figure 38D:
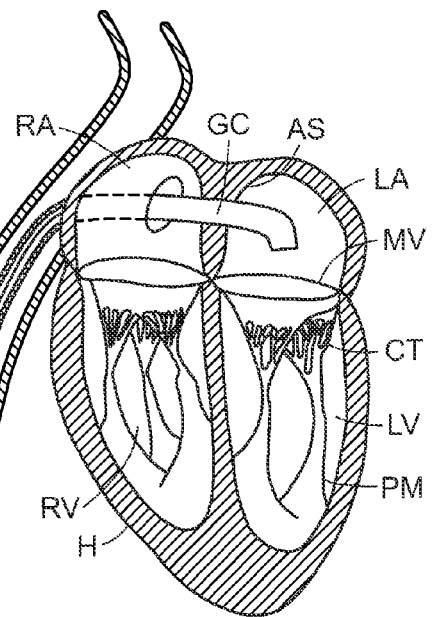

FIGS. 38A-38D are schematic, cross-sectional side views of a heart H showing a trans-septal or antegrade approach for delivering and deploying a prosthetic heart valve device 100. As shown in FIG. 38A, a guidewire 24 may be advanced intravascularly using any number of techniques, e.g., through the inferior vena cava IVC or superior vena cava SVC, through the inter-atrial septum IAS and into the right atrium RA. The guiding catheter GC may be advanced along the guidewire 24 and into the right atrium RA until reaching the anterior side of the atrial septum AS, as shown in FIG. 38B. At this point, the guidewire 24 may be exchanged for the needle 25, which is used to penetrate through the inter-atrial septum IAS (FIG. 38C). The guiding catheter GC may then be advanced over the needle 25 into the left atrium LA, as shown in FIG. 38D. The guiding catheter GC may have a pre-shaped or steerable distal end to shape or steer the guiding catheter GC such that it will direct the delivery catheter 18 (FIG. 37A) toward the mitral valve.

As an alternative to the trans-septal approach, the mitral valve may also be accessed directly through an incision in the left atrium. Access to the heart may be obtained through an intercostal incision in the chest without removing ribs, and a guiding catheter may be placed into the left atrium through an atrial incision sealed with a purse-string suture. A delivery catheter may then be advanced through the guiding catheter to the mitral valve. Alternatively, the delivery catheter may be placed directly through an atrial incision without the use of a guiding catheter.

Figure 39A:
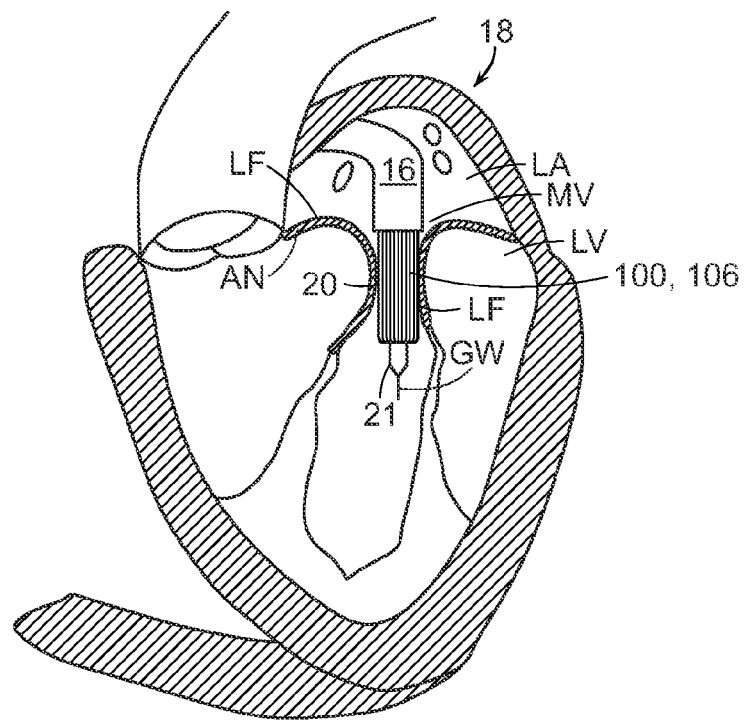
FIGS. 39A-39C are cross-sectional views of the heart illustrating a method of implanting a prosthetic heart valve device using a trans-septal approach in accordance with another embodiment of the present technology.
Figure 39B:
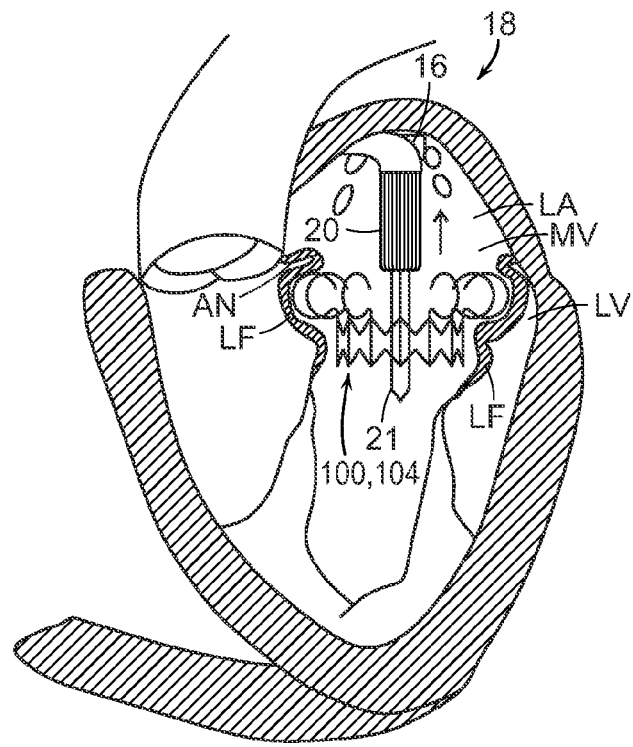
Figure 39C:
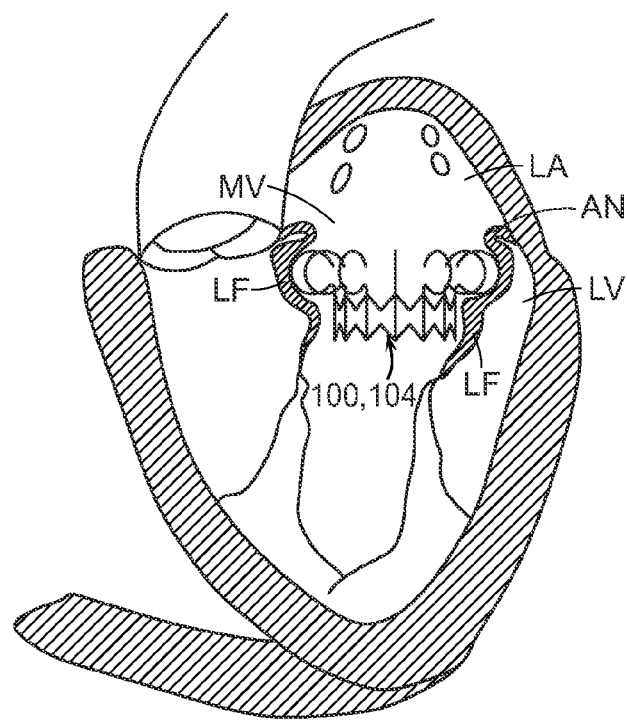

FIGS. 39A-39C are cross-sectional views of the heart illustrating a method of implanting a prosthetic heart valve device 100 using a trans-septal approach. Referring to FIGS. 39A-39C together, the distal end 21 of the delivery catheter 18 may be advanced into proximity to the mitral valve MV. Optionally, and as shown in FIG. 39A, a guidewire GW may be used over which catheter 18 may be slideably advanced over a guidewire GW. The sheath 20 of the delivery catheter 18, which contains the device 100 in a collapsed configuration 106, is advanced through the mitral valve annulus AN between native leaflets LF, as shown in FIG. 39A. Referring to FIG. 39B, the sheath 20 is then pulled back proximally relative to the distal nose cone 21 allowing the device 100 to expand such that retainer 110 pushes the leaflets LF outwardly to fold beneath the mitral valve annulus AN. After the sheath 20 has been removed and the device 100 allowed to expand, the delivery system can still be connected to the device 100 (e.g., system eyelets, not shown, are connected to the device eyelets) so that the operator can further control the placement of the device 100 as it expands toward the expanded configuration 102. For example, the device 100 may be expanded upstream or downstream of the target location then pushed downstream or upstream, respectively, into the desired target location before releasing the device 100 from delivery system 10. Once the device 100 is positioned at the target site, the pull-wires 30 (FIGS. 37A-

37B) may be refracted in a proximal direction, to detach the device 100 in the deployed configuration 104 from the delivery catheter 18. The delivery catheter 18 can then be removed as shown in FIG. 39C. Alternatively, the device 100 may not be connected to the delivery system 10 such that the device 100 deploys and is fully released from the delivery system 10.

Figure 40A:
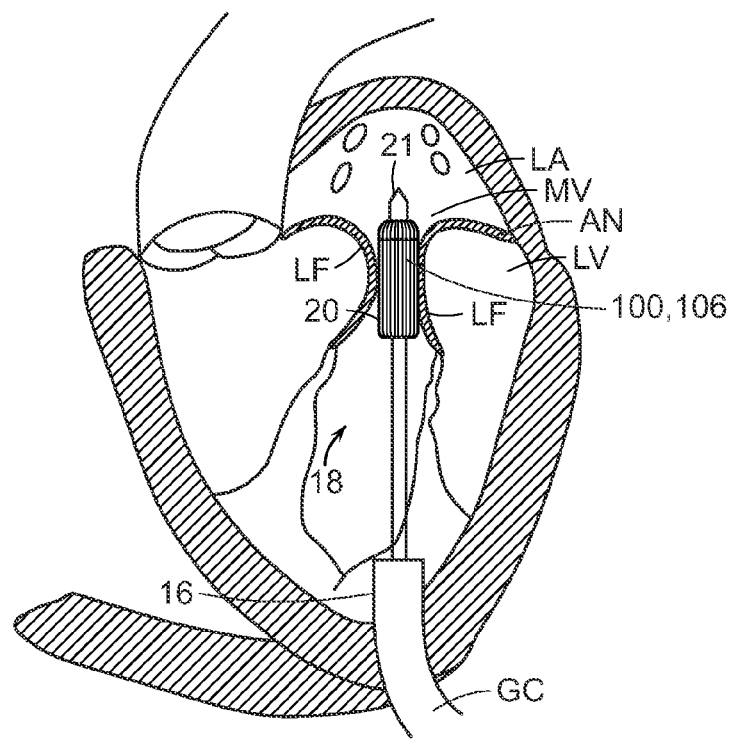
FIGS. 40A-40C are cross-sectional views of the heart illustrating a further embodiment of a method of implanting the prosthetic heart valve device using a trans-apical approach in accordance with aspects of the present technology.
Figure 40B:
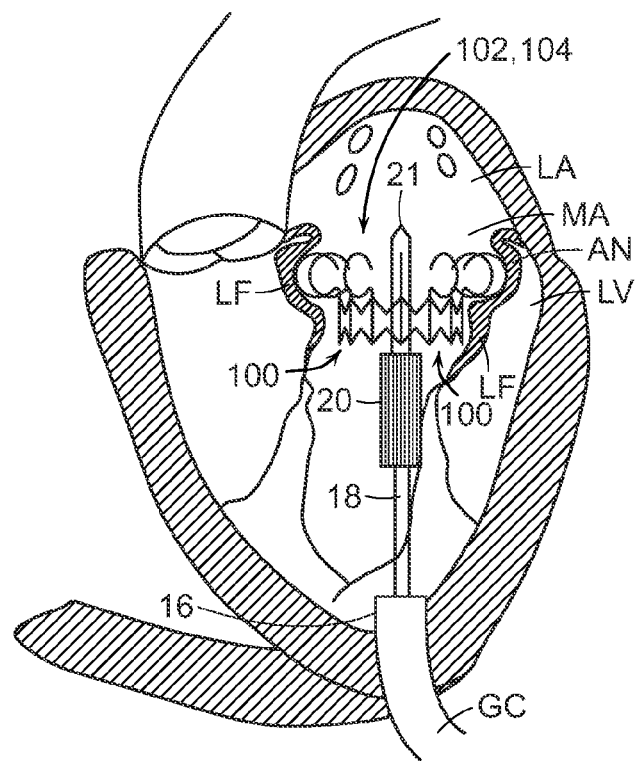
Figure 40C:
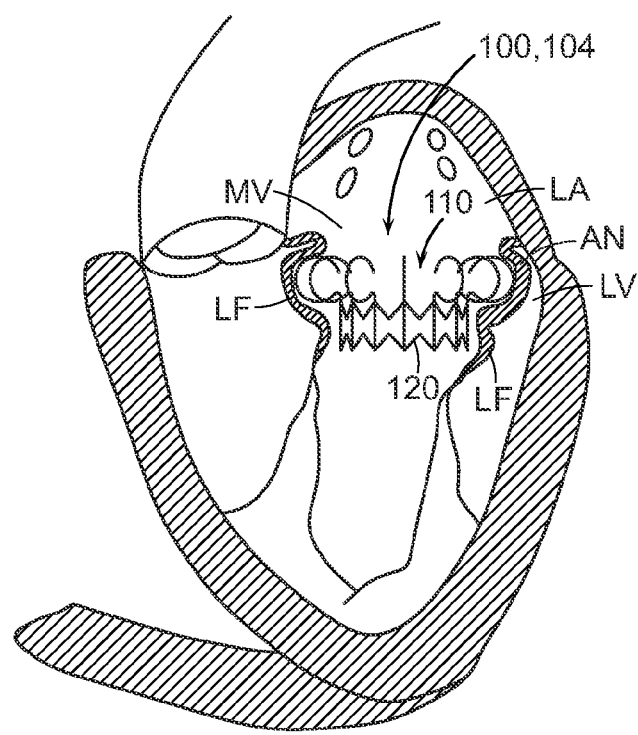

FIGS. 40A-40C illustrate delivery of the device 100 in the collapsed configuration 106 to the mitral valve MV via a trans-apical approach. Referring to FIG. 40A, the delivery catheter 18 is advanced through a guiding catheter GC that has been inserted into the left ventricle of the heart through a puncture in the left ventricle wall at or near the apex of the heart. The catheter can be sealed by a purse-string suture. Alternatively, the delivery catheter 18 may be placed directly through a purse-string-sealed trans-apical incision without a guiding catheter. The sheath 20 and the device 100 (e.g., in the collapsed configuration 106) within the sheath 20 are advanced through the mitral annulus AN between native leaflets LF as shown in FIG. 40A. Referring to FIG. 40B, the sheath 20 is pulled proximally such that the device 100 expands to the expanded and/or deployed configurations 102, 104. The delivery system 10 can remain connected to the device 100 (e.g., system eyelets, not shown, are connected to the device eyelets) after removing the sheath 20 so that the operator can control the placement of the device 100 while the device expands toward the expanded configuration 102. The pull-wires 30 may be retracted in a proximal direction to release the device 100 from the delivery system 10, allowing the delivery system 10 to be removed and the device to be fully implanted at the mitral valve MV in the deployed configuration 104. In one embodiment, the device 100 may be expanded upstream or downstream of the desired target location then pulled or pushed downstream or upstream, respectively, into the target location before releasing the device 100 from delivery system 10. Alternatively, the device 100 may not be connected to the delivery system 10 such that the device 100 deploys and is fully released from the delivery system 10.

In another embodiment, not shown, the device 100 can be mounted on an expandable balloon of a delivery catheter and expanded to its functional size by inflation of the balloon. When using a balloon delivery system, the device 100 can be advanced from the delivery shaft to initially position the device in a target location. The balloon can be inflated to fully expand the device 100. The device 100 may then be adjusted using the device locking hub to position the device into the desired implantation site (e.g., just below the annulus of the native mitral valve). In another embodiment, the balloon initially can be partially inflated to partially expand the valve assembly in the left atrium. The delivery system 10 can then be adjusted to push or pull (depending on the approach) the partially expanded valve into the implantation site, after which the valve assembly can be fully expanded to its functional size.

Additional Embodiments

Features of the prosthetic heart valve device components described above and illustrated in FIGS. 10A-40C can be modified to form additional embodiments configured in accordance with the present technology. For example, the prosthetic heart valve device 100 illustrated in FIG. 18 and other prosthetic heart valve devices described above without stabilizing members can include stabilizing members, such as arms that are coupled to the valve support or other feature and are configured to extend radially outward to engage leaflet tissue. Similarly, any of the prosthetic heart valve devices described above and illustrated in FIGS. 10A-40C can include features such as sealing members as well as stabilizing features and tissue engaging elements. Features of the prosthetic heart valve device components described above also can be interchanged to form additional embodiments of the present technology.

The following Examples are illustrative of several embodiments of the present technology.

Examples

1. A device for repair or replacement of a native heart valve, the native heart valve having an annulus and leaflets coupled to the annulus, comprising:
   a valve support having an upstream end and a downstream end extending along a longitudinal axis, the valve support having an outer surface and an inner surface, wherein the inner surface is configured to support a prosthetic valve, and wherein the valve support has a cross-sectional shape;
   an expandable retainer coupled to the upstream end of the valve support, the retainer configured to engage tissue on or near the annulus; and
   wherein the valve support is mechanically isolated from the retainer such that the cross-sectional shape of the valve support remains sufficiently stable when the retainer is deformed in a non-circular shape by engagement with the tissue.

2. A prosthetic heart valve device for treating a mitral valve, comprising:
   a valve support configured to support a valve;
   a retainer coupled to the valve support at an upstream end of the device, wherein the retainer is positionable at least partially along a subannular surface of a native mitral valve annulus, and wherein the retainer is configured to inhibit upstream migration of the device; and
   wherein the retainer is coupled to the valve support so as to mechanically isolate the valve support from distorting force exerted on the retainer by native anatomy.

3. A prosthetic heart valve device for treating a mitral valve, comprising:
   an expandable retainer configured to engage cardiac tissue at or downstream of a native mitral valve annulus; and
   a valve support coupled to and extending in a downstream direction from the expandable retainer, wherein the valve support is configured to support a prosthetic valve;
   wherein the expandable retainer is configured to conform to the shape of the native mitral valve annulus while the valve support remains substantially unchanged.

4. A prosthetic heart valve device for treating a native heart valve in a patient, comprising:
   a valve support having a generally circular shape and configured to support a prosthetic valve;
   a deformable retainer coupled to an upstream portion of the valve support and configured to engage cardiac tissue on or below an annulus of the heart valve; and
   a plurality of arms coupled to a downstream portion of the valve support, the plurality of arms configured to engage a native leaflet, wherein the arms are biased outwardly from the valve support in an unbiased configuration;
   wherein the valve support is mechanically isolated from the retainer such that deformation of the retainer does not substantially affect the generally circular shape of the valve support.

5. The device of example 1 wherein the retainer is positioned upstream of an upstream end of the valve support.

6. The device of examples 1 or 4 wherein the retainer is configured to engage valve tissue selected from an inward-facing surface of the annulus and an inward facing surface of the leaflets downstream of the annulus.

7. The device of any one of examples 1-4 wherein the device is moveable into a plurality of configurations including:
   a first configuration in which the valve support and the retainer are radially contracted, and wherein the valve support has a first cross-sectional shape;
   a second configuration in which the valve support and the retainer are radially expanded, and wherein the valve support has a second cross-sectional shape greater than the first cross-sectional shape; and
   a third configuration in which the retainer is engaged with and at least partially deformed by tissue on or near the annulus while the valve support remains in the second cross-sectional shape.

8. The device of example 7 wherein the retainer assumes the second configuration in an unbiased condition.

9. The device of example 7 wherein the retainer is deformable from the second configuration to the third configuration.

10. The device of example 7 wherein the device in the first configuration has a low profile configured for delivery through a guide catheter positioned at or near the native heart valve.

11. The device of example 10 wherein the retainer has a first diameter in the second configuration, and wherein the first diameter spans at least the distance between native commissures of the native heart valve.

12. The device of example 10 wherein the native heart valve is a mitral valve.

13. The device of example 7 wherein the retainer has an outer circumference, the outer circumference being generally circular in the second configuration and generally non-circular in the third configuration.

14. The device of example 7 wherein the retainer has an inner circumference, the inner circumference defining a passage for blood to flow through the valve support, and wherein the inner circumference is substantially circular in the third configuration.

15. The device of any one of examples 1-3 wherein the valve support is generally circular and the retainer is deformable to be generally non-circular when engaging the tissue.

16. The device of any one of examples 1-3 wherein the retainer includes a plurality of flexible ribs extending outward from the valve support and in an upstream direction, the ribs being distributed around a perimeter of the valve support.

17. The device of example 16 wherein the ribs are non-symmetrically distributed around the perimeter.

18. The device of example 16 wherein the ribs are symmetrically distributed around the perimeter.

19. The device of example 16 wherein the retainer includes between approximately 2 and about 30 ribs.

20. The device of example 16 wherein the retainer includes between approximately 6 and about 20 ribs.

21. The device of example 16 wherein the flexible ribs are arcuate ribs.

22. The device of example 21 wherein the arcuate ribs have rib tips that are oriented inwardly toward the longitudinal axis.

23. The device of any one of examples 1-4 wherein the retainer has a cross-sectional dimension greater than a corresponding cross-sectional dimension of the annulus of the native heart valve.

24. The device of any one of examples 1-4, further comprising a sealing member disposed on a surface of the retainer and configured to seal against at least the tissue on or near the annulus to inhibit blood flow between the retainer and the tissue.

25. The device of example 24 wherein the sealing member further extends around at least one of the inner surface or the outer surface of the valve support, and wherein the sealing member is configured to inhibit blood flow in a space between the valve support and the retainer.

26. The device of example 24, further comprising a plurality of piercing elements coupled to the sealing member for piercing the tissue.

27. The device of any one of examples 1-4 wherein the valve support includes a plurality of posts connected circumferentially by a plurality of struts, and wherein the retainer includes a plurality of arcuate ribs extending outward from the valve support and in an upstream direction, the ribs being distributed about a perimeter of the valve support.

28. The device of example 27 wherein the ribs are integral with the posts.

29. The device of example 27 wherein the ribs are coupled to at least one of the posts and the struts.

30. The device of example 27 wherein the individual ribs are coupled to the posts with a fastener.

31. The device of example 27 wherein the ribs are coupled to the posts with a hypotube.

32. The device of example 27 wherein the ribs are welded or bonded to the posts.

33. The device of example 1 wherein the retainer includes a plurality of flexible ribs extending outward and in an upstream direction, and wherein the plurality of flexible ribs are at least partially covered by a sealing member.

34. The device of example 33 wherein the sealing member comprises one or more of a polymer, thermoplastic polymer, a polyester, a synthetic fiber, a fiber, polyethylene terephthalate (PET), expanded polytetrafluoroethylene (ePTFE), Dacron® or bovine pericardial tissue.

35. The device of example 33 wherein the sealing member promotes tissue ingrowth into the sealing member.

36. The device of example 1, further comprising a sealing member disposed around an outer surface of the retainer, the sealing member configured to seal against the tissue to inhibit blood flow between the retainer and the tissue.

37. The device of example 1 wherein the retainer includes a plurality of flexible C-shaped ribs circumferentially positioned around an upper portion of the device, and wherein the retainer is a donut-shaped flange coupled to the upstream end of the valve support.

38. The device of example 37 wherein the C-shaped ribs have a first radius of curvature in an unbiased state, and wherein the C-shaped ribs are configured to be deformed in a deployed configuration such that the C-shaped ribs have a second radius of curvature, the second radius of curvature being smaller or greater than the first radius of curvature.

39. The device of example 37 wherein deformation of any one of the plurality of C-shaped ribs does not substantially deform the valve support.

40. The device of example 1 wherein:
   the retainer includes a plurality of flexible ribs circumferentially positioned around the valve support;

each individual rib includes a plurality of rib segments; and each rib segment has a characteristic different than another rib segment, the characteristic being selected from shape, length, profile, flexibility and orientation with respect to the longitudinal axis.

41. The device of example 40 wherein each rib segment has a segment shape selected from one of linear, curved, coiled, or angled.

42. The device of example 1 wherein the retainer includes a plurality of flexible ribs extending outward from the valve support and in an upstream direction, and wherein each individual rib has a characteristic different than another rib, the characteristic being selected from shape, height, axial strength, flexibility and orientation with respect to the longitudinal axis.

43. The device of example 1 wherein the retainer includes a plurality of flexible ribs extending outward from the valve support and in an upstream direction, and wherein ribs include a rib tip, and wherein the rib tip includes a hook, a barb or an atraumatic surface.

44. The device of example 1 wherein the retainer includes a plurality of curved ribs extending outward from the valve support and in an upstream direction, and wherein one or more ribs are deformed to modify a shape of the retainer from a generally circular shape to a generally non-circular shape in a deployed configuration.

45. The device of example 1 wherein the retainer includes a plurality of flexible ribs distributed around a perimeter of the valve support, and wherein one or more ribs bends or rotates in the deployed configuration.

46. The device of example 1 wherein the retainer includes a plurality of flexible ribs distributed around a perimeter of the valve support, and wherein each of the plurality of flexible ribs has a column strength sufficient to inhibit movement of the device relative to the annulus under the force of systolic blood pressure against a valve mounted in the valve support.

47. The device of example 1 wherein the retainer includes a plurality of flexible ribs distributed around a perimeter of the valve support, and wherein the flexible ribs are configured to absorb distorting diastolic and systolic forces generated in the heart having the native heart valve.

48. The device of any one of examples 1-4 wherein the retainer is self-expanding.

49. The device of any one of examples 1-4 wherein the retainer comprises nitinol.

50. The device of example 1 wherein:
the tissue on or near the annulus has a generally non-circular shape having a minor diameter and a major diameter generally transverse to the minor diameter;
the retainer has an outer perimeter having a major perimeter diameter and a minor perimeter diameter transverse to the major perimeter diameter while the retainer is engaged with and at least partially deformed by the tissue on or near the annulus;
the major perimeter diameter is greater than the major diameter; and
the minor perimeter diameter is greater than the minor diameter.

51. The device of example 50 wherein the retainer has an outer circumference having a diameter greater than the minor diameter while the retainer is in an expanded and unbiased configuration.

52. The device of example 50 wherein the retainer is biased toward an expanded configuration, and wherein the retainer exerts axial force against the tissue when the retainer is engaged with and at least partially deformed by the tissue on or near the annulus.

53. The device of example 1 wherein the device does not engage supra-annular tissue or tissue upstream of the annulus.

54. The device of example 1 wherein the valve support includes a plurality of posts connected circumferentially by a plurality of struts, and wherein the posts and struts are formed in a chevron configuration.

55. The device of any one of examples 1-4 wherein at least one of the retainer and the valve support comprises a nitinol mesh.

56. The device of any one of examples 1-4 wherein at least one of the retainer and the valve support comprise a shape memory material.

57. The device of any one of examples 1-4 wherein:
the valve support includes a plurality of posts connected circumferentially by a plurality of struts;
the retainer includes a plurality of flexible ribs coupled to the posts; and
the posts are more rigid than the ribs.

58. The device of example 57, further comprising a connecting ring coupled to the posts at the downstream end of the valve support.

59. The device of example 57, further comprising a support ring engaging the plurality of flexible ribs for providing circumferential support to the retainer.

60. The device of any one of examples 1-4, further comprising a plurality of tissue engaging elements on at least one of the retainer or the valve support, wherein the tissue engaging elements are configured to engage tissue on or near the annulus.

61. The device of example 60 wherein the tissue engaging elements are one of barbs, hooks or spikes.

62. The device of example 1 wherein the retainer includes an expandable mesh coupled to the upstream end of the valve support, and wherein the expandable mesh is configured to evert to form the retainer having a first cross-sectional dimension greater than a second cross-sectional dimension of the valve support.

63. The device of example 1 wherein the retainer includes an expandable mesh coupled to the upstream end of the valve support, and wherein the expandable mesh is configured to roll to form the retainer having a first cross-sectional dimension greater than a second cross-sectional dimension of the valve support.

64. The device of example 1, further comprising one or more stabilizing members to inhibit movement of the device in an upstream direction, downstream direction, or lateral direction.

65. The device of example 1, further comprising a plurality of arms coupled to the valve support and configured to receive the leaflets between the arms and the outer surface.

66. The device of example 65 wherein the arms engage a subannular surface of the annulus.

67. The device of example 1, further comprising a plurality of arms coupled to the valve support and configured to engage an inward-facing surface of the leaflets downstream of the annulus.

68. The device of example 67 wherein the arms include one or more tissue engaging elements for penetrating the inward-facing surface of the leaflets.

69. The device of examples 65 or 67 wherein the plurality of arms are configured to inhibit movement of the device toward an atrium by engagement of the annulus or the leaflets downstream of the annulus.

70. The device of examples 65 or 67 wherein the plurality of arms are moveable from an inward configuration for delivery of the device through vasculature of a patient to an outward configuration for engagement of the tissue on or near the annulus.

71. The device of example 65 wherein the arms include arm extensions for engaging the retainer.

72. The device of example 65 wherein the arms are integrally formed with the valve support.

73. The device of example 65 wherein one or more arms are connected with one or more laterally oriented arm struts.

74. The device of example 1, further comprising an atrial retainer configured to engage a supra-annular surface of the annulus or atrial tissue such that downstream movement of the device is blocked by engagement of the atrial retainer with the supra-annular surface or the atrial tissue.

75. The device of any one of examples 1-4, further comprising a valve coupled to the valve support to inhibit retrograde blood flow.

76. The device of example 75 wherein the valve is a tri-leaflet valve.

77. The device of example 75 wherein the valve is bi-leaflet valve.

78. The device of example 75 wherein the valve comprises bovine pericardium.

79. The device of example 75 wherein a plurality of commissural attachment structures couple the valve to the interior surface of the valve support.

80. The device of any one of examples 1-4, further comprising a temporary valve coupled to the valve support, wherein the valve support is further configured to receive a replacement valve after the device is implanted at the native heart valve.

81. The device of example 80 wherein the temporary valve is adapted to be displaced against the inner surface of the valve support when the replacement valve is received in the valve support.

82. The device of example 80 wherein the temporary valve comprises a removable valve, and wherein the replacement valve is secured within the valve support after the temporary valve has been removed.

83. The device of examples 2 or 3, further comprising an atrial extension member extending from the retainer to a position at least partially upstream of the native mitral annulus.

84. A method for replacement of a native heart valve having an annulus and a plurality of leaflets, the method comprising:
 positioning a prosthetic device between the leaflets in a collapsed configuration;
 allowing the prosthetic device to expand such that a retainer of the prosthetic device is in a subannular position in which it engages tissue on or below the annulus, wherein the retainer has a diameter larger than a corresponding diameter of the annulus in the subannular position; and
 allowing a valve support to expand, the valve support being coupled to the retainer at an upstream end of the valve support;
 wherein the valve support is mechanically isolated from the retainer such that deformation of the retainer when engaging the tissue does not substantially deform the valve support.

85. The method of example 84 wherein the prosthetic device comprises the device of any one of examples 1-83.

86. The method of example 84, further comprising delivering the device by catheter prior to positioning the prosthetic device between the leaflets.

87. The method of example 86, further comprising retracting a sheath on the catheter to expose the device in an expanded configuration, and moving the device in an upstream direction such that the upstream portion of the retainer engages the tissue.

88. The method of example 86, further comprising navigating the catheter configured to retain the device in a delivery configuration by one or more of a trans-septal approach from a right atrium, a trans-apical approach via a left ventricular incision or puncture, or a trans-aortic approach through the aorta.

89. A method of treating a mitral valve of a patient, the mitral valve having an annulus and leaflets, the method comprising:
 implanting a device within or adjacent to the annulus, the device comprising a valve support and a deformable retainer coupled to an upstream end of the valve support, wherein at least the retainer is disposed between the leaflets, and wherein the retainer is configured to engage tissue on or near the annulus to prevent migration of the device in an upstream direction; and
 wherein the valve support is mechanically isolated from the retainer such that a cross-sectional shape of the valve support does not substantially change if the retainer is deformed by engagement with the tissue.

90. The method of example 89, wherein implanting the device comprises:
 positioning the device between the leaflets and downstream of the annulus when the device is in a delivery configuration;
 expanding the device from the delivery configuration to an expanded configuration with the retainer extending between the leaflets; and
 moving the device in an upstream direction to engage the tissue on or downstream of the annulus with the retainer.

91. The method of example 89, further comprising radially expanding the valve support after the retainer engages the tissue on or downstream of the annulus.

92. The method of example 89 wherein the device is the device of anyone of examples 1-83.

93. The method of example 89, further comprising delivering the device by catheter prior to implantation at the mitral valve.

94. The method of example 93, further comprising retracting a sheath on the catheter to expose the device in an expanded configuration, and moving the device in an upstream direction such that the retainer engages subannular tissue.

95. The method of example 89, further comprising navigating a catheter configured to retain the device in a delivery configuration by one or more of a trans-septal approach from a right atrium, a trans-apical approach via a left ventricular incision or puncture, or a trans-aortic approach through an aorta.

96. The method of example 89, further comprising engaging one or more stabilizing members coupled to the valve support with native tissue.

97. A system to treat a mitral valve of a patient, the mitral valve having an annulus, the system comprising:
 a device comprising the device of any one of examples 1-83; and a catheter having a lumen configured to retain the device therein.

98. The system of example 97, further comprising a replacement valve configured to couple to the device after placement of the device at the mitral valve.

99. The system of example 98, further comprising a delivery catheter coupled to the replacement valve.

100. The system of example 99 wherein the catheter comprises an expandable member configured to radially expand portions of the device.

101. The system of example 99 wherein the catheter comprises a retractable sheath, the device being contained within the sheath, and wherein the device is configured to self-expand when the sheath is retracted.

102. The system of example 99 wherein the catheter comprises a guidewire lumen adapted to slideably receive a guidewire, the guidewire lumen having proximal and distal ports through which the guidewire may be slideably inserted.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for repair or replacement of a native heart valve, the native heart valve having an annulus and native leaflets associated with the annulus, comprising:
    a valve support having an inflow end and an outflow end extending along a longitudinal axis, the valve support having an outer surface and an inner surface, wherein the inner surface is configured to support a prosthetic valve, and wherein the valve support has a cross-sectional shape;
    an expandable ring-shaped retainer positioned at the inflow end of the valve support, the retainer configured to engage and seal with tissue on or near the annulus on an inner or inflow side of the native leaflets;
    wherein the inflow end of the valve support is radially inward from and longitudinally overlapping a portion of the retainer when the device is in a deployed configuration; and
    wherein the valve support is mechanically isolated from the retainer such that the cross-sectional shape of the valve support remains substantially cylindrical such that the prosthetic valve remains competent when the retainer is deformed into a non-circular shape by engagement with the tissue.

2. The device of claim 1 wherein the retainer extends upstream and radially outward of the valve support.

3. The device of claim 1 wherein the retainer is configured to engage valve tissue selected from an inward-facing surface of the annulus and an inward facing surface of the leaflets downstream of the annulus.

4. The device of claim 1 wherein the device is moveable into a plurality of configurations including:
    a first configuration in which the valve support and the retainer are radially contracted, and wherein the valve support has a first cross-sectional shape;
    a second configuration in which the valve support and the retainer are radially expanded, and wherein the valve support has a second cross-sectional shape greater than the first cross-sectional shape; and
    a third configuration in which the retainer is engaged with and at least partially deformed by tissue on or near the annulus while the valve support remains in the second cross-sectional shape.

5. The device of claim 4 wherein the retainer has an outer circumference, the outer circumference being generally circular in the second configuration and generally non-circular in the third configuration.

6. The device of claim 1 wherein at least a portion of the valve support is generally circular and the retainer is deformable to be generally non-circular when engaging the tissue.

7. The device of claim 1 wherein the valve support includes a plurality of posts connected circumferentially by a plurality of struts, and wherein the retainer includes a plurality of arcuate ribs extending outward from the valve support and in an upstream direction, the ribs being distributed about a perimeter of the valve support.

8. The device of claim 1 wherein the retainer includes a plurality of flexible ribs distributed around a perimeter of the valve support, and wherein one or more ribs bends or rotates in the deployed configuration.

9. The device of claim 1, further comprising a plurality of arms coupled to the valve support and configured to engage an inward-facing surface of the leaflets downstream of the annulus.

10. The device of claim 9 wherein the arms include one or more tissue engaging elements for penetrating the inward-facing surface of the leaflets.

11. The device of claim 9 wherein the plurality of arms are configured to inhibit movement of the device toward an atrium by engagement of the annulus or the leaflets downstream of the annulus.

12. The device of claim 9 wherein the plurality of arms are moveable from an inward configuration for delivery of the device through vasculature of a patient to an outward configuration for engagement of the tissue on or near the annulus.

13. The device of claim 1, further comprising a valve coupled to the valve support to inhibit retrograde blood flow.

14. The device of claim 13 wherein the valve is a tri-leaflet valve.

15. The device of claim 1, further comprising a sealing membrane covering the expandable retainer.

16. The device of claim 1, further comprising tissue engaging elements extending from the expandable retainer.

17. A device for repair or replacement of a native heart valve, the native heart valve having an annulus and native leaflets associated with the annulus, comprising:
   a valve support having an inflow end and an outflow end extending along a longitudinal axis, the valve support having an outer surface and an inner surface, wherein the inner surface is configured to support a prosthetic valve, and wherein the valve support has a cross-sectional shape;
   an expandable ring-shaped retainer coupled to the inflow end of the valve support, the retainer coupled to the inflow end of the valve support, the retainer configured to engage and seal with tissue on or near the annulus on an inner or inflow side of the native leaflets, wherein the retainer includes a plurality of flexible C-shaped ribs circumferentially positioned around an upper portion of the device, and wherein the retainer is a donut-shaped flange coupled to the inflow end of the valve support; and
   wherein the valve support is mechanically isolated from the retainer such that the cross-sectional shape of the valve support remains substantially cylindrical such that the prosthetic valve remains competent when the retainer is deformed into a non-circular shape by engagement with the tissue.

18. The device of claim 17 wherein the C-shaped ribs have a first radius of curvature in an unbiased state, and wherein the C-shaped ribs are configured to be deformed in a deployed configuration such that the C-shaped ribs have a second radius of curvature, the second radius of curvature being smaller or greater than the first radius of curvature.

19. A prosthetic heart valve device for treating a mitral valve, comprising:
   a valve support configured to support a valve;
   a ring-shaped retainer coupled to the valve support and positioned at an inflow end of the device, wherein the retainer is positionable between the native valve leaflets at least partially along a subannular surface of a native mitral valve annulus, and wherein the retainer is configured to form a fluid seal with heart tissue and to inhibit upstream migration of the device;
   wherein, when the prosthetic heart valve device is in a deployed configuration, the valve support is positioned radially inward from the retainer and an upstream region of the valve support overlaps a portion of the retainer along a longitudinal axis of the prosthetic heart valve device; and
   wherein the retainer is coupled to the valve support so as to mechanically isolate the valve support from distorting force exerted on the retainer by native anatomy and thereby maintain the valve support in a substantially cylindrical shape when the retainer is formed into a non-circular shape by the distorting force applied to the retainer by the native anatomy.

20. The device of claim 19 wherein the retainer is configured to engage valve tissue selected from an inward-facing surface of the annulus and an inward facing surface of the leaflets downstream of the annulus.

21. The device of claim 19 wherein the device is moveable into a plurality of configurations including:
   a first configuration in which the valve support and the retainer are radially contracted, and wherein the valve support has a first cross-sectional shape;
   a second configuration in which the valve support and the retainer are radially expanded, and wherein the valve support has a second cross-sectional shape greater than the first cross-sectional shape; and
   a third configuration in which the retainer is configured to be engaged with and at least partially deformed by tissue on or near the annulus while the valve support remains in the second cross-sectional shape.

22. The device of claim 21 wherein the retainer has an outer circumference, the outer circumference being generally circular in the second configuration and generally non-circular in the third configuration.

23. The device of claim 19 wherein at least a portion of the valve support is generally circular and the retainer is deformable to be generally non-circular when engaging the tissue.

24. The device of claim 19 wherein the valve support includes a plurality of posts connected circumferentially by a plurality of struts, and wherein the retainer includes a plurality of arcuate ribs extending outward from the valve support and in an upstream direction, the ribs being distributed about a perimeter of the valve support.

25. The device of claim 19, further comprising a plurality of arms coupled to the valve support and configured to engage an inward-facing surface of the leaflets downstream of the annulus.

26. The device of claim 25 wherein the arms include one or more tissue engaging elements for penetrating the inward-facing surface of the leaflets.

27. The device of claim 25 wherein the plurality of arms are configured to inhibit movement of the device toward an atrium by engagement of the annulus or the leaflets downstream of the annulus.

28. The device of claim 25 wherein the plurality of arms are moveable from an inward configuration for delivery of the device through vasculature of a patient to an outward configuration for engagement of the tissue on or near the annulus.

29. The device claim 19, further comprising a valve coupled to the valve support to inhibit retrograde blood flow.

30. The device of claim 29 wherein the valve is a tri-leaflet valve.

31. A prosthetic heart valve device for treating a mitral valve, comprising:
   a flexible ring-shaped retainer configured to be positioned between the native valve leaflets and to engage cardiac tissue at or downstream of a native mitral valve annulus so as to inhibit movement of the prosthetic heart valve device and to create a seal with the cardiac tissue; and
   an expandable valve support coupled to and extending in an outflow direction with respect to the retainer, wherein the valve support is configured to contain a prosthetic valve having a plurality of leaflets, the valve support having a substantially cylindrical deployed shape in an expanded state in which the leaflets of the prosthetic valve seal with one another;

wherein, in the expanded state, an inflow portion of the valve support is longitudinally overlapping a portion of the retainer and positioned radially inward from the retainer; and wherein the retainer is configured to flex radially to adapt to a non-circular shape of the native mitral valve annulus and the valve support remains in the substantially cylindrical deployed shape after the retainer has adapted to the non-circular shape.

32. The device of claim 31 wherein the retainer is configured to engage valve tissue selected from an inward-facing surface of the annulus and an inward facing surface of the leaflets downstream of the annulus.

33. The device of claim 31 wherein the device is moveable into a plurality of configurations including:
a first configuration in which the valve support and the retainer are radially contracted, and wherein the valve support has a first cross-sectional shape;
a second configuration in which the valve support and the retainer are radially expanded, and wherein the valve support has a second cross-sectional shape greater than the first cross-sectional shape; and
a third configuration in which the retainer is configured to be engaged with and at least partially deformed by tissue on or near the annulus while the valve support remains in the second cross-sectional shape.

34. The device of claim 33 wherein the retainer has an outer circumference, the outer circumference being generally circular in the second configuration and generally non-circular in the third configuration.

35. The device of claim 31 wherein the valve support is substantially cylindrical and the retainer is deformable to be generally non-circular when engaging the tissue.

36. The device of claim 31, further comprising a plurality of arms coupled to the valve support and configured to engage an inward-facing surface of the leaflets downstream of the annulus.

37. The device of claim 36 wherein the arms include one or more tissue engaging elements for penetrating the inward-facing surface of the leaflets.

38. The device of claim 36 wherein the plurality of arms are configured to inhibit movement of the device toward an atrium by engagement of the annulus or the leaflets downstream of the annulus.

39. The device of claim 36 wherein the plurality of arms are moveable from an inward configuration for delivery of the device through vasculature of a patient to an outward configuration for engagement of the tissue on or near the annulus.

40. The device claim 31, further comprising a valve coupled to the valve support to inhibit retrograde blood flow.

41. The device of claim 40 wherein the valve is a tri-leaflet valve.

42. A prosthetic heart valve device comprising:
an expandable valve support having an inflow end and an outflow end extending along a longitudinal axis, the valve support having an outer surface and an inner surface, wherein the inner surface is configured to support a prosthetic valve, and wherein the valve support has a cross-sectional shape;
an expandable retainer coupled to and encircling the valve support, the retainer configured to engage and seal with tissue on or near a native heart valve annulus on an inner or inflow side of the heart valve annulus or native heart valve leaflets;
wherein the inflow end of the valve support is radially inward from and longitudinally overlapping a portion of the retainer when the device is in a deployed configuration; and
wherein the valve support is mechanically isolated from the retainer such that the cross-sectional shape of the valve support remains substantially cylindrical such that the prosthetic valve remains competent when the retainer is deformed into a non-circular shape by engagement with the tissue.

* * * * *